(12) United States Patent
Ashraf

(10) Patent No.: US 12,270,134 B2
(45) Date of Patent: *Apr. 8, 2025

(54) SHAPED NONWOVENS THAT EXHIBIT HIGH VISUAL RESOLUTION

(71) Applicant: The Procter & Gamble Company, Cincinnati, OH (US)

(72) Inventor: Arman Ashraf, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 128 days.

This patent is subject to a terminal disclaimer.

(21) Appl. No.: 18/047,766

(22) Filed: Oct. 19, 2022

(65) Prior Publication Data
US 2023/0061263 A1     Mar. 2, 2023

Related U.S. Application Data

(63) Continuation of application No. 16/816,323, filed on Mar. 12, 2020, now Pat. No. 11,505,884.

(Continued)

(51) Int. Cl.
*B32B 5/02*     (2006.01)
*A61F 13/511*   (2006.01)
(Continued)

(52) U.S. Cl.
CPC ........... *D04H 3/018* (2013.01); *A61F 13/511* (2013.01); *A61F 13/51104* (2013.01); *A61F 13/513* (2013.01); *A61F 13/51305* (2013.01); *A61F 13/514* (2013.01); *A61F 13/51476* (2013.01); *B32B 3/26* (2013.01); *B32B 5/022* (2013.01); *B32B 5/142* (2013.01); *B32B 33/00* (2013.01); *D04H 3/16* (2013.01);
(Continued)

(58) Field of Classification Search
None
See application file for complete search history.

(56) References Cited

U.S. PATENT DOCUMENTS 3,274,018 A    9/1966  Russell et al.
3,881,987 A    5/1975  Benz
(Continued)

FOREIGN PATENT DOCUMENTS

CN          1685099 A       10/2005
CN          103108616 A      5/2013
(Continued)

OTHER PUBLICATIONS

Machine Translation of WO-2018193775-A1, Oct. 2018 (Year: 2018).*

(Continued)

*Primary Examiner* — Jeffrey A Vonch
(74) *Attorney, Agent, or Firm* — Christian M. Best; Andrew J. Mueller

(57) ABSTRACT

A nonwoven fabric is disclosed. The nonwoven fabric can include a first surface and a second surface and at least a first visually discernible zone of three-dimensional features on one of the first or second surface. Each of the three-dimensional features can define a microzone comprising a first region and a second region. The first and second regions can have a difference in values for an intensive property, and the first visually discernible zone can exhibit a high visual resolution.

20 Claims, 44 Drawing Sheets

Related U.S. Application Data

(60) Provisional application No. 62/819,729, filed on Mar. 18, 2019.

(51) Int. Cl.

| | | |
|---|---|---|
| *A61F 13/513* | (2006.01) | |
| *A61F 13/514* | (2006.01) | |
| *A61F 13/515* | (2006.01) | |
| *B32B 3/26* | (2006.01) | |
| *B32B 5/14* | (2006.01) | |
| *B32B 33/00* | (2006.01) | |
| *D04H 3/018* | (2012.01) | |
| *D04H 3/16* | (2006.01) | |
| *B32B 3/28* | (2006.01) | |
| *B32B 3/30* | (2006.01) | |
| *B32B 5/26* | (2006.01) | |
| *D04H 3/00* | (2012.01) | |

(52) U.S. Cl.
CPC ............. *A61F 13/51121* (2013.01); *A61F 2013/51178* (2013.01); *A61F 2013/51186* (2013.01); *A61F 2013/51377* (2013.01); *A61F 2013/51452* (2013.01); *A61F 13/51456* (2013.01); *A61F 2013/51486* (2013.01); *A61F 2013/5149* (2013.01); *B32B 3/28* (2013.01); *B32B 3/30* (2013.01); *B32B 5/266* (2021.05); *B32B 5/267* (2021.05); *Y10T 428/24479* (2015.01); *Y10T 428/24595* (2015.01); *Y10T 428/24603* (2015.01); *Y10T 428/31* (2015.01); *Y10T 442/60* (2015.04); *Y10T 442/659* (2015.04); *Y10T 442/66* (2015.04); *Y10T 442/671* (2015.04); *Y10T 442/681* (2015.04)

(56) References Cited

U.S. PATENT DOCUMENTS

| | | |
|---|---|---|
| 4,079,739 A | 3/1978 | Whitehead |
| 4,333,979 A | 6/1982 | Sciaraffa |
| 4,741,941 A | 5/1988 | Englebert |
| 4,970,104 A | 11/1990 | Radwanski |
| 5,245,025 A | 9/1993 | Trokhan et al. |
| 5,277,761 A | 1/1994 | Phan et al. |
| 5,334,289 A | 8/1994 | Trokhan |
| 5,514,523 A | 5/1996 | Trokhan |
| 5,556,509 A | 9/1996 | Trokhan et al. |
| 5,575,874 A | 11/1996 | Griesbach, III |
| 5,599,420 A | 2/1997 | Yeo |
| 5,643,653 A * | 7/1997 | Griesbach, III ......... D04H 1/54 604/370 |
| 5,708,034 A | 1/1998 | Kleemann et al. |
| 5,725,927 A | 3/1998 | Zilg et al. |
| 5,858,504 A | 1/1999 | Fitting |
| 5,863,639 A | 1/1999 | Franke et al. |
| 5,895,623 A | 4/1999 | Trokhan |
| 5,916,661 A | 6/1999 | Benson |
| 5,919,556 A | 7/1999 | Barnholtz |
| 6,039,555 A | 3/2000 | Tsuji et al. |
| 6,139,941 A | 10/2000 | Jankevics |
| 6,150,002 A | 11/2000 | Varona |
| 6,319,239 B1 | 11/2001 | Daniels |
| 6,319,455 B1 | 11/2001 | Kauschke et al. |
| 6,331,268 B1 | 12/2001 | Kauschke et al. |
| 6,331,345 B1 | 12/2001 | Kauschke et al. |
| 6,361,638 B2 | 3/2002 | Takai |
| 6,383,431 B1 | 5/2002 | Dobrin |
| 6,395,957 B1 | 5/2002 | Chen |
| 6,436,512 B1 | 8/2002 | Kauschke et al. |
| 6,437,214 B1 | 8/2002 | Everett et al. |
| 6,610,173 B1 | 8/2003 | Lindsay et al. |
| 6,632,504 B1 | 10/2003 | Gillespie |
| D483,187 S | 12/2003 | Cheng |
| 6,673,418 B1 | 1/2004 | Deolivera |
| 6,818,802 B2 | 11/2004 | Takai et al. |
| 6,911,574 B1 | 6/2005 | Mizutani |
| 7,371,919 B1 | 5/2008 | Busam |
| 7,507,463 B2 | 3/2009 | Noda et al. |
| 7,553,535 B2 | 6/2009 | Noda et al. |
| 7,662,462 B2 | 2/2010 | Noda et al. |
| 7,897,240 B2 | 3/2011 | Noda et al. |
| 7,954,213 B2 | 6/2011 | Mizutani |
| 7,955,549 B2 | 6/2011 | Noda et al. |
| 8,143,177 B2 | 3/2012 | Noda |
| 8,183,431 B2 | 5/2012 | Noda et al. |
| 8,273,941 B2 | 9/2012 | Uematsu et al. |
| 8,304,600 B2 | 11/2012 | Noda et al. |
| 8,574,209 B2 | 11/2013 | Nishitani et al. |
| 8,585,666 B2 | 11/2013 | Weisman |
| 8,758,569 B2 | 6/2014 | Aberg et al. |
| 8,853,108 B2 | 10/2014 | Ahoniemi |
| 8,865,965 B2 | 10/2014 | Sato et al. |
| 8,906,275 B2 | 12/2014 | Davis |
| 9,095,477 B2 | 8/2015 | Yamaguchi et al. |
| 9,156,229 B2 | 10/2015 | Noda et al. |
| 9,205,005 B2 | 12/2015 | Kikuchi et al. |
| 9,453,303 B2 | 9/2016 | Aberg |
| 9,732,454 B2 | 8/2017 | Davis |
| 9,877,876 B2 | 1/2018 | Huang |
| 9,903,070 B2 | 2/2018 | Mourad et al. |
| 10,190,244 B2 | 1/2019 | Ashraf |
| 10,934,645 B2 | 3/2021 | Ashraf et al. |
| 11,505,884 B2 | 11/2022 | Ashraf |
| 2001/0029141 A1 | 10/2001 | Mizutani |
| 2001/0053901 A1 | 12/2001 | Mizutani et al. |
| 2002/0034914 A1 | 3/2002 | De Leon et al. |
| 2002/0052582 A1 | 5/2002 | Takai et al. |
| 2002/0055310 A1 * | 5/2002 | Falk ................. D03D 9/00 162/263 |
| 2002/0068150 A1 | 6/2002 | Taneichi et al. |
| 2002/0107495 A1 * | 8/2002 | Chen .................. A61F 13/513 604/374 |
| 2002/0153271 A1 | 10/2002 | Mcmanus |
| 2002/0180092 A1 | 12/2002 | Abba et al. |
| 2002/0193032 A1 | 12/2002 | Newkirk et al. |
| 2003/0021951 A1 | 1/2003 | Desai |
| 2003/0028165 A1 | 2/2003 | Curro et al. |
| 2003/0050615 A1 | 3/2003 | Sakamoto et al. |
| 2003/0073367 A1 | 4/2003 | Kopacz et al. |
| 2003/0082358 A1 | 5/2003 | Wenstrup |
| 2003/0093045 A1 | 5/2003 | Erdman |
| 2003/0118777 A1 | 6/2003 | Chang et al. |
| 2003/0119404 A1 | 6/2003 | Belau |
| 2003/0125687 A1 | 7/2003 | Gubernick et al. |
| 2003/0135967 A1 * | 7/2003 | Putnam .................. D04H 1/49 28/104 |
| 2003/0143376 A1 | 7/2003 | Toyoshima et al. |
| 2003/0167044 A1 | 9/2003 | Toyoshima et al. |
| 2003/0203162 A1 | 10/2003 | Fenwick |
| 2003/0203691 A1 | 10/2003 | Fenwick et al. |
| 2003/0211802 A1 | 11/2003 | Keck et al. |
| 2003/0232558 A1 | 12/2003 | Moody et al. |
| 2004/0029479 A1 * | 2/2004 | Snider .................. D04H 1/495 28/104 |
| 2004/0059309 A1 | 3/2004 | Nortman |
| 2004/0109911 A1 | 6/2004 | Boegli |
| 2004/0111848 A1 | 6/2004 | Miyamoto et al. |
| 2004/0254554 A1 | 12/2004 | Mavinkurve et al. |
| 2005/0008825 A1 | 1/2005 | Casey et al. |
| 2005/0148257 A1 * | 7/2005 | Hermans ............. D21H 27/008 428/292.1 |
| 2005/0148971 A1 | 7/2005 | Kuroda et al. |
| 2006/0005717 A1 | 1/2006 | Barge et al. |
| 2006/0087053 A1 | 4/2006 | Odonnell |
| 2006/0105075 A1 | 5/2006 | Otsubo |
| 2006/0128247 A1 | 6/2006 | Skoog et al. |
| 2006/0131777 A1 | 6/2006 | Debyser et al. |
| 2006/0161130 A1 | 7/2006 | Zacharias et al. |
| 2006/0189954 A1 | 8/2006 | Kudo |
| 2006/0234586 A1 | 10/2006 | Wong et al. |
| 2006/0286343 A1 | 12/2006 | Curro |
| 2006/0287636 A1 | 12/2006 | Sakai et al. |
| 2007/0026753 A1 | 2/2007 | Neely |

(56) References Cited

U.S. PATENT DOCUMENTS

| | | | |
|---|---|---|---|
| 2007/0045143 A1 | 3/2007 | Clough | |
| 2007/0045144 A1 | 3/2007 | Wheeler | |
| 2007/0074832 A1 | 4/2007 | Ampulski | |
| 2007/0074833 A1 | 4/2007 | Ampulski | |
| 2007/0087169 A1* | 4/2007 | McFall | A61F 13/5116 428/156 |
| 2007/0128411 A1 | 6/2007 | Kawai et al. | |
| 2007/0163454 A1 | 7/2007 | Orlandi et al. | |
| 2007/0179466 A1 | 8/2007 | Tremblay | |
| 2007/0226970 A1* | 10/2007 | Pourdeyhimi | D04H 1/492 28/100 |
| 2007/0255247 A1 | 11/2007 | Moberg-alehammar | |
| 2007/0298214 A1 | 12/2007 | Noda et al. | |
| 2007/0298667 A1 | 12/2007 | Noda et al. | |
| 2008/0044628 A1 | 2/2008 | Noda et al. | |
| 2008/0102250 A1 | 5/2008 | Ostendorf et al. | |
| 2008/0102261 A1 | 5/2008 | Hupp et al. | |
| 2008/0149292 A1 | 6/2008 | Scherb | |
| 2008/0300562 A1* | 12/2008 | Ahoniemi | B32B 5/145 604/385.01 |
| 2009/0123707 A1* | 5/2009 | Skoog | D04H 1/498 264/103 |
| 2009/0151849 A1* | 6/2009 | MacDonald | D04H 1/56 156/64 |
| 2009/0209156 A1 | 8/2009 | Pedoja | |
| 2009/0240222 A1 | 9/2009 | Tomoko et al. | |
| 2010/0035014 A1 | 2/2010 | Hammons | |
| 2010/0036346 A1 | 2/2010 | Hammons | |
| 2010/0036349 A1 | 2/2010 | Hammons et al. | |
| 2010/0048072 A1 | 2/2010 | Kauschke | |
| 2010/0130952 A1 | 5/2010 | Murai | |
| 2010/0249740 A1 | 9/2010 | Miyamoto et al. | |
| 2010/0280474 A1* | 11/2010 | Bruzadin | A61F 13/4758 604/378 |
| 2010/0312208 A1 | 12/2010 | Bond et al. | |
| 2011/0060301 A1* | 3/2011 | Nishikawa | A61F 13/4756 156/220 |
| 2011/0073513 A1 | 3/2011 | Weisman et al. | |
| 2011/0114277 A1 | 5/2011 | Spitzer et al. | |
| 2011/0123775 A1 | 5/2011 | Westwood | |
| 2011/0196330 A1 | 8/2011 | Hammons | |
| 2011/0250378 A1 | 10/2011 | Eaton | |
| 2011/0313385 A1 | 12/2011 | Hammons et al. | |
| 2012/0004633 A1 | 1/2012 | R. Marcelo et al. | |
| 2012/0023693 A1 | 2/2012 | Pung et al. | |
| 2012/0027997 A1* | 2/2012 | Aberg | D04H 1/46 428/158 |
| 2012/0095426 A1* | 4/2012 | Visscher | A61F 13/5116 604/385.01 |
| 2012/0107567 A1 | 5/2012 | Terada et al. | |
| 2012/0196091 A1 | 8/2012 | Mizutani et al. | |
| 2012/0226250 A1 | 9/2012 | Sato et al. | |
| 2012/0238984 A1* | 9/2012 | Paldey | A61F 13/539 604/378 |
| 2012/0276239 A1 | 11/2012 | Coe | |
| 2012/0276331 A1 | 11/2012 | Orr | |
| 2012/0276341 A1 | 11/2012 | Lake | |
| 2012/0277705 A1 | 11/2012 | Marinelli | |
| 2012/0277706 A1 | 11/2012 | Marinelli | |
| 2012/0282436 A1 | 11/2012 | Coe | |
| 2013/0112584 A1 | 5/2013 | Gaspari | |
| 2013/0137328 A1 | 5/2013 | Mitsuno | |
| 2013/0139960 A1 | 6/2013 | Maruyama | |
| 2013/0171421 A1 | 7/2013 | Weisman | |
| 2013/0178811 A1 | 7/2013 | Kikuchi et al. | |
| 2013/0178815 A1 | 7/2013 | Ohashi et al. | |
| 2013/0232712 A1 | 9/2013 | Kawai | |
| 2013/0236700 A1 | 9/2013 | Yamanaka et al. | |
| 2013/0253461 A1 | 9/2013 | Xu et al. | |
| 2013/0280481 A1 | 10/2013 | Mitsuno | |
| 2013/0320584 A1 | 12/2013 | Davis et al. | |
| 2013/0344286 A1 | 12/2013 | Mitsuno et al. | |
| 2014/0000004 A1 | 1/2014 | Baron et al. | |
| 2014/0004307 A1 | 1/2014 | Sheehan | |
| 2014/0023822 A1 | 1/2014 | Tai | |
| 2014/0039434 A1 | 2/2014 | Xu et al. | |
| 2014/0039438 A1 | 2/2014 | Ferrer | |
| 2014/0121623 A1 | 5/2014 | Kirby et al. | |
| 2014/0127460 A1 | 5/2014 | Xu | |
| 2014/0154459 A1 | 6/2014 | Krautkramer et al. | |
| 2014/0234575 A1 | 8/2014 | Mitsuno | |
| 2014/0276517 A1 | 9/2014 | Chester | |
| 2014/0296815 A1 | 10/2014 | Takken | |
| 2014/0305570 A1 | 10/2014 | Matsunaga | |
| 2014/0324009 A1 | 10/2014 | Lee | |
| 2014/0336605 A1 | 11/2014 | Hardie et al. | |
| 2015/0038933 A1 | 2/2015 | Day | |
| 2015/0057627 A1 | 2/2015 | Noda et al. | |
| 2015/0080837 A1* | 3/2015 | Rosati | A61F 13/84 604/385.101 |
| 2015/0173967 A1 | 6/2015 | Kreuzer | |
| 2015/0250662 A1 | 9/2015 | Isele et al. | |
| 2015/0250663 A1 | 9/2015 | Wagner et al. | |
| 2015/0265473 A1 | 9/2015 | Hammons et al. | |
| 2015/0282999 A1 | 10/2015 | Arizti | |
| 2015/0283001 A1 | 10/2015 | Arizti et al. | |
| 2016/0067119 A1 | 3/2016 | Weisman | |
| 2016/0074254 A1 | 3/2016 | Orr et al. | |
| 2016/0074256 A1 | 3/2016 | Strube et al. | |
| 2016/0076182 A1 | 3/2016 | Strube et al. | |
| 2016/0076184 A1 | 3/2016 | Orr et al. | |
| 2016/0106633 A1 | 4/2016 | Nagata | |
| 2016/0129661 A1 | 5/2016 | Arora | |
| 2016/0136009 A1 | 5/2016 | Weisman | |
| 2016/0235590 A1 | 8/2016 | Coe et al. | |
| 2017/0014281 A1 | 1/2017 | Xie | |
| 2017/0022660 A1 | 1/2017 | Suer et al. | |
| 2017/0027774 A1 | 2/2017 | Ashraf | |
| 2017/0029993 A1 | 2/2017 | Ashraf | |
| 2017/0029994 A1 | 2/2017 | Ashraf | |
| 2017/0056256 A1 | 3/2017 | Smith | |
| 2017/0121873 A1 | 5/2017 | Kimura et al. | |
| 2017/0191198 A1 | 7/2017 | Ashraf | |
| 2017/0258650 A1 | 9/2017 | Rosati | |
| 2017/0259524 A1 | 9/2017 | Neton et al. | |
| 2017/0260665 A1 | 9/2017 | Kauschke et al. | |
| 2017/0348163 A1 | 12/2017 | Lakso | |
| 2018/0112357 A1 | 4/2018 | Wang et al. | |
| 2018/0147755 A1 | 5/2018 | Fukushima | |
| 2018/0168893 A1 | 6/2018 | Ashraf | |
| 2018/0177645 A1 | 6/2018 | Kimura et al. | |
| 2018/0178543 A1 | 6/2018 | Fujimoto | |
| 2018/0193208 A1* | 7/2018 | Hashimoto | A61F 13/15 |
| 2018/0214318 A1* | 8/2018 | Ashraf | A61F 13/51456 |
| 2018/0214321 A1 | 8/2018 | Ashraf | |
| 2018/0216269 A1* | 8/2018 | Ashraf | D04H 3/147 |
| 2018/0216270 A1 | 8/2018 | Ashraf | |
| 2018/0216271 A1 | 8/2018 | Ashraf | |
| 2018/0228659 A1* | 8/2018 | Conrad | B32B 5/022 |
| 2018/0245252 A1 | 8/2018 | Groten et al. | |
| 2019/0003079 A1 | 1/2019 | Ashraf | |
| 2019/0003080 A1 | 1/2019 | Ashraf | |
| 2019/0003709 A1 | 1/2019 | Borschke et al. | |
| 2019/0060140 A1 | 2/2019 | Oshima et al. | |
| 2019/0112737 A1 | 4/2019 | Ashraf | |
| 2019/0142654 A1* | 5/2019 | Uda | A61F 13/494 604/383 |
| 2019/0298587 A1 | 10/2019 | Ashraf | |
| 2019/0336358 A1* | 11/2019 | Goda | A61F 13/511 |
| 2019/0374406 A1 | 12/2019 | Morimoto et al. | |
| 2020/0054501 A1 | 2/2020 | Seto et al. | |
| 2020/0268571 A1* | 8/2020 | Miyama | A61F 13/51121 |
| 2020/0289341 A1 | 9/2020 | Kuwahata | |
| 2020/0299881 A1 | 9/2020 | Ashraf | |

FOREIGN PATENT DOCUMENTS

| | | | |
|---|---|---|---|
| CN | 203400265 U | | 1/2014 |
| CN | 103649993 A | | 3/2014 |
| CN | 103824259 A | | 5/2014 |
| CN | 104083254 A | | 10/2014 |
| CN | 203988682 U | * | 12/2014 |
| CN | 104507436 A | | 4/2015 |

(56) References Cited

FOREIGN PATENT DOCUMENTS

| | | | |
|---|---|---|---|
| CN | 105555240 A | | 5/2016 |
| CN | 105926163 A | * | 9/2016 |
| CN | 206138291 U | * | 5/2017 |
| EA | 2660377 B1 | | 4/2014 |
| EP | 1227181 A2 | | 7/2002 |
| JP | S56140153 A | | 11/1981 |
| JP | 02017126 U | | 5/1990 |
| JP | 2000290888 A | | 10/2000 |
| JP | 2002249965 A | | 9/2002 |
| JP | 2003033397 A | | 2/2003 |
| JP | 2003070841 A | | 3/2003 |
| JP | 2003275239 A | | 9/2003 |
| JP | 2004113489 A | | 4/2004 |
| JP | 2004169235 A | | 6/2004 |
| JP | 2006175688 A | * | 7/2006 |
| JP | 2006175689 A | * | 7/2006 |
| JP | 2006255051 A | | 9/2006 |
| JP | 2007084958 A | * | 4/2007 |
| JP | 2007167212 A | | 7/2007 |
| JP | 2007191846 A | | 8/2007 |
| JP | 2007195958 A | | 8/2007 |
| JP | 2008161302 A | * | 7/2008 ........ A61F 13/51104 |
| JP | 4187146 B2 | | 9/2008 |
| JP | 2009000512 A | | 1/2009 |
| JP | 2010024573 A | | 2/2010 |
| JP | 2011015707 A | | 1/2011 |
| JP | 2012125629 A | | 7/2012 |
| JP | 2012149370 A | * | 8/2012 ............... D04H 1/54 |
| JP | 62055119 | | 12/2012 |
| JP | 2013180171 A | | 9/2013 |
| JP | 2014070299 A | | 4/2014 |
| JP | 2014097257 A | | 5/2014 |
| JP | 5561420 B1 | | 6/2014 |
| JP | 2014188042 A | | 10/2014 |
| JP | 2014200372 A | * | 10/2014 |
| JP | 2015112339 A | * | 6/2015 |
| JP | 2015112340 A | * | 6/2015 |
| JP | 2016028785 A | * | 3/2016 ............. A61F 13/15 |
| JP | 2017000126 A | | 1/2017 |
| JP | 6271657 B1 | | 1/2018 |
| JP | 2018000778 A | | 1/2018 |
| JP | 2019044294 A | * | 3/2019 |
| JP | 2022525402 A | | 5/2022 |
| TW | 200951264 A | | 12/2009 |
| WO | WO-02061191 A2 | * | 8/2002 ............... B05D 1/42 |
| WO | 2003015681 | | 2/2003 |
| WO | 2008146594 A1 | | 12/2008 |
| WO | WO-2011118473 A1 | * | 9/2011 ........ A61F 13/51104 |
| WO | 201286730 A1 | | 6/2012 |
| WO | WO-2012086766 A1 | * | 6/2012 ............... D04H 1/54 |
| WO | 2013018846 A1 | | 2/2013 |
| WO | 2013084977 A1 | | 6/2013 |
| WO | 2013099625 A1 | | 7/2013 |
| WO | 2013145966 A1 | | 10/2013 |
| WO | WO-2014115401 A1 | * | 7/2014 ............. D04H 3/007 |
| WO | 2015146717 A1 | | 10/2015 |
| WO | 2017105997 A1 | | 6/2017 |
| WO | WO-2017110695 A1 | * | 6/2017 ............ A61F 13/511 |
| WO | WO-2018030181 A1 | * | 2/2018 ............ A61F 13/511 |
| WO | 2018144295 A1 | | 8/2018 |
| WO | WO-2018193775 A1 | * | 10/2018 ............ D04H 1/495 |

OTHER PUBLICATIONS

All Office Actions; U.S. Appl. No. 18/327,934, filed Jun. 2, 2023.
Unpublished U.S. Appl. No. 18/327,934, filed Jun. 2, 2023, to Arman Ashraf.
All Office Actions; U.S. Appl. No. 16/816,330, filed Mar. 12, 2020.
All Office Actions; U.S. Appl. No. 16/816,323, filed Mar. 12, 2020.
WO PCT Search Report and Written Opinion for PCT/US2020/022310 dated May 19, 2020, 13 pages.

* cited by examiner

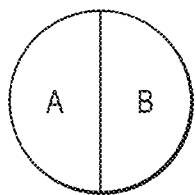 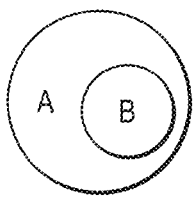 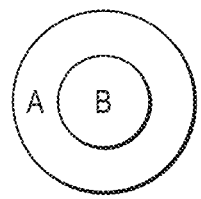
FIG. 5A  FIG. 5B  FIG. 5C
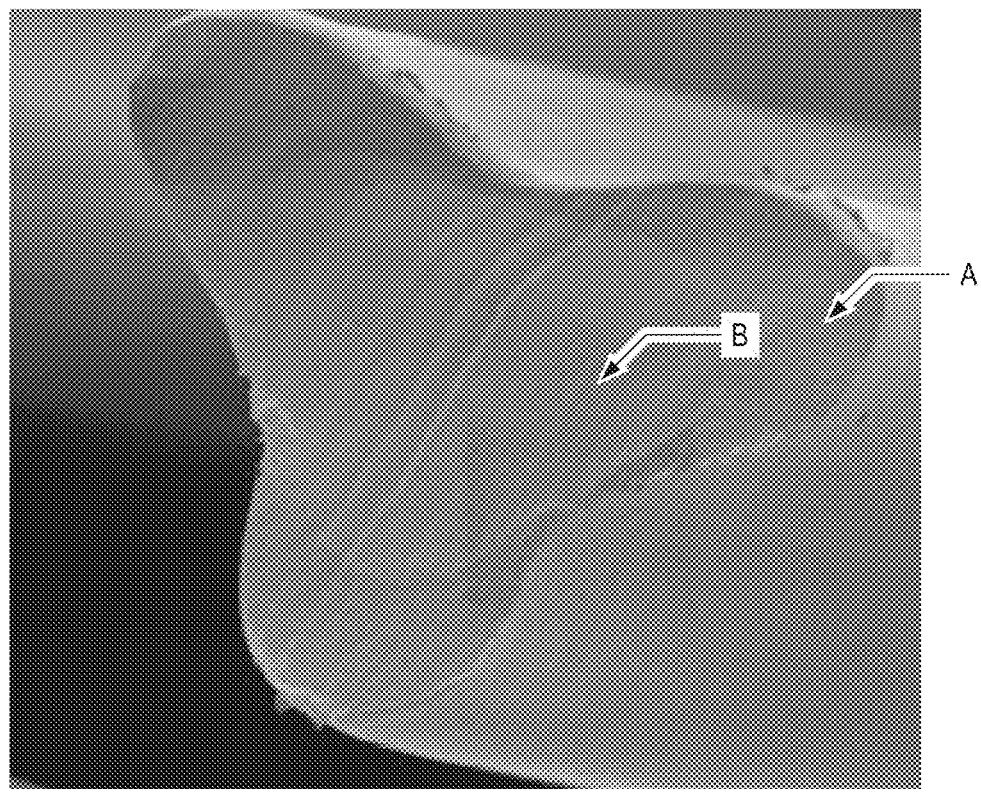
FIG. 6

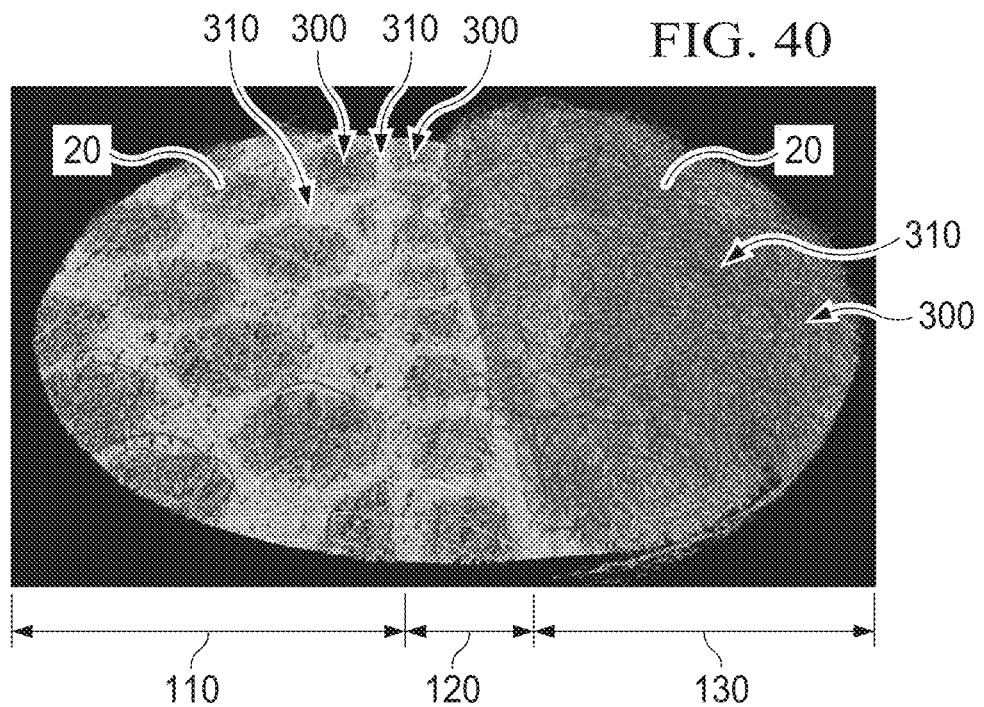
FIG. 40
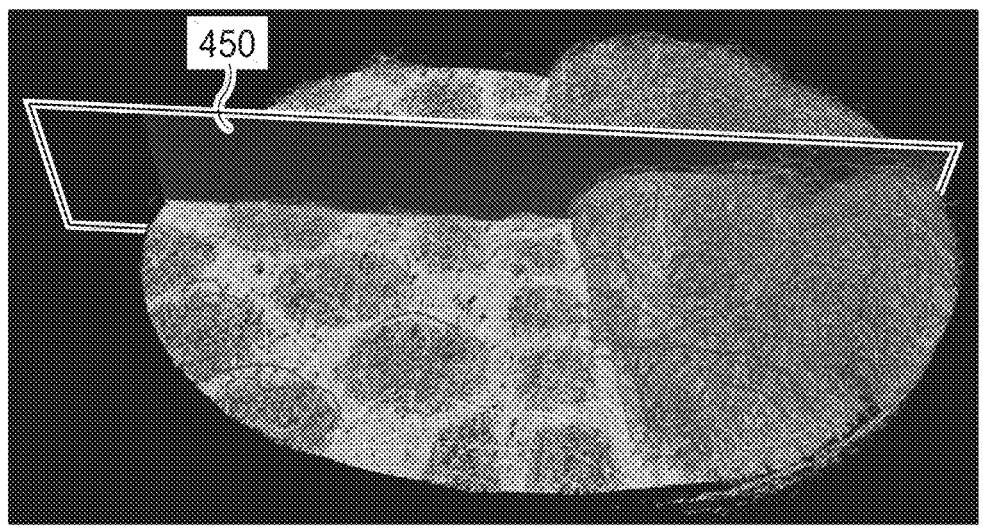
FIG. 41
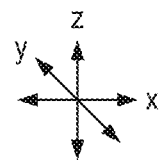

4 mm

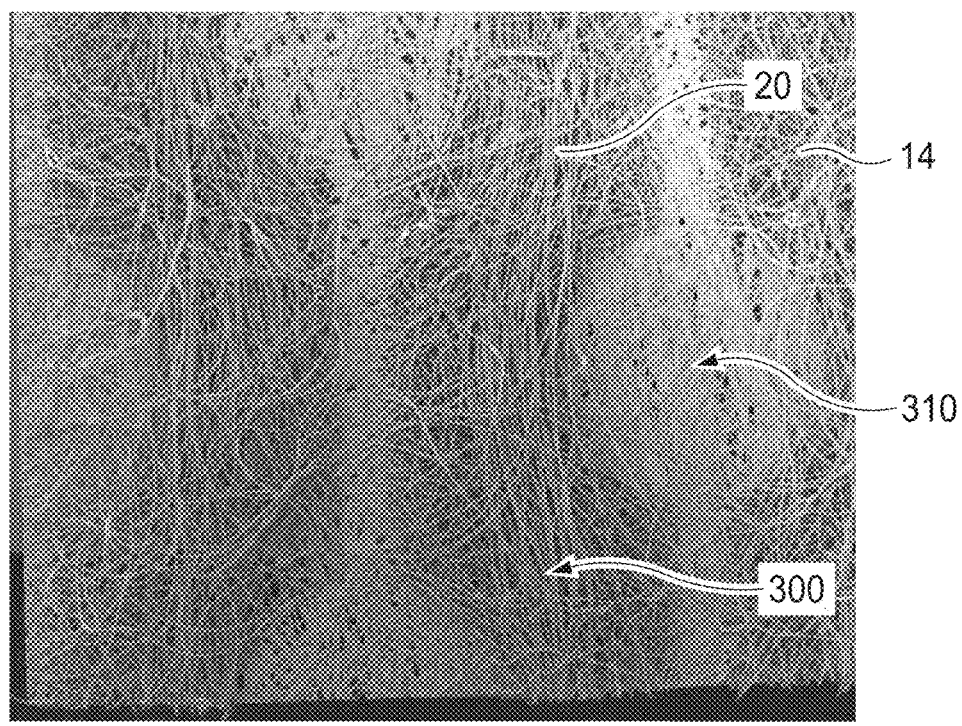
FIG. 45
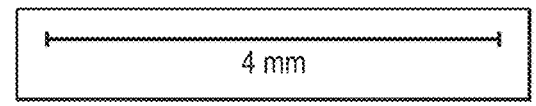
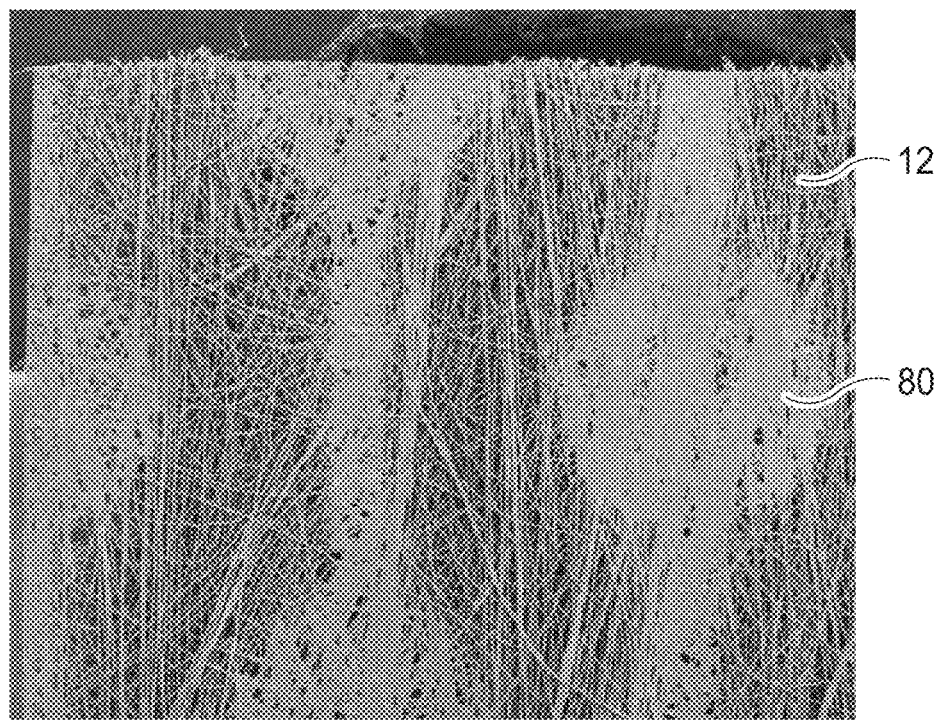
FIG. 46
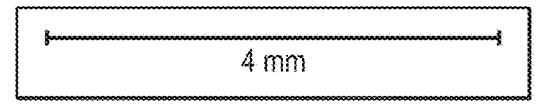

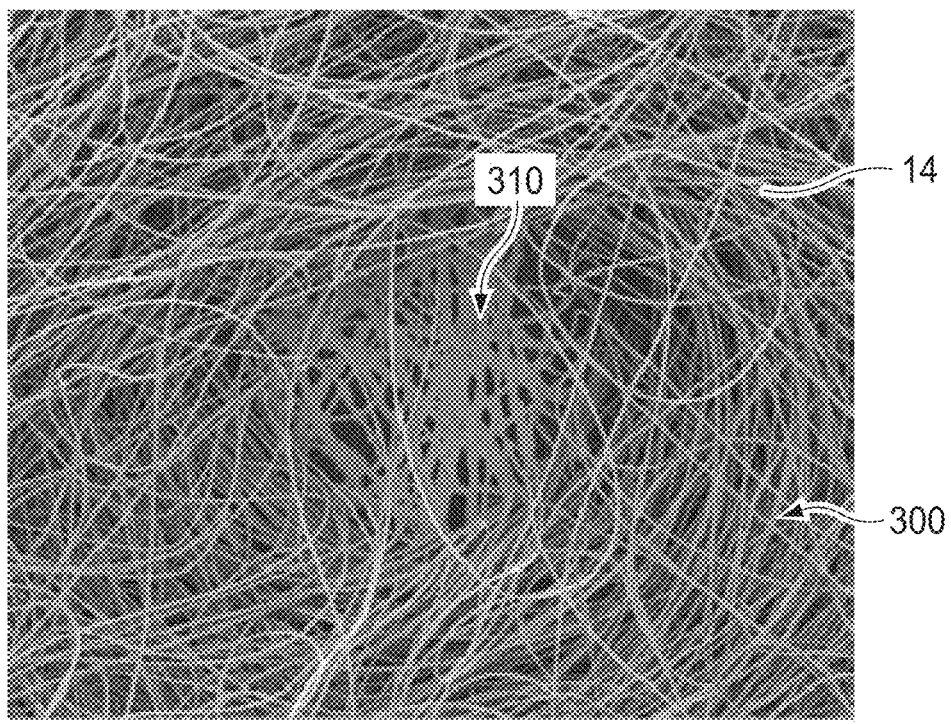
FIG. 51
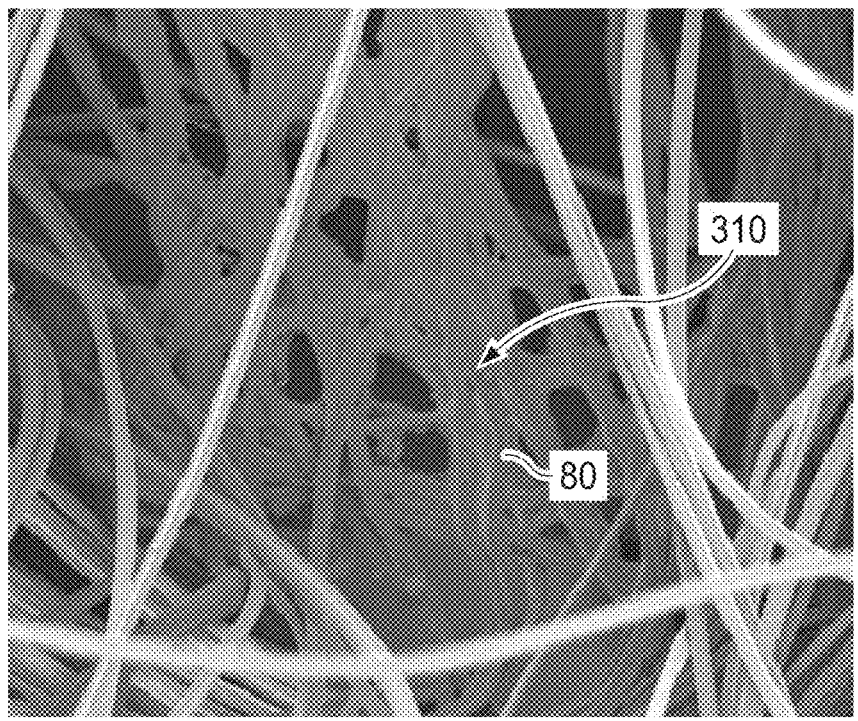
FIG. 52
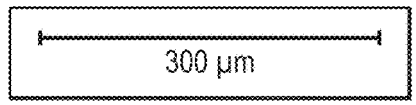

SHAPED NONWOVENS THAT EXHIBIT HIGH VISUAL RESOLUTION

CROSS REFERENCE TO RELATED APPLICATIONS

This application is a continuation of, and claims priority under 35 U.S.C. § 120 to, U.S. patent application Ser. No. 16/816,323, filed on Mar. 12, 2020, which claims the benefit, under 35 U.S.C. § 119(e), of U.S. Provisional Patent Application Ser. No. 62/819,729, filed on Mar. 18, 2019, the entire disclosures of which are incorporated herein by reference.

TECHNICAL FIELD

The present disclosure relates to shaped, three-dimensional nonwoven fabrics exhibiting high visual resolution, and articles made with shaped, three-dimensional nonwoven fabrics exhibiting high visual resolution.

BACKGROUND

Nonwoven fabrics are useful for a wide variety of applications, including absorbent personal care products, garments, medical applications, and cleaning applications. Nonwoven personal care products include infant care items such as diapers, childcare items such as training pants, feminine care items such as sanitary napkins, and adult care items such as incontinence products, pads, and pants. Nonwoven garments include protective workwear and medical apparel such as surgical gowns. Other nonwoven medical applications include nonwoven wound dressings and surgical dressings. Cleaning applications for nonwovens include towels and wipes.

The various properties of nonwoven fabrics may determine the suitability of a nonwoven fabric for a particular application. Accordingly, nonwoven fabrics may be engineered to have different combinations of properties to suit different needs. Variable properties of nonwoven fabrics include liquid-handling properties such as wettability, distribution, and absorbency; strength properties such as tensile strength and tear strength; softness properties; and durability properties such as abrasion resistance. The physical shape/pattern of a nonwoven fabric also affects the functionality and aesthetic appeal of a nonwoven fabric. Moreover, the aesthetics of a nonwoven fabric may be key in a consumer's preference for a consumer good that includes such nonwoven fabric, as nonwoven fabric aesthetics can communicate a product's value, quality, strength, softness, etc. One exemplary way to aesthetically communicate many of the commonly desirable traits in a patterned nonwoven is through a textured pattern that exhibits a high visual resolution (i.e., a visually sharp pattern). A visually sharp pattern provides the viewer with the perception of higher quality as such a nonwoven fabric pattern exhibits clean, well defined lines of textural contrast and not faded, fuzzy, or difficult to visually identify lines of textural contrast.

Despite prior advances in the art of nonwoven fabrics, there remains a need for improved nonwoven fabrics having visually discernable zones with three-dimensional surface features, wherein the visually discernable zones exhibit a high visual resolution.

Further, there remains a need for processes and equipment for manufacturing improved nonwoven fabrics having visually discernable zones with three-dimensional surface features, wherein the visually discernable zones exhibit a high visual resolution.

Further, there remains a need for articles, including absorbent articles, utilizing improved nonwoven fabrics having visually discernable zones with three-dimensional surface features, wherein the visually discernable zones exhibit a high visual resolution.

SUMMARY

A nonwoven fabric is disclosed. The nonwoven fabric can include a first surface and a second surface and at least a first visually discernible zone of three-dimensional features on one of the first or second surface. Each of the three-dimensional features can define a microzone comprising a first region and a second region. The first and second regions can have a difference in values for an intensive property, and the first visually discernible zone can exhibit a high visual resolution.

BRIEF DESCRIPTION OF THE DRAWINGS

FIG. 5A is a schematic drawing illustrating the cross-section of a filament made with a primary component A and a secondary component B in a side-by-side arrangement.

FIG. 5B is a schematic drawing illustrating the cross-section of a filament made with a primary component A and a secondary component B in an eccentric sheath/core arrangement.

FIG. 5C is a schematic drawing illustrating the cross-section of a filament made with a primary component A and a secondary component B in a concentric sheath/core arrangement.

FIG. 6 is a perspective view photograph of a tri-lobal, bicomponent fiber.

FIG. 40 is a Micro CT perspective view image of an example of a shaped nonwoven the present disclosure.

FIG. 41 is a Micro CT perspective view image of an example of a shaped nonwoven the present disclosure.

FIG. 45 is a photograph view image of a portion of an example of a shaped nonwoven the present disclosure.

FIG. 46 is a photograph view image of a portion of an example of a shaped nonwoven of the present disclosure.

FIG. 51 is a photograph view image of a portion of an example of a shaped nonwoven of the present disclosure.

FIG. 52 is a photograph view image of a portion of an example of a shaped nonwoven of the present disclosure.

DETAILED DESCRIPTION

The present disclosure provides a shaped nonwoven fabric directly formed on a shaped forming belt with continuous spunbond filaments in a single forming process. The fabric of the present disclosure can assume a shape which corresponds to the shape of the forming belt. A fabric of the present disclosure made on a forming belt of the present disclosure in a method of the present disclosure can be particularly beneficial for use in personal care articles, garments, medical products, and cleaning products. The shaped nonwoven fabric can be fluid permeable for use as a topsheet, backsheet nonwoven, acquisition layer, distribution layer, or other component layer for a diaper, or a topsheet, backsheet nonwoven, acquisition layer, distribution layer, or other component layer for a sanitary napkin, a topsheet, backsheet nonwoven, acquisition layer, distribution layer, or other component layer for an adult incontinent pad or pant, or a pad for a floor cleaning implement.

The beneficial features of the nonwoven fabric will be described in some embodiments herein in the context of an overall area of the nonwoven fabric. The overall area can be an area determined by dimensions suitable for certain uses, for which the various features of the invention provide beneficial properties. For example, the overall area of a fabric can be that of a fabric having dimensions making it suitable for use as a topsheet, backsheet nonwoven, acquisition layer, distribution layer, or other component layer for a diaper, or a topsheet, backsheet nonwoven, acquisition layer, distribution layer, or other component layer for a sanitary napkin, a topsheet, backsheet nonwoven, acquisition layer, distribution layer, or other component layer for an adult incontinent pad or pant, or a pad for a floor cleaning implement. Thus, the overall area can be based on width and length dimensions ranging from 3 cm wide to 50 cm wide and from 10 cm long to 100 cm long, resulting in overall areas of from 30 cm² to 500 cm². The aforementioned ranges include as if explicitly stated every integer dimension between the range boundaries. By way of example, an overall area of 176 cm² defined by a width of 11 cm and a length of 16 cm is disclosed in the above ranges. As will be understood from the description herein, the overall area of a shaped nonwoven fabric may be a smaller area than the area of the web of nonwoven material of which it is a part when it is commercially made. That is, in a given commercially made web of nonwoven material, there can be a plurality of shaped nonwoven fabrics of the invention, each of the shaped nonwoven fabrics of the invention having an overall area less than the area of the web on which it is made.

Figure 1:
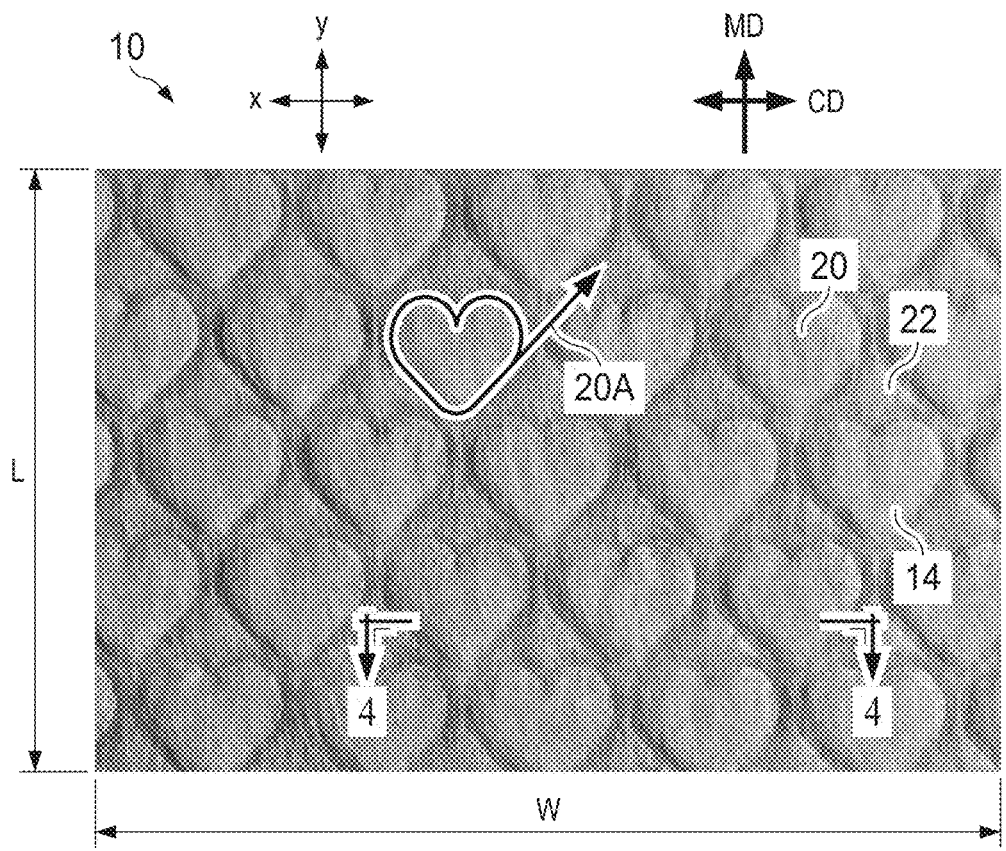
FIG. 1 is a photograph of an example of a shaped nonwoven of the present disclosure.
Figure 2:
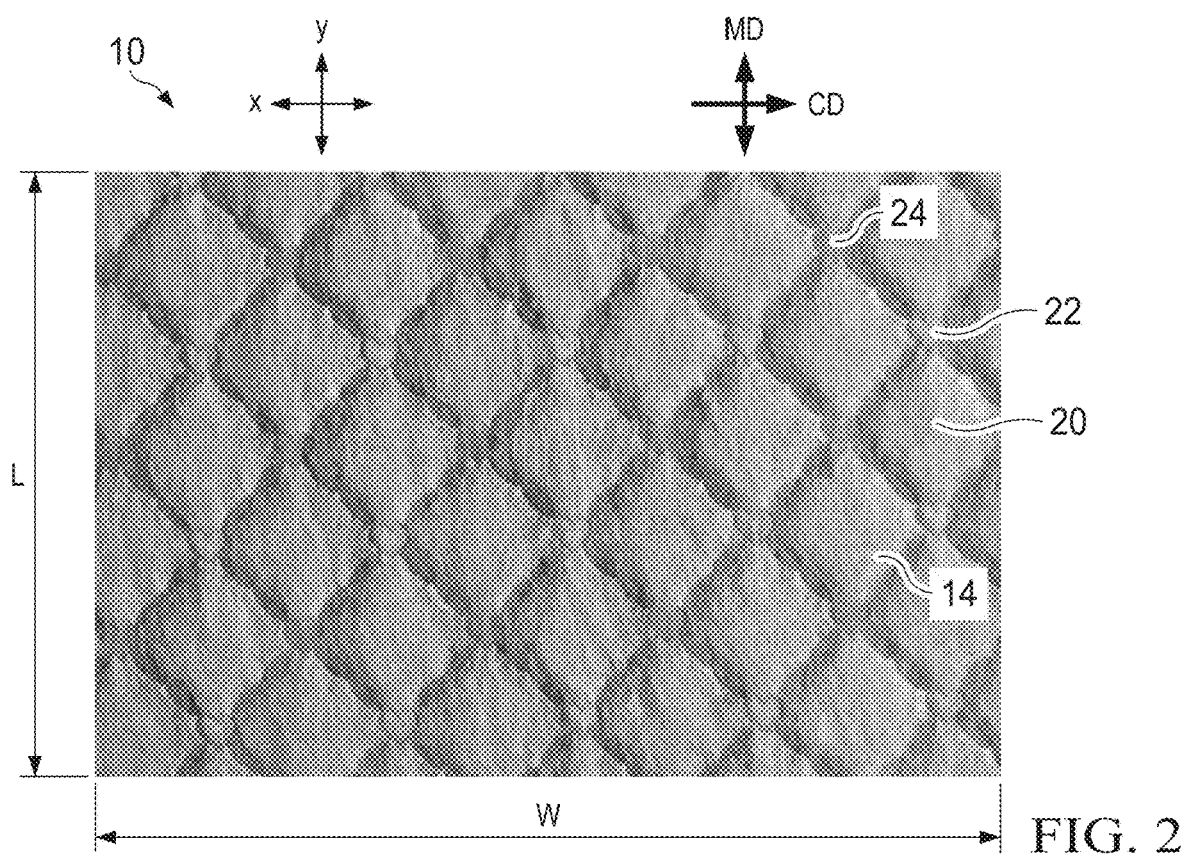
FIG. 2 is a photograph of an example of a shaped nonwoven of the present disclosure.
Figure 3:
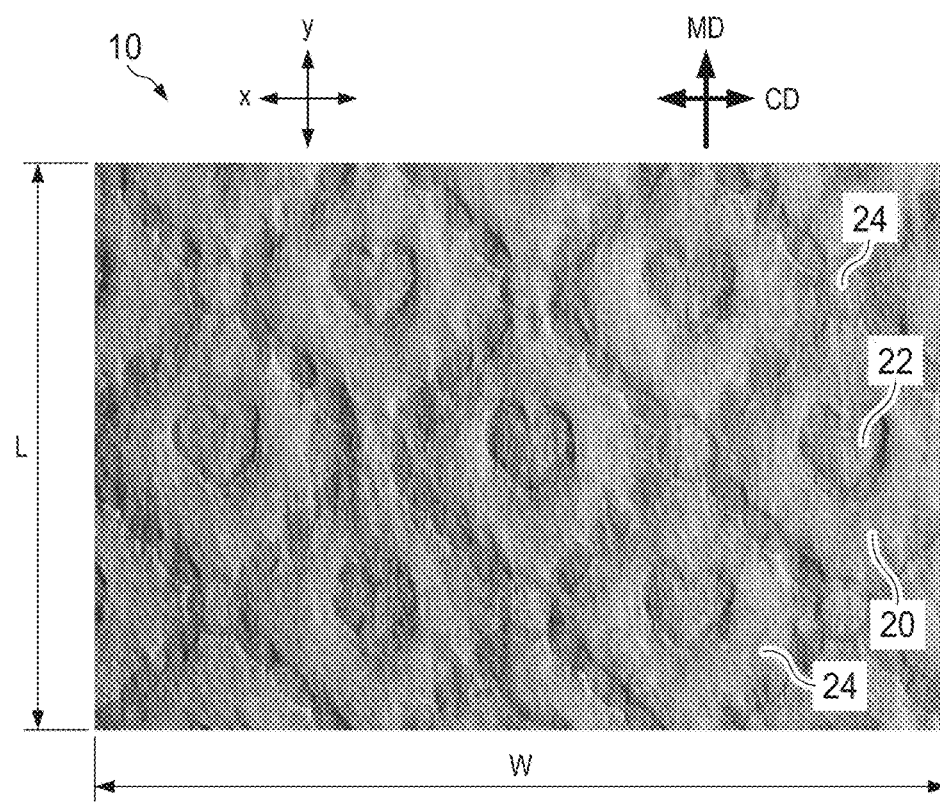
FIG. 3 is a photograph of an example of a shaped nonwoven of the present disclosure.
Figure 4:
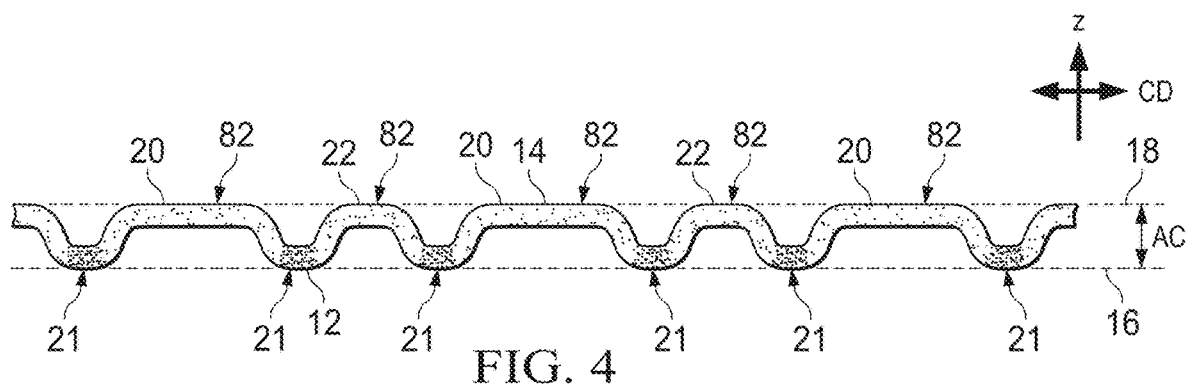
FIG. 4 is a cross-section of a portion of a fabric of the present disclosure as indicated in FIG. 1.

Photographs of representative examples of shaped nonwoven fabrics 10 are shown in FIGS. 1-3. The shaped nonwoven fabric 10 can be a spunbond nonwoven substrate having a first surface 12 and a second surface 14. In FIGS. 1-3, second surface 14 is facing the viewer and is opposite the first surface 12, which is unseen in FIGS. 1-3 but is depicted in FIG. 4. The term "surface" is used broadly to refer to the two sides of a web for descriptive purposes, and is not intended to infer any necessary flatness or smoothness. Although the shaped nonwoven fabric 10 is soft and flexible, it will be described in a flattened condition the context of one or more X-Y planes parallel to the flattened condition, and which correspond in web-making technology to the plane of the cross-machine direction, CD, and machine direction, MD, respectively, as shown in FIGS. 1-3. The length, L, in the MD and the width, W, in the CD determine the overall area A for the nonwoven fabric 10. As shown in FIG. 4, which is a cross section of a portion of the nonwoven fabric 10 shown in FIG. 1, for descriptive purposes the three-dimensional features of the shaped nonwoven fabric are described as extending outwardly in a Z-direction from an X-Y plane of the first surface 16 (see. FIG. 4). In an embodiment, a maximum dimension of three-dimensional features in the Z-direction can define the maximum distance between the plane of the first surface 16 and an X-Y plane of the second surface 18, which distance can be measured as the average caliper AC of the nonwoven fabric 10. The average caliper can be determined via optical, non-contact means, or it can be determined by instruments involving spaced apart flat plates that measure the caliper of the nonwoven placed between them under a predetermined pressure. It is not necessary that all the three-dimensional features have the same Z-direction maximum dimension, but a plurality of three-dimensional features can have substantially the same Z-direction maximum dimension determined by the fiber laydown process and the properties of the forming belt, discussed below.

The exemplary fabrics shown in FIGS. 1-4 (as well as other fabrics disclosed herein) are fluid permeable. In an embodiment the entire fabric can be considered fluid permeable. In an embodiment regions or zones (described below) can be fluid permeable. By fluid permeable as used herein with respect to the fabric is meant that the fabric has at least one zone which permits liquid to pass through under in-use conditions of a consumer product. For example, if used as a topsheet on a disposable diaper, the fabric can have at least one zone having a level of fluid permeability permitting urine, runny BM, menstrual fluid, or any other bodily exudate, to pass through to an underlying absorbent core. By fluid permeable as used herein with respect to a region is meant that the region exhibits a porous structure that permits liquid to pass through.

As shown in FIGS. 1-4, the nonwoven fabric 10 can have a regular, repeating pattern of a plurality of discrete, recognizably different three-dimensional features, including a first three-dimensional feature 20 and a second three-dimensional feature 22, and a third three-dimensional feature 24, as shown in FIGS. 2 and 3. For example, in FIG. 1, heart-shaped first three-dimensional feature 20 is recognizably different from the smaller, generally triangular-shaped second three-dimensional feature 22. The recognizable differences can be visual, such as recognizably different sizes and/or shapes.

The three-dimensional features of the nonwoven fabric 10 can be formed by depositing, such as by carding, air laying, spinning from solution, or melt spinning, fibers directly onto a forming belt having a pattern of corresponding three-dimensional features. In one sense the nonwoven fabric 10 is molded onto a forming belt that determines the shapes of the three-dimensional features of the fabric 10. However, importantly, as described herein, the apparatus and method of the invention produce the nonwoven fabric 10 such that in addition to taking the shape of the forming belt, because of the attributes of the forming belt and the apparatus for forming the fabric, it is imparted with beneficial properties for use in personal care articles, garments, medical products, and cleaning products. Specifically, because of the nature of the forming belt and other apparatus elements, as described below, the three-dimensional features of the nonwoven fabric 10 have intensive properties that can differ between first and second regions within a microzone (described more fully below), or from feature to feature in ways that provide for beneficial properties of the nonwoven fabric 10 when used in personal care articles, garments, medical products, and cleaning products. For example, first three-dimensional feature 20 can have a basis weight or density that is different from the basis weight or density of second three-dimensional feature 22, and both can have a basis weight or density that is different from that of third three-dimensional feature 24, providing for beneficial aesthetic and functional properties related to fluid acquisition, distribution and/or absorption in diapers or sanitary napkins.

The intensive property differential between the various three-dimensional features of nonwoven fabric 10 is believed to be due to the fiber distribution and compaction resulting from the apparatus and method described below. The fiber distribution occurs during the fiber laydown process, as opposed to, for example, a post making process such as hydroentangling or embossing processes. Because the fibers are free to move during a process such as a melt spinning process, with the movement determined by the nature of the features and air permeability of the forming belt and other processing parameters, the fibers are believed to be more stable and permanently formed in nonwoven fabric 10.

As can be seen in FIGS. 1-3 and as understood from the description herein, the distinct three-dimensional features may be bounded by visually discernible (with respect to the interior of a three-dimensional feature) regions that can be in the form of a closed figure (such as the heart shape in FIGS. 1 and 3, and the diamond shape of FIGS. 2 and 3). The closed figure can be a curvilinear closed figure such as the heart shape in FIGS. 1 and 3. The outlining visually discernible regions can be the regions of the nonwoven fabric 10 that are most closely adjacent in the Z-direction to first surface 12, such as regions 21 as shown in FIG. 4, and with can lie at least partially in or on first plane 16 when in a flattened condition. For example, as shown in FIG. 1, first three-dimensional feature 20 is heart shaped, and as indicated as one exemplary first three-dimensional feature 20A is defined by a curvilinear closed heart-shaped element. A curvilinear element can be understood as a linear element having at any point along its length a tangential vector V, with the closed shape being such that the tangential vector V has both MD and CD components that change values over greater than 50% of the length of the linear element of the closed figure. Of course, the figure need not be entirely 100% closed, but the linear element can have breaks that do not take away from the overall impression of a closed figure. As discussed below in the context of the forming belt, the outlining visually discernible curvilinear closed heart-shaped element is formed by a corresponding closed heart-shaped raised element on the forming belt to make the closed figure of a heart on fabric 10. In a repeating pattern, the individual shapes (in the case of first three-dimensional feature in FIG. 1, a heart shape) can result in aesthetically pleasing, soft, pillowy features across the overall area OA of the second surface 14 of fabric 10. In an embodiment in which the nonwoven fabric 10 is used as a topsheet for a diaper or sanitary napkin, the second surface 14 of nonwoven fabric 10 can be body-facing to deliver superior aesthetic and performance benefits related to softness, compression resistance, and fluid absorption.

Specifically, in the regular repeating pattern of closed, three-dimensional features shown in FIG. 1-3, it is believed, without being bound by theory, that the dimensions of the various features, the average basis weight of the entire fabric 10 across its overall area, and other processing parameters described below which define the differing intensive properties contribute to a beneficial improvement in compression recovery. It is believed that the plurality of relatively closely spaced, relatively small, and relatively pillowy three-dimensional features act as springs to resist compression and recover once a compressive force is removed. Compression recovery is important in topsheets, backsheet nonwovens, acquisition layers, distribution layers, or other component layers of personal care articles such as diapers, sanitary napkins, or adult incontinent pads, diapers, or pants for example, because such articles are typically packaged and folded in compressed conditions. Manufacturers of personal care products desire to retain most, if not all of the as-made caliper for aesthetic and performance purposes. The three-dimensionality of formed features provide important aesthetic benefits due to the look and feel of softness and pleasing appearance of crisp, well-defined shapes, including very small shapes such as the small hearts shown in FIG. 2. The three-dimensional features also provide for softness during use, improved absorbency, less leakage, and overall improved in-use experience. But the necessary compression during folding, packaging, shipping and storing of the personal care articles can cause permanent loss of caliper of a topsheet, backsheet nonwovens, acquisition layers, distribution layers, or other component layers of the absorbent article thereby degrading the as-made functional benefits. The nonwoven fabrics of the present disclosure retain to a significant degree their as made three-dimensional features even after undergoing compression packaging and distribution in a compression packaged state.

Table 1 below shows compression recovery data for two embodiments of the present disclosure. Example 1 corresponds to the nonwoven fabric 10 shown in FIG. 1 and made on a forming belt as described with reference to FIGS. 12 and 14. Example 2 corresponds to the nonwoven fabric 10 shown in FIG. 2 and made on a forming belt as described with reference to FIGS. 15 and 16. As can be seen from the data, the fabrics 10 of the invention show a significant benefit with respect to compression recovery when measured by the Compression Aging Test. In a form, packages of the absorbent articles having the compression recovery characteristics of the present disclosure can have a reduced in-bag stack height yet still deliver the aesthetic, absorbency, and softness benefits of the as made diaper; or as if it were never compression packaged. This invention provides for reduced in-bag stack height packages which allow caregivers to easily handle and store the packages while also providing manufacturers with reduced distribution costs, both achieved while maintaining as made aesthetics clarity, absorbency, or softness performance of the absorbent article.

Example 1

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration, as shown in FIG. 6, which is a scanning electron micrograph (SEM) showing a cross section of a bicomponent trilobal fiber. The nonwoven fabric was spun on a forming belt having a repeating pattern as described in FIG. 12 as described below with respect to FIGS. 7 and 8 moving at a linear speed of about 25 meters per minute to an average basis weight of 30 grams per square meter with a repeating pattern of heart shapes as shown in FIG. 1. Fibers of the fabric were further bonded on first side 12 by heated compaction rolls 70, 72 (described below) at 130° C. and being wound on to a reel at winder 75.

Example 2

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration, as shown in FIG. 6, which is a scanning electron micrograph showing a cross section of a bicomponent trilobal fiber. The nonwoven fabric was spun on a forming belt having a repeating pattern as described in FIG. 16 as described below with respect to FIGS. 7 and 8 moving at a linear speed of about 25 meters per minute to form a fabric 10 having an average basis weight of 30 grams per square meter with a repeating pattern of diamond shapes as shown in FIG. 2. Fibers of the fabric were further bonded on first surface 12 by heated compaction rolls 70, 72 (described below) at 130° C.

TABLE 1

| | Fresh (Nonwoven off the roll) Caliper | 4 KPa (~96 mm IBSH) | | 14 KPa (~84 mm IBSH) | | 35 KPa (~68 mm IBSH) | |
|---|---|---|---|---|---|---|---|
| 3-D Nonwoven | | Caliper after Compression | Percent Caliper Retention (%) | Caliper after Compression | Percent Caliper Retention (%) | Caliper after Compression | Percent Caliper Retention (%) |
| Example 1 | 0.45 | 0.38 | 84.44 | 0.35 | 77.78 | 0.34 | 75.56 |
| Example 2 | 0.43 | 0.36 | 83.72 | 0.36 | 83.72 | 0.31 | 72.09 |

As can be seen from Table 1, fabrics 10 of the invention retain significant amounts of caliper after compression at relatively high pressures. For example, the Example 1 and Example 2 samples retain greater than 70% of their original average caliper after being tested by the Compression Aging Test at a pressure of 35 KPa. The Compression Aging Test is a simulation of the conditions a nonwoven fabric would encounter if packaged in a high compression packaging of diapers and then remain in such a state during distribution to a consumer and then the package finally opened by a consumer.

The present disclosure can utilize the process of melt spinning. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Melt spinning can occur at from about 150° C. to about 280°, or, in some embodiments, at from about 190° to about 230°. Fiber spinning speeds can be greater than 100 meters/minute, and can be from about 1.000 to about 10,000 meters/minute, and can be from about 2,000 to about 7,000 meters/minute, and can be from about 2,500 to about 5,000 meters/minute. Spinning speeds can affect the brittleness of the spun fiber, and, in general, the higher the spinning speed, the less brittle the fiber. Continuous fibers can be produced through spunbond methods or meltblowing processes.

A nonwoven fabric 10 of the present disclosure can include continuous multicomponent polymeric filaments comprising a primary polymeric component and a secondary polymeric component. The filaments can be continuous bicomponent filaments comprising a primary polymeric component A and a secondary polymeric component B. The bicomponent filaments have a cross-section, a length, and a peripheral surface. The components A and B can be arranged in substantially distinct zones across the cross-section of the bicomponent filaments and can extend continuously along the length of the bicomponent filaments. The secondary component B constitutes at least a portion of the peripheral surface of the bicomponent filaments continuously along the length of the bicomponent filaments. The polymeric components A and B can be melt spun into multicomponent fibers on conventional melt spinning equipment. The equipment will be chosen based on the desired configuration of the multicomponent. Commercially available melt spinning equipment is available from Hills, Inc. located in Melbourne, Florida. The temperature for spinning range from about 180° C. to about 230° C. The processing temperature is determined by the chemical nature, molecular weights and concentration of each component. The bicomponent spunbond filaments can have an average diameter from about 6 to about 40 microns, and preferably from about 12 to about 40 microns.

The components A and B can be arranged in either a side-by-side arrangement as shown in FIG. 5A or an eccentric sheath/core arrangement as shown in FIG. 5B to obtain filaments which exhibit a natural helical crimp. Alternatively, the components A and B can be arranged in a concentric sheath core arrangement as shown in FIG. 5C. Additionally, the component A and B can be arranged in multi-lobal sheath core arrangement as shown in FIG. 6. Other multicomponent fibers can be produced by using the compositions and methods of the present disclosure. The bicomponent and multicomponent fibers may be segmented pie, ribbon, islands-in-the-sea configuration, or any combination thereof. The sheath may be continuous or non-continuous around the core. The ratio of the weight of the sheath to the core is from about 5:95 to about 95:5. The fibers of the present disclosure may have different geometries that include round, elliptical, star shaped, rectangular, and other various eccentricities.

Methods for extruding multicomponent polymeric filaments into such arrangements are well-known to those of ordinary skill in the art.

A wide variety of polymers are suitable to practice the present disclosure including polyolefins (such as polyethylene, polypropylene and polybutylene), polyesters, polyamides, polyurethanes, elastomeric materials and the like. Non-limiting examples of polymer materials that can be spun into filaments include natural polymers, such as starch, starch derivatives, cellulose and cellulose derivatives, hemicellulose, hemicelluloses derivatives, chitin, chitosan, polyisoprene (cis and trans), peptides, polyhydroxyalkanoates, and synthetic polymers including, but not limited to, thermoplastic polymers, such as polyesters, nylons, polyolefins such as polypropylene, polyethylene, polyvinyl alcohol and polyvinyl alcohol derivatives, sodium polyacrylate (absorbent gel material), and copolymers of polyolefins such as polyethylene-octene or polymers comprising monomeric blends of propylene and ethylene, and biodegradable or compostable thermoplastic polymers such as polylactic acid filaments, polyvinyl alcohol, filaments, and polycaprolactone filaments. In one example, thermoplastic polymer selected from the group consisting of: polypropylene, polyethylene, polyester, polylactic acid, polyhydroxyalkanoate, polyvinyl alcohol, polycaprolactone, styrene-butadiene-styrene block copolymer, styrene-isoprene-styrene block copolymer, polyurethane, and mixtures thereof. In another example, the thermoplastic polymer is selected from the group consisting of: polypropylene, polyethylene, polyester, polylactic acid, polyhydroxyalkanoate, polyvinyl alcohol, polycaprolactone, and mixtures thereof. Alternatively, the polymer can comprise one derived from monomers which are biobased such as bio-polyethylene or bio-polypropylene.

Primary component A and secondary component B can be selected so that the resulting bicomponent filament is providing improved nonwoven bonding and substrate softness.

Primary polymer component A has melting temperature which is lower than the melting temperature of secondary polymer component B.

Primary polymer component A can comprise polyethylene or random copolymer of propylene and ethylene. Secondary polymer component B can comprise polypropylene or random copolymer of propylene and ethylene. Polyethylenes include linear low density polyethylene and high density polyethylene. In addition, secondary polymer component B may comprise additives for enhancing the natural helical crimp of the filaments, lowering the bonding temperature of the filaments, and enhancing the abrasion resistance, strength and softness of the resulting fabric.

Inorganic fillers such as the oxides of magnesium, aluminum, silicon, and titanium may be added as inexpensive fillers or processing aides. Other inorganic materials include hydrous magnesium silicate, titanium dioxide, calcium carbonate, clay, chalk, boron nitride, limestone, diatomaceous earth, mica glass quartz, and ceramics.

The filaments of the present invention also contain a slip additive in an amount sufficient to impart the desired haptics to the fiber. As used herein "slip additive" or "slip agent" means an external lubricant. The slip agent when melt-blended with the resin gradually exudes or migrates to the surface during cooling or after fabrication, hence forming a uniform, invisibly thin coating thereby yielding permanent lubricating effects. The slip agent is preferably a fast bloom slip agent, and can be a hydrocarbon having one or more functional groups selected from hydroxide, aryls and substituted aryls, halogens, alkoxys, carboxylates, esters, carbon unsaturation, acrylates, oxygen, nitrogen, carboxyl, sulfate and phosphate.

During the making or in a post-treatment or even in both, the nonwoven fabrics of the present invention can be treated with surfactants or other agents to either hydrophilize the web or make it hydrophobic. This is standard practice for nonwovens used in absorbent articles. For example, a nonwoven fabric used for a topsheet may be treated with a hydrophilizing material or surfactant so as to make it permeable to body exudates such as urine. For other absorbent articles, the topsheet may remain at its naturally hydrophobic state or made even more hydrophobic through the addition of a hydrophobizing material or surfactant.

Suitable materials for preparing the multicomponent filaments of the fabric of the present disclosure include PH-835 polypropylene obtained from LyondellBasell and Aspun-6850-A polyethylene obtained from Dow chemical company.

When polyethylene is component A (sheath) and polypropylene is component B (core), the bicomponent filaments may comprise from about 5 to about 95% by weight polyethylene and from about 95 to about 5% polypropylene. The filaments can comprise from about 40 to about 60% by weight polyethylene and from about 60 to about 40% by weight polypropylene.

Figure 7:
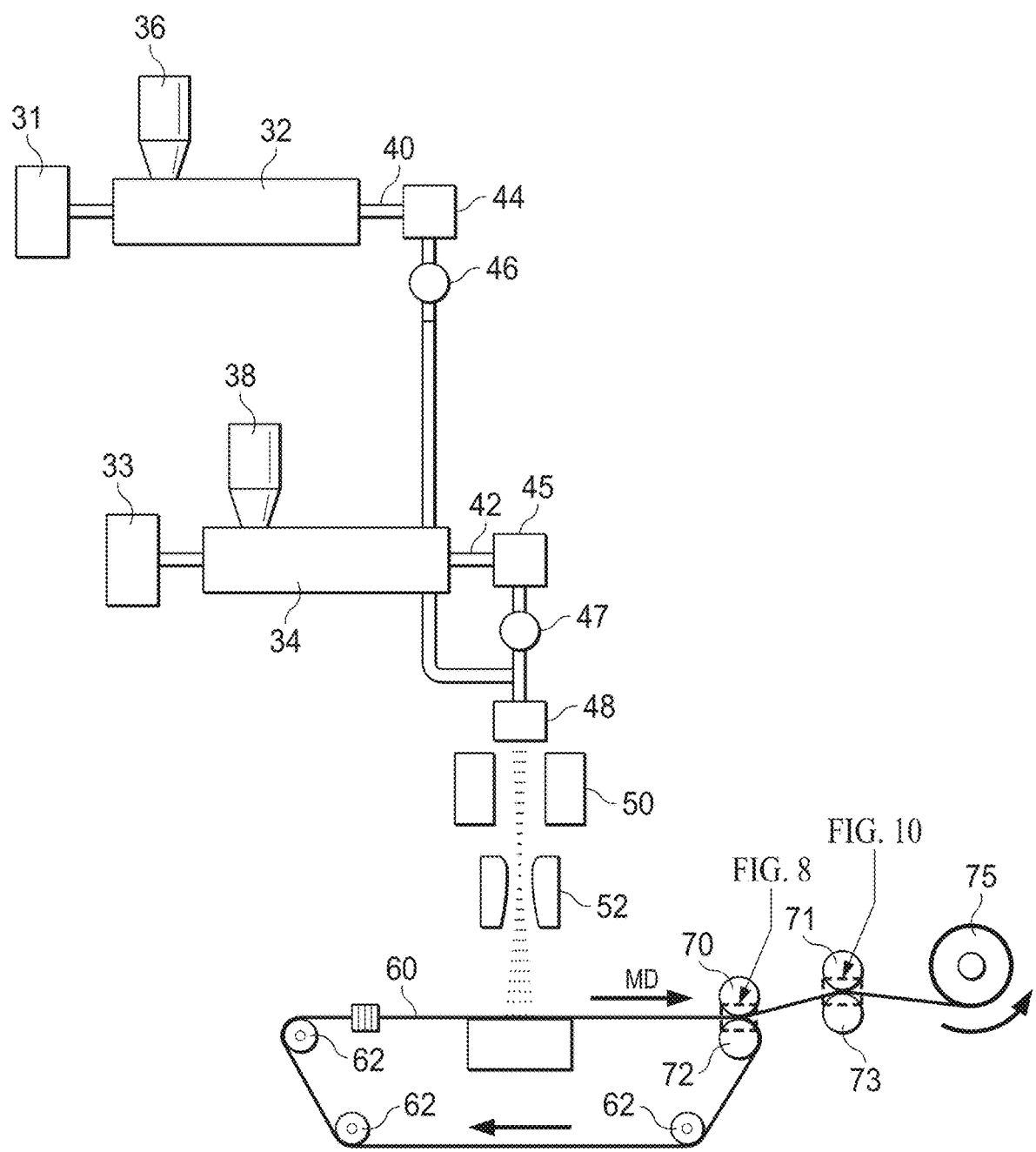
FIG. 7 is a schematic representation of an apparatus for making a fabric of the present disclosure.

Turning to FIG. 7, a representative process line 30 for preparing fabrics 10 of the present disclosure is disclosed. The process line 30 is arranged to produce a fabric of bicomponent continuous filaments, but it should be understood that the present disclosure comprehends nonwoven fabrics made with monocomponent or multicomponent filaments having more than two components. Bicomponent filaments may be trilobal.

The process line 30 includes a pair of extruders 32 and 34 driven by extruder drives 31 and 33, respectively, for separately extruding the primary polymer component A and the secondary polymer component B. Polymer component A is fed into the respective extruder 32 from a first hopper 36 and polymer component B is fed into the respective extruder 34 from a second hopper 38. Polymer components A and B can be fed from the extruders 32 and 34 through respective polymer conduits 40 and 42 to filters 44 and 45 and melt pumps 46 and 47, which pump the polymer into a spin pack 48. Spinnerets for extruding bicomponent filaments are well-known to those of ordinary skill in the art and thus are not described here in detail.

Generally described, the spin pack 48 includes a housing which includes a plurality of plates stacked one on top of the other with a pattern of openings arranged to create flow paths for directing polymer components A and B separately through the spinneret. The spin pack 48 has openings arranged in one or more rows. The spinneret openings form a downwardly extending curtain of filaments when the polymers are extruded through the spinneret. For the purposes of the present disclosure, spinnerets may be arranged to form sheath/core or side-by-side bicomponent filaments illustrated in FIGS. 5A, 5B, and 5C, as well as non-round fibers, such as tri-lobal fibers as shown in FIG. 6. Moreover, the fibers may be monocomponent comprising one polymeric component such as polypropylene.

The process line 30 also includes a quench blower 50 positioned adjacent the curtain of filaments extending from the spinneret. Air from the quench air blower 50 quenches the filaments extending from the spinneret. The quench air can be directed from one side of the filament curtain or both sides of the filament curtain.

An attenuator 52 is positioned below the spinneret and receives the quenched filaments. Fiber draw units or aspirators for use as attenuators in melt spinning polymers are well-known. Suitable fiber draw units for use in the process of the present disclosure include a linear fiber attenuator of the type shown in U.S. Pat. No. 3,802,817 and educative guns of the type shown in U.S. Pat. Nos. 3,692,618 and 3,423,266, the disclosures of which are incorporated herein by reference.

Generally described, the attenuator 52 includes an elongate vertical passage through which the filaments are drawn by aspirating air entering from the sides of the passage and flowing downwardly through the passage. A shaped, endless, at least partially foraminous, forming belt 60 is positioned below the attenuator 52 and receives the continuous filaments from the outlet opening of the attenuator 52. The forming belt 60 is a belt and travels around guide rollers 62. A vacuum 64 positioned below the forming belt 60 where the filaments are deposited draws the filaments against the forming surface. Although the forming belt 60 is shown as a belt in FIG. 8, it should be understood that the forming belt can also be in other forms such as a drum. Details of particular shaped forming belts are explained below.

In operation of the process line 30, the hoppers 36 and 38 are filled with the respective polymer components A and B. Polymer components A and B are melted and extruded by the respective extruders 32 and 34 through polymer conduits 40 and 42 and the spin pack 48. Although the temperatures of the molten polymers vary depending on the polymers used, when polyethylene and polypropylene are used as primary component A and secondary component B respectively, the temperatures of the polymers can range from about 190° C. to about 240° C.

As the extruded filaments extend below the spinneret, a stream of air from the quench blower 50 at least partially quenches the filaments, and, for certain filaments, to induce crystallization of molten filaments. The quench air can flow in a direction substantially perpendicular to the length of the filaments at a temperature of about 0° C. to about 35° C. and a velocity from about 100 to about 400 feet per minute. The filaments can be quenched sufficiently before being collected on the forming belt 60 so that the filaments can be arranged by the forced air passing through the filaments and forming surface. Quenching the filaments reduces the tackiness of the filaments so that the filaments do not adhere to one another too tightly before being bonded and can be moved or arranged on the forming belt during collection of the filaments on the forming belt and formation of the web.

After quenching, the filaments are drawn into the vertical passage of the attenuator 52 by a flow of the fiber draw unit. The attenuator can be positioned 30 to 60 inches below the bottom of the spinneret.

The filaments can be deposited through the outlet opening of the attenuator 52 onto the shaped, traveling forming belt 60. As the filaments are contacting the forming surface of the forming belt 60, the vacuum 64 draws the air and filaments against the forming belt 60 to form a nonwoven web of continuous filaments which assumes a shape corresponding to the shape of the forming surface. As discussed above, because the filaments are quenched, the filaments are not too tacky and the vacuum can move or arrange the filaments on the forming belt 60 as the filaments are being collected on the forming belt 60 and formed into the fabric 10.

The process line 30 further includes one or more bonding devices such as the cylinder-shaped compaction rolls 70 and 72, which form a nip through which the fabric can be compacted. i.e., calendared, and which can be heated to bond fibers as well. One or both of compaction rolls 70, 72 can be heated to provide enhanced properties and benefits to the nonwoven fabric 10 by bonding portions of the fabric. For example, it is believed that heating sufficient to provide thermal bonding improves the fabric's 10 tensile properties. The compaction rolls may be pair of smooth surface stainless steel rolls with independent heating controllers. The compaction rolls may be heated by electric elements or hot oil circulation. The gap between the compaction rolls can be hydraulically controlled to impose desired pressure on the fabric as it passes through the compaction rolls on the forming belt. In an embodiment, with a forming belt caliper of 1.4 mm, and a spunbond nonwoven having a basis weight of 30 gsm, the nip gap between the compaction rolls 70 and 72 can be about 1.4 mm.

Figure 8:
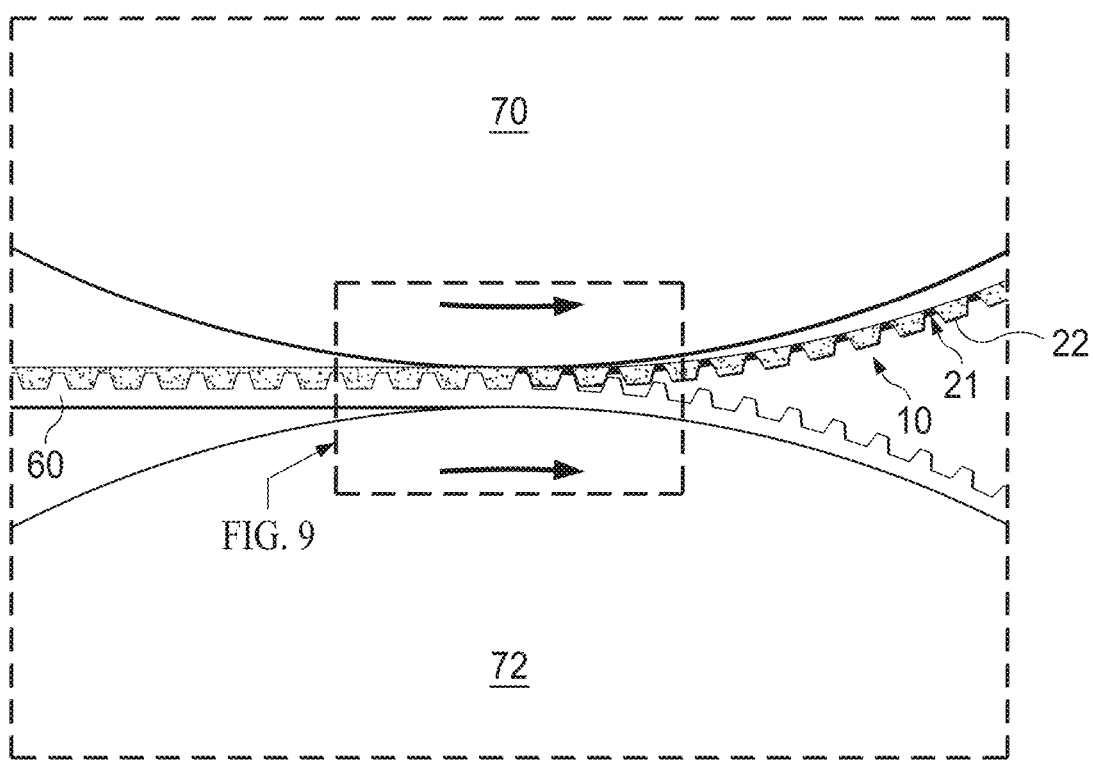
FIG. 8 is a detail of a portion of the apparatus for bonding a portion of a fabric of the present disclosure.
Figure 9:
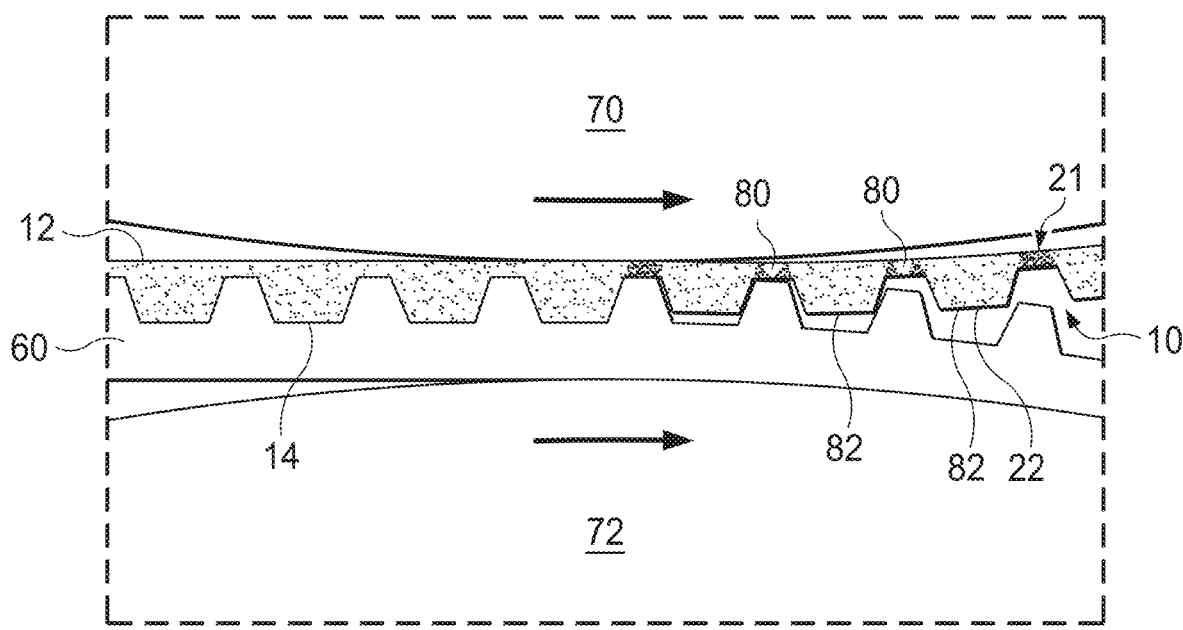
FIG. 9 is a further detail of a portion of the apparatus for bonding a portion of a fabric of the present disclosure.
Figure 11:
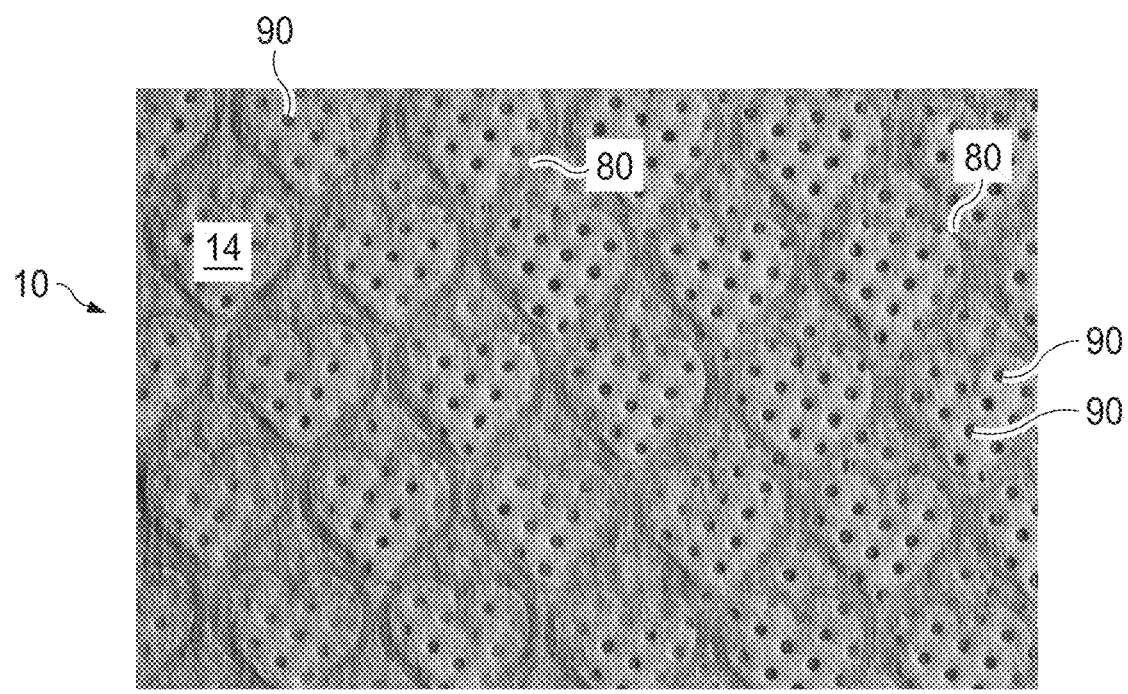
FIG. 11 is a photograph of an example of the present disclosure.

In an embodiment, upper compaction roll 70 can be heated sufficient to melt bond fibers on the first surface 12 of the fabric 10, to impart strength to the fabric so that it can be removed from forming belt 60 without losing integrity. As shown in FIGS. 8 and 9, for example, as rolls 70 and 72 rotate in the direction indicated by the arrows, belt 60 with the spunbond fabric laid down on it enter the nip formed by rolls 70 and 72. Heated roll 70 can heat the portions of nonwoven fabric 10 that are pressed against it by the raised resin elements of belt 60, i.e., in regions 21, to create bonded fibers 80 on at least first surface 12 of fabric 10. As can be understood by the description herein, the bonded regions so formed can take the pattern of the raised elements of forming belt 60. For example, the bonded areas so formed can be a substantially continuous network or a substantially semi-continuous network on first surface 12 of regions 21 that make the same pattern as the hearts of FIG. 1 and FIG. 11. By adjusting temperature and dwell time, the bonding can be limited primarily to fibers closest to first surface 12, or thermal bonding can be achieved to second surface 14 as shown in FIG. 11 (which also shows point bonds 90, discussed more fully below), and FIGS. 45-49. Bonding can also be a discontinuous network, for example, as point bonds 90, discussed below.

The raised elements of the forming belt 60 may be selected to establish various network characteristics of the forming belt and the bonded regions of the nonwoven substrate 11 or nonwoven fabric 10. The network corresponds to the resin making up the raised elements of the forming belt 60 and may comprise substantially continuous, substantially semi-continuous, discontinuous, or combinations thereof options. These networks may be descriptive of the raised elements of the forming belt 60 as it pertains to their appearance or make-up in the X-Y planes of the forming belt 60 or the three dimensional features comprising the nonwoven substrate 11 or nonwoven fabric 10 of the present invention.

"Substantially continuous" network refers to an area within which one can connect any two points by an uninterrupted line running entirely within that area throughout the line's length. That is, the substantially continuous network has a substantial "continuity" in all directions parallel to the first plane and is terminated only at edges of that region. The term "substantially." in conjunction with continuous, is intended to indicate that while an absolute continuity can be achieved, minor deviations from the absolute continuity may be tolerable as long as those deviations do not appreciably affect the performance of the fibrous structure (or a molding member) as designed and intended.

"Substantially semi-continuous" network refers an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is preferred, minor deviations from such a continuity may be tolerable as long as those deviations do not appreciably affect the performance of the fibrous structure.

"Discontinuous" network refer to discrete, and separated from one another areas that are discontinuous in all directions parallel to the first plane.

Figure 10:
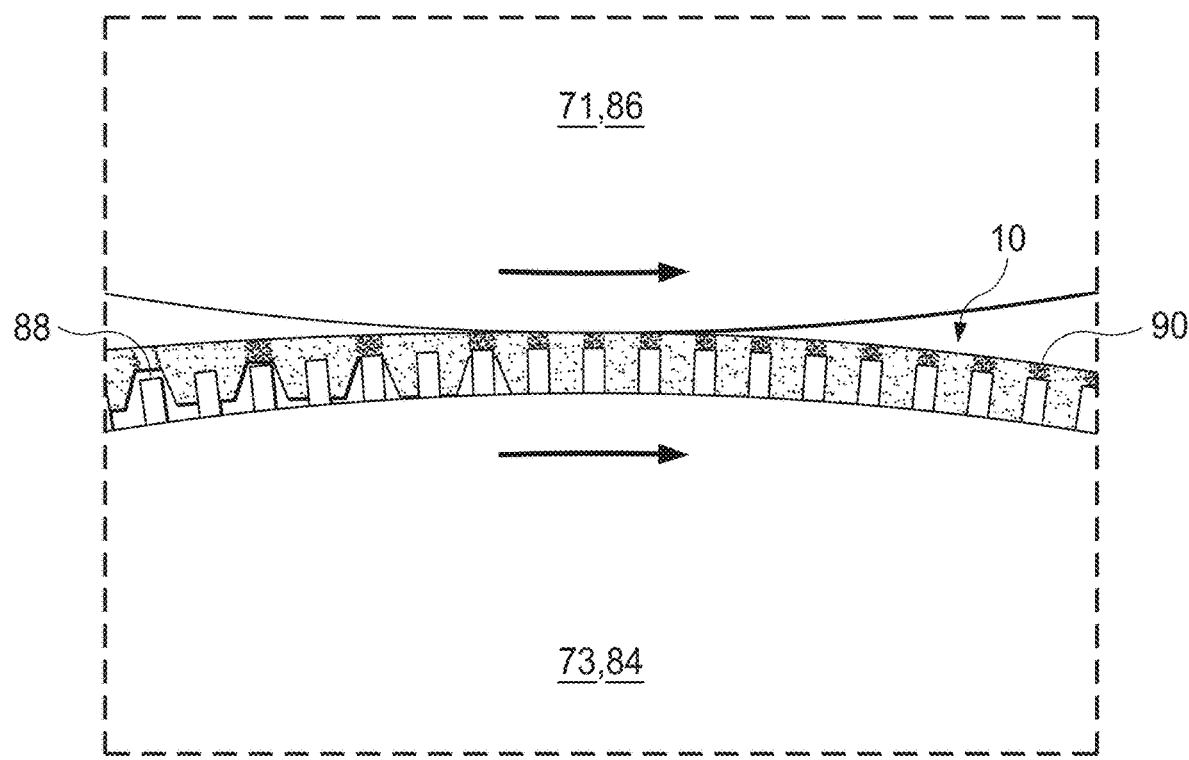
FIG. 10 is a detail of a portion of the apparatus for optional additional bonding of a portion of a fabric of the present disclosure.

After compaction, the fabric can leave the forming belt 60 and be calendared through a nip formed by calendar rolls 71, 73, after which the fabric can be wound onto a reel. As shown in the schematic cross section of FIG. 10, the calendar rolls can be stainless steel rolls having an engraved pattern roll 84 and a smooth roll 86. The engraved roll can have raised portions 88 that can provide for additional compaction and bonding to the fabric 10. Raised portions 88 can be a regular pattern of relatively small spaced apart "pins" that form a pattern of relatively small point bonds 90 in the nip of calendar rolls 71 and 73. The percent of point bonds in the nonwoven fabric 10 can be from 3% to 30% or from 7% to 20%. The engraved pattern can be a plurality of closely spaced, regular, generally cylindrically-shaped, generally flat-topped pin shapes, with pin heights being in a range from ranging 0.5 mm to 5 mm and preferably from 1 mm to 3 mm. Pin bonding calendar rolls can form closely spaced, regular point bonds 90 in nonwoven fabric 10, as shown in FIG. 11. Further bonding can be by hot-air through bonding, for example.

As described with respect to FIG. 56 below, through-air thermal bonding may be another approach to create higher loft nonwoven structures which may be suitable for this application. Through-air thermal bonding involves the application of hot air to the surface of the nonwoven fabric. The hot air flows through holes in a plenum positioned just above the nonwoven. However, the air is not pushed through the nonwoven, as in common hot air ovens. Negative pressure or suction pulls the air through the open conveyor apron that supports the nonwoven as it passes thorough the oven. Pulling the air through the nonwoven fabric allows much more rapid and even transmission of heat and minimizes fabric distortion. Aside from conventional through air bonding units, one could envision placing the bonding unit on top of the 3D belt while a vacuum is set under the belt to mimic the process of through air bonding for this specific application.

Binders used in through-air thermal bonding include crystalline binder fibers, bicomponent binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. In one embodiment, a nonwoven comprising sheath/core binder fibers, the sheath comprises a polyethylene and the core comprises polypropylene. For such a nonwoven, the through-air thermal bonding air temperature may be in the range of 110° C. to 150° C. and the residence time may be in the range of 0.5 to 10 seconds, 5-30 seconds, or 30-60 seconds as through air bonding time will depend upon basis weight, level of strength desired, and operating speed. Products manufactured using through-air ovens tend to be bulky, open, soft, strong, extensible, breathable and absorbent.

Point bonding as used herein is a method of thermally bonding a nonwoven fabric, web, or substrate. This method involves passing a web through a nip between two rolls consisting of heated male patterned or engraved metal roll and a smooth or patterned metal roll. The male patterned roll can have a plurality of raised, generally cylindrical-shaped pins that produce circular point bonds. The smooth roll may or may not be heated, depending on the application. In a nonwoven production line, the nonwoven fabric, which could be a non-bonded fiber web, is fed into the calendar nip and the fiber temperature is raised to the point for fibers to thermally fuse with each other at the tips of engraved points and against the smooth roll. The heating time is typically in the order of milliseconds. The fabric properties are dependent on process settings such as roll temperatures, web line speeds, and nip pressures, all of which can be determined by the skilled person for the desired level of point bonding. Other types of point bonding known generally as hot calendar bonding may consist of different geometries for the bonds (other than circular shaped), such as oval, lines, circles, etc. In the exemplary embodiment disclosed herein, the point bonding produces a pattern of point bonds being 0.5 mm diameter circles with 10% overall bonding area. Other embodiments comprise bonding shapes where the raised pins have a longest dimension across the bonding surface of a pin of from about 0.1 mm to 2.0 mm and the overall bonding area ranges from 5% to 30%.

As shown in FIG. 11, in an embodiment, heated compaction roll 70 can form a bond pattern, which can be a substantially continuous network bond pattern 80 (e.g., interconnected heart shaped bonds) on first surface 12 of nonwoven fabric 10 (not shown in FIG. 11, as it faces away from the viewer), and engraved calendar roll 73 can form relatively small point bonds 90 on second surface 14 of fabric 10. The point bonds 90 secure loose fibers that would otherwise be prone to fuzzing or pilling during use of the fabric 10. The advantage of the resulting structure of nonwoven fabric 10 is most evident when used as a topsheet in a personal care article such as a diaper or sanitary napkin. In use in a personal care article, the first surface 12 of nonwoven fabric 10 can be relatively flat (relative to second surface 14) and have a relatively large amount of bonding due to the heated compaction roll forming bonds 80 at the areas of the fabric pressed by the raised elements of forming belt 60. This bonding gives the nonwoven fabric 10 structural integrity, but can be relatively stiff or rough to the skin of a user. Therefore, the first surface 12 of the nonwoven fabric 10 can be oriented in a diaper or sanitary napkin to face the interior of the article, i.e., away from the body of the wearer. Likewise, the second surface 14 can be body facing in use, and in contact with the body. The relatively small point bonds 90 are less likely to be perceived visually or tactilely by the user, and the relatively soft three-dimensional features remain visually free of fuzzing and pilling while feeling soft to the body in use. Further bonding can be used instead of, or in addition to, the above mentioned bonding.

Forming belt 60 can be made according to the methods and processes described in U.S. Pat. No. 6,610,173, issued to Lindsay et al. on Aug. 26, 2003, or U.S. Pat. No. 5,514,523 issued to Trokhan et al. on May 7, 1996, or U.S. Pat. No. 6,398,910 issued to Burazin et al. on Jun. 4, 2002, or US Pub. No. 2013/0199741, published in the name of Stage et al. on Aug. 8, 2013, each with the improved features and patterns disclosed herein for making spunbond nonwoven webs. The Lindsay, Trokhan, Burazin and Stage disclosures describe belts that are representative of papermaking belts made with cured resin on a woven reinforcing member, which belts, with improvements, can be utilized in the present disclosure as described herein.

Figure 12:
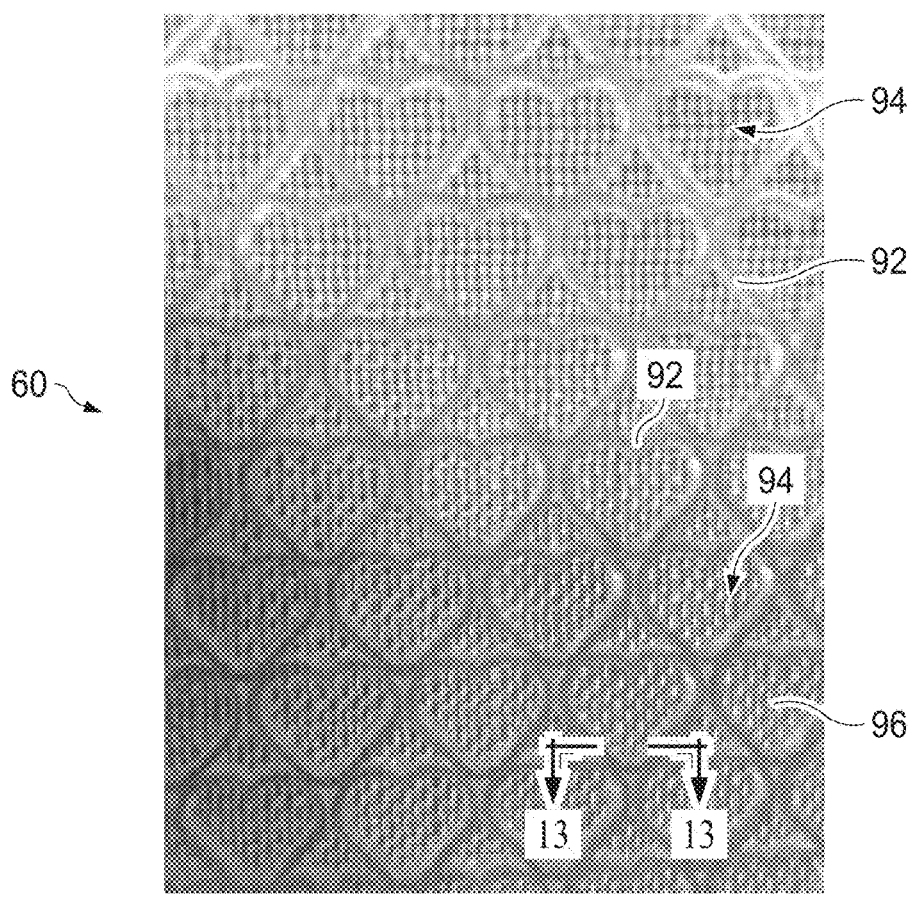
FIG. 12 is a photograph of a portion of a forming belt useful for the present disclosure.

An example of a forming belt 60 of the type useful in the present disclosure and which can be made according to the disclosure of U.S. Pat. No. 5,514,523, is shown in FIG. 12. As taught therein, a reinforcing member 94 (such as a woven belt of filaments 96) is thoroughly coated with a liquid photosensitive polymeric resin to a preselected thickness. A film or negative mask incorporating the desired raised element pattern repeating elements (e.g., FIG. 14) is juxtaposed on the liquid photosensitive resin. The resin is then exposed to light of an appropriate wavelength through the film, such as UV light for a UV-curable resin. This exposure to light causes curing of the resin in the exposed areas (i.e., white portions or non-printed portions in the mask). Uncured resin (resin under the opaque portions in the mask) is removed from the system leaving behind the cured resin forming the pattern illustrated, for example, the cured resin elements 92 shown in FIG. 12. Other patterns can also be formed, as discussed herein.

Figure 13:
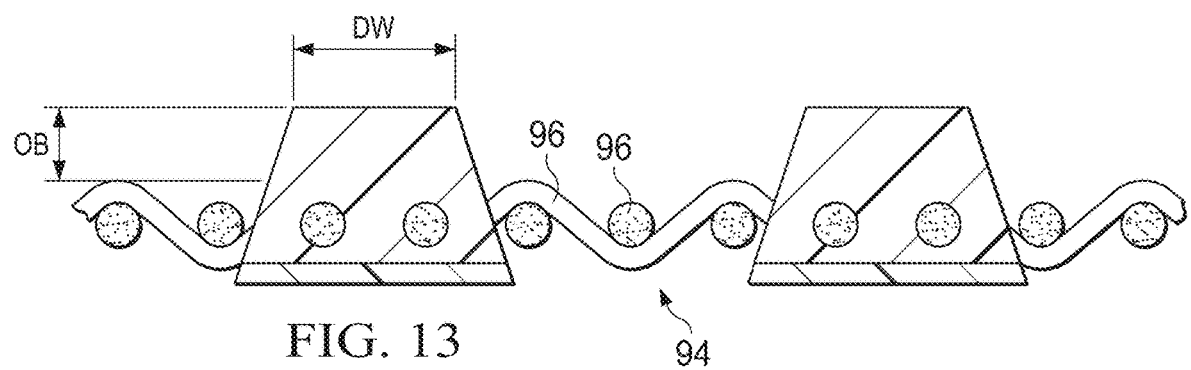
FIG. 13 is a cross-sectional depiction of a portion of the forming belt shown in FIG. 12.
Figure 14:
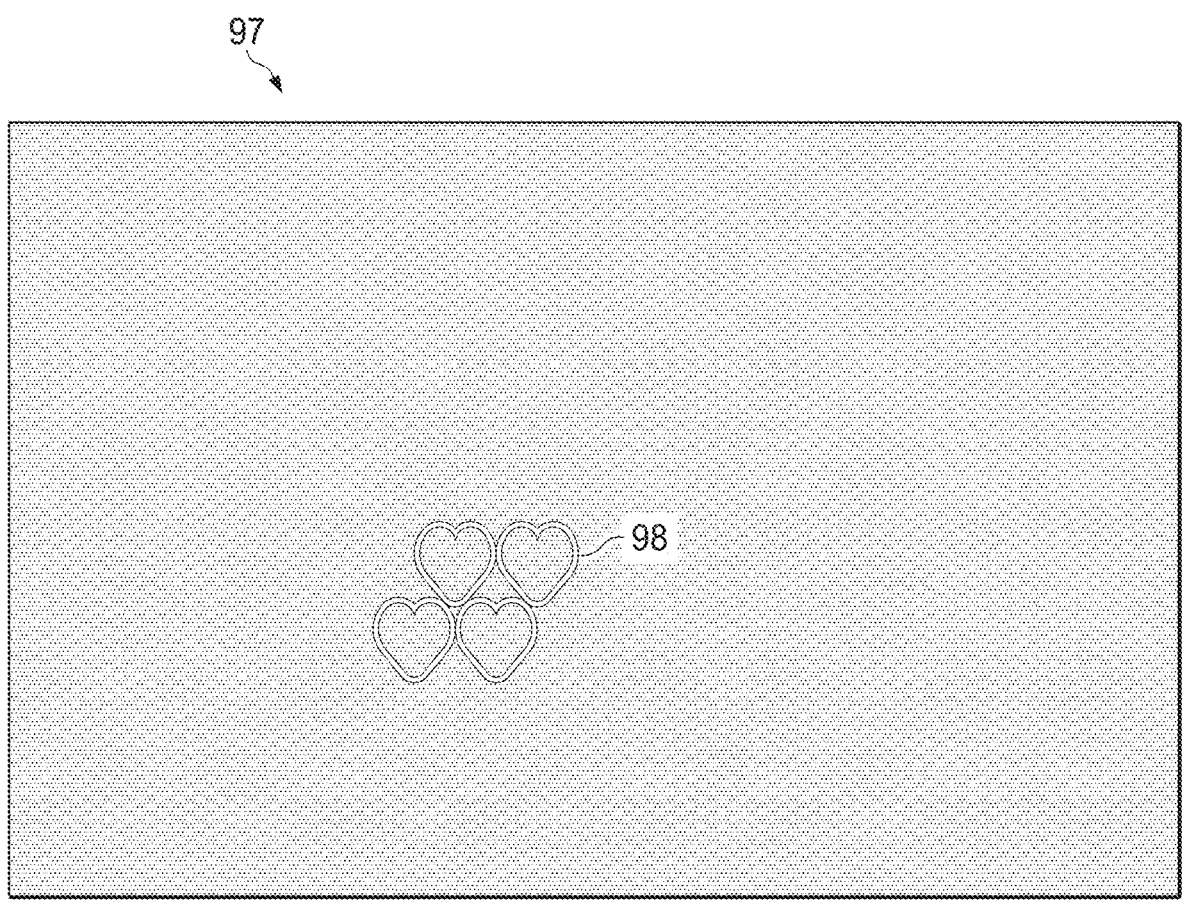
FIG. 14 is an image of a portion of a mask utilized to make the forming belt shown in FIG. 12.

FIG. 12 shows a portion of a forming belt 60 useful for making the nonwoven fabric 10 shown in FIG. 1. As shown, the forming belt 60 can include cured resin elements 92 on a woven reinforcing member 94. The reinforcing member 94 can be made of woven filaments 96 as is known in the art of papermaking belts, including resin coated papermaking belts. The cured resin elements can have the general structure depicted in FIG. 12, and are made by the use of a mask 97 having the dimensions indicated in FIG. 14. As shown in schematic cross-section in FIG. 13, cured resin elements 92 flow around and are cured to "lock on" to reinforcing member 94 and can have a width at a distal end DW of about 0.020 inch to about 0.060 inch, or from about 0.025 inch to about 0.030 inch, and can have a total height above the reinforcing member 94, referred to as overburden, OB, of between about 0.015 inch and about 0.060 inch, or between about 0.020 and about 0.050 inch, or between about 0.025 inch and about 0.045 inch, or between about 0.030 inch and about 0.040 inch, or between about 0.030 inch and about 0.035 inch. FIG. 14 represents a portion of a mask 97 showing the design and representative dimensions for one repeat unit of the repeating hearts design in the nonwoven fabric 10 shown in FIG. 1. The white portion 98 is transparent to UV light, and in the process of making the belt, as described in U.S. Pat. No. 5,514,523, permits UV light to cure an underlying layer of resin which is cured to form the raised elements 92 on the reinforcing member 94. After the uncured resin is washed away, the forming belt 60 having a cured resin design as shown in FIG. 12 is produced by seaming the ends of a length of the belt, the length of which can be determined by the design of the apparatus, as depicted in FIG. 7.

Figure 15:
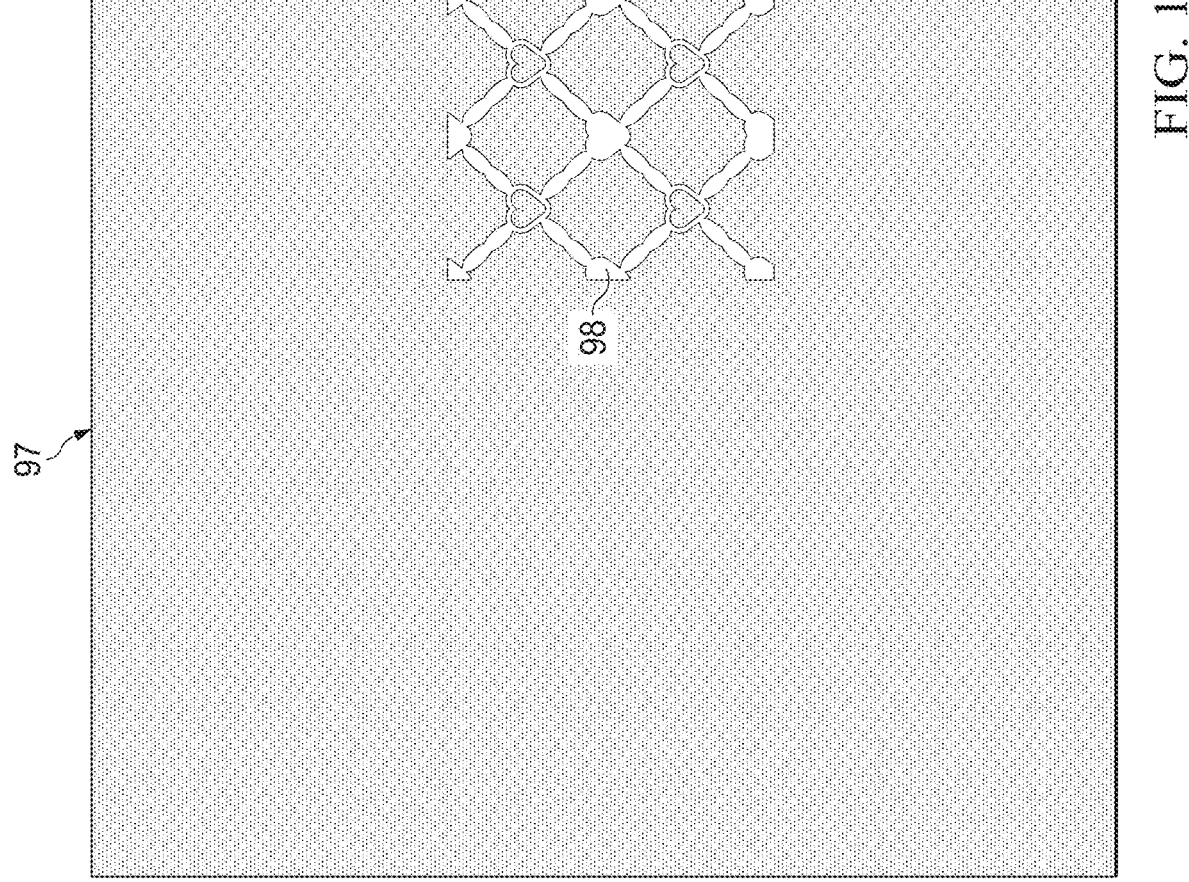
FIG. 15 is an image of a portion of a mask utilized to make the forming belt shown in FIG. 16.
Figure 16:
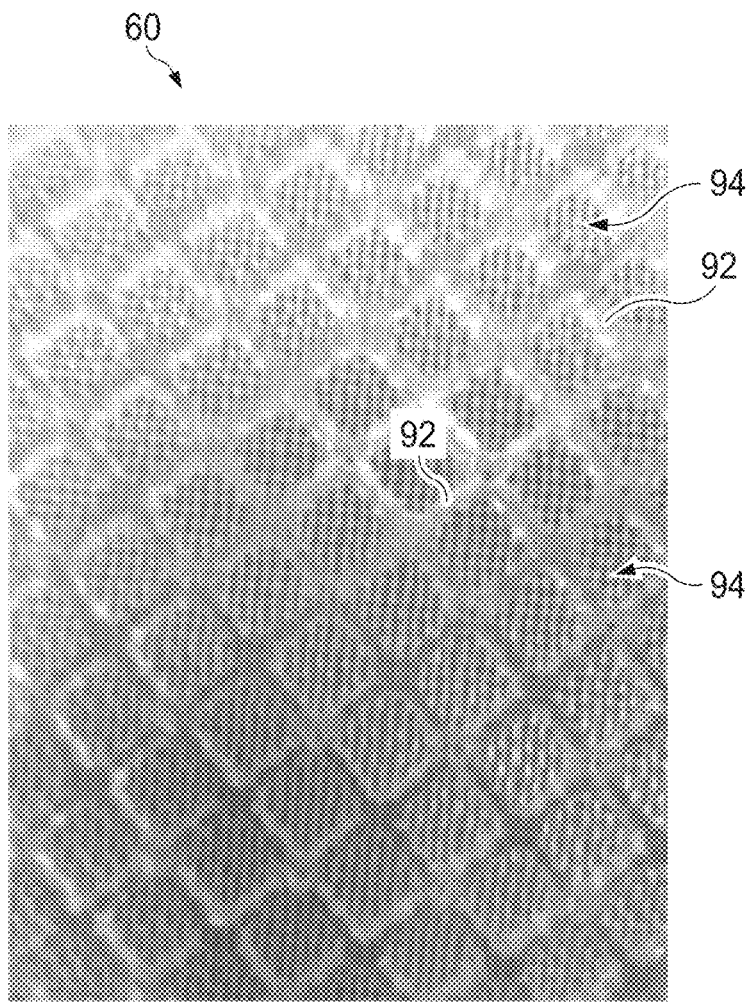
FIG. 16 is a photograph of a portion of a forming belt useful for the present disclosure.

In like manner. FIG. 15 represents a portion of a mask 97 showing the design for one repeat unit of the repeating design in the nonwoven fabric 10 shown in FIG. 2. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 16 is produced by seaming the ends of a length of the belt, the length of which can be determined by the design of the apparatus, as depicted in FIG. 7.

Figure 17:
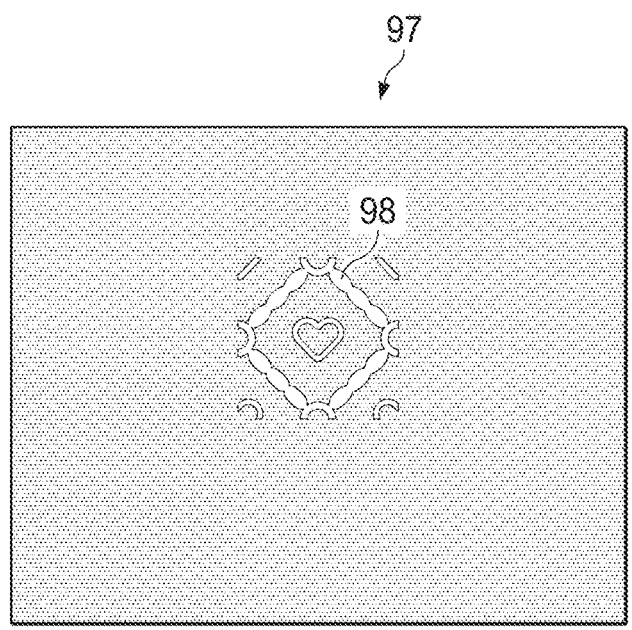
FIG. 17 is an image of a portion of a mask utilized to make the forming belt shown in FIG. 18.
Figure 18:
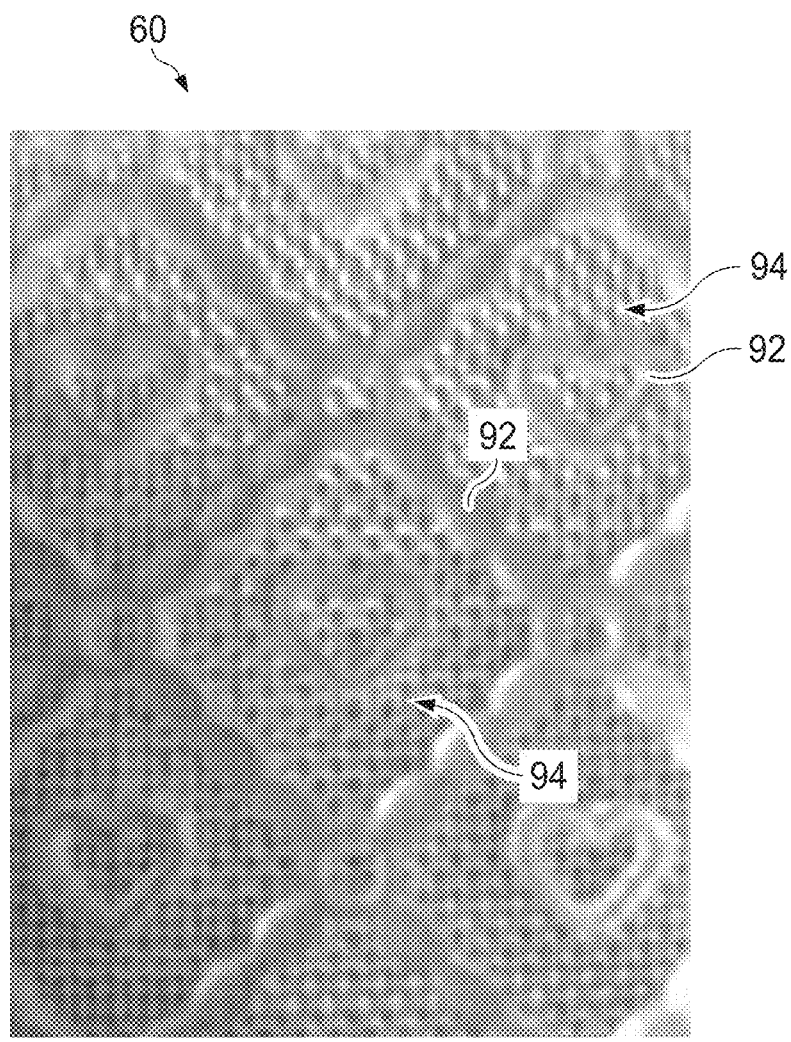
FIG. 18 is a photograph of a portion of a forming belt useful for the present disclosure.

Further, in another non-limiting example, FIG. 17 represents a portion of a mask showing the design for one repeat unit of the repeating design in the nonwoven fabric 10 shown in FIG. 18. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 18 is produced by seaming the ends of a length of fabric 10.

Figure 19:
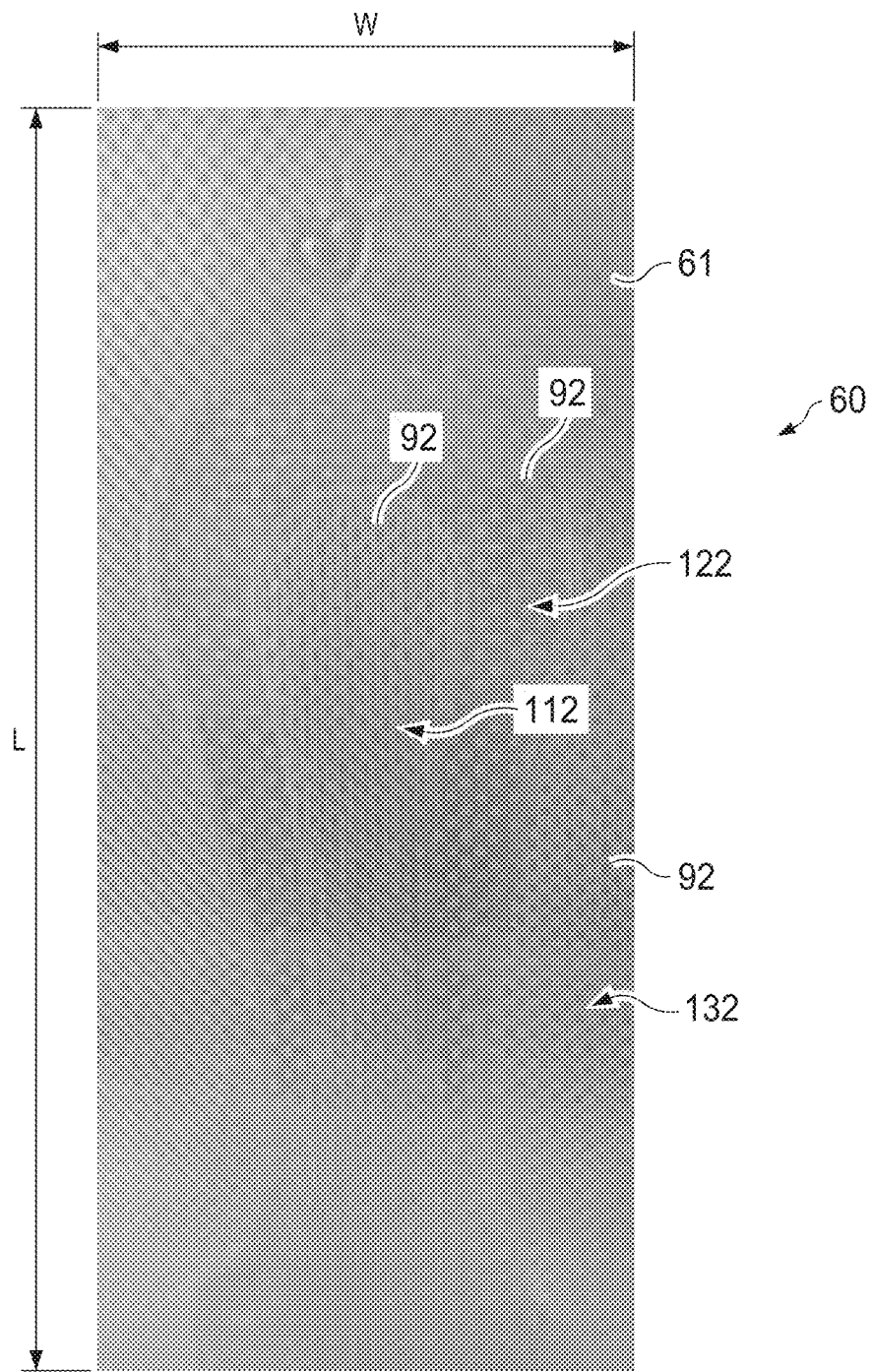
FIG. 19 is a photograph of a portion of a forming belt useful for the present disclosure.
Figure 20:
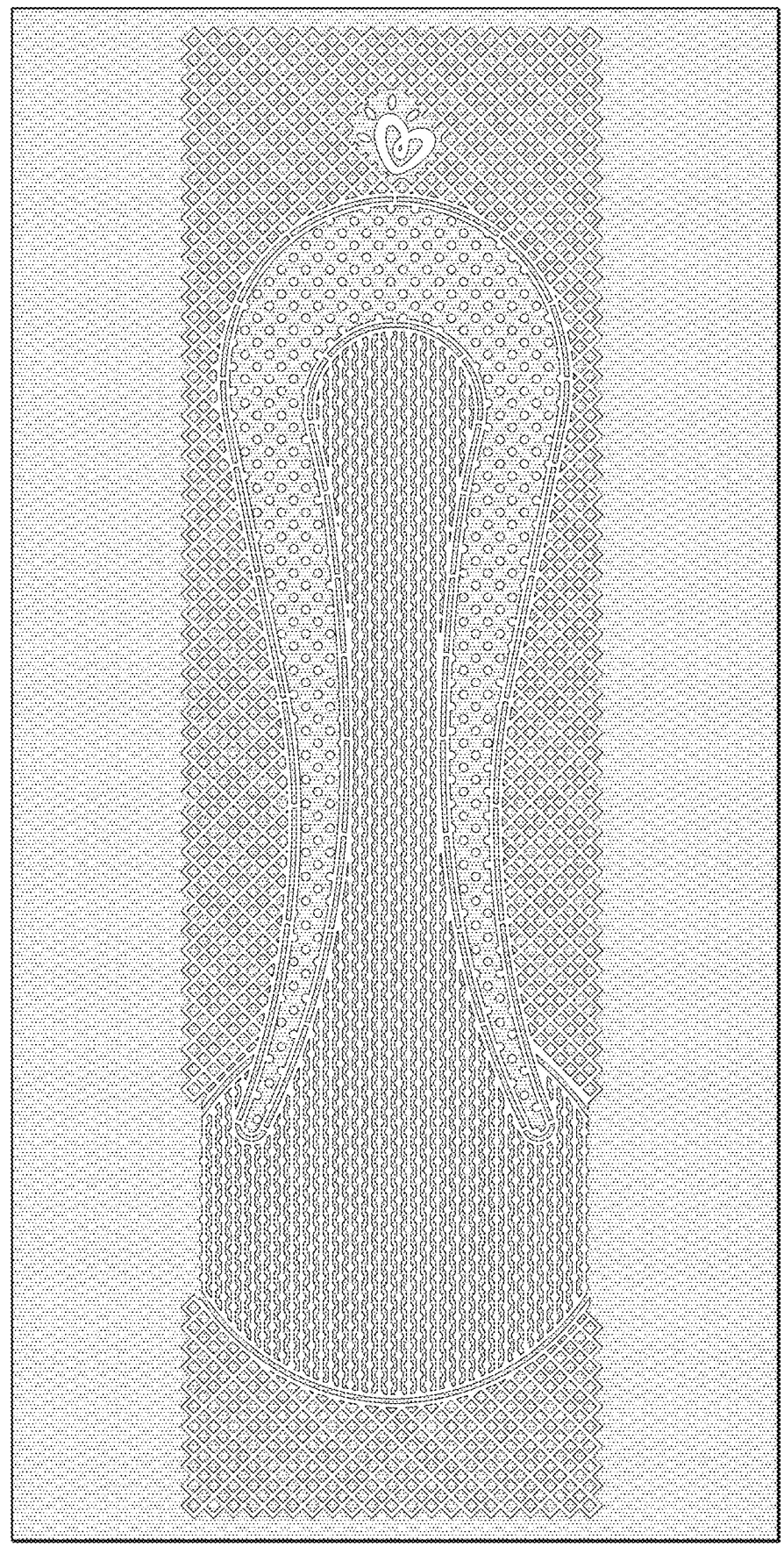
FIG. 20 an image of a mask utilized to make the forming belt shown in FIG. 19.

Another example of a portion of a forming belt 60 of the type useful in the present disclosure is shown in FIG. 19. The portion of the forming belt 60 shown in FIG. 19 is a discrete belt pattern 61 that can have a length L and width W corresponding to the length L and width W of the overall area OA of a nonwoven fabric 10. That is, the forming belt 60 can have discrete belt patterns 61 (as discussed more fully with reference to FIG. 22 below), each having a discrete belt pattern overall area DPOA that corresponds to the overall area OA of the nonwoven fabric 10. FIG. 20 represents a portion of a mask showing the design for one repeat unit of the repeating design in the nonwoven fabric 10 shown in FIG. 21. The white portion 98 is transparent to UV light, and in the process of making the belt permits UV light to cure an underlying layer of resin which is cured to the reinforcing member 94. After the uncured resin is washed away, the forming belt 60 having a cured resin design as shown in FIG. 19 is produced by seaming the ends of a length of the belt.

The portion of the forming belt shown in FIG. 19 illustrates another benefit of the present disclosure. The portion of a forming belt 60 shown in FIG. 19 can make a fabric 10 shown in FIG. 21. The nonwoven fabric 10 shown in FIG. 21 can have width W and length L dimensions and an overall area OA making it suitable for use as a topsheet in a disposable diaper, for example. The nonwoven fabric 10 made on a forming belt 60 as exemplified in FIG. 19 differs from that shown in FIGS. 1-3 in that the pattern of three-dimensional features formed by the discrete resin elements 92 on forming belt 60 are not in a regular, repeating pattern across the entire overall area. Rather, the pattern of three-dimensional raised elements in the discrete belt pattern overall area DPOA can be described as an irregular pattern encompassing distinct portions referred to as zones. The distinction between zones can be visual, i.e., a visually discernible difference, or in the nonwoven fabric 10 the distinction can produce a difference in average intensive properties such as basis weight or density, or combinations of visual and intensive properties. A visually discernible difference exists if an observer in ordinary indoor lighting conditions (20/20 vision, lighting sufficient to read by, for example) can visually discern a pattern difference between the zones, such as the first zone 112 and the second zone 122.

Figure 21:
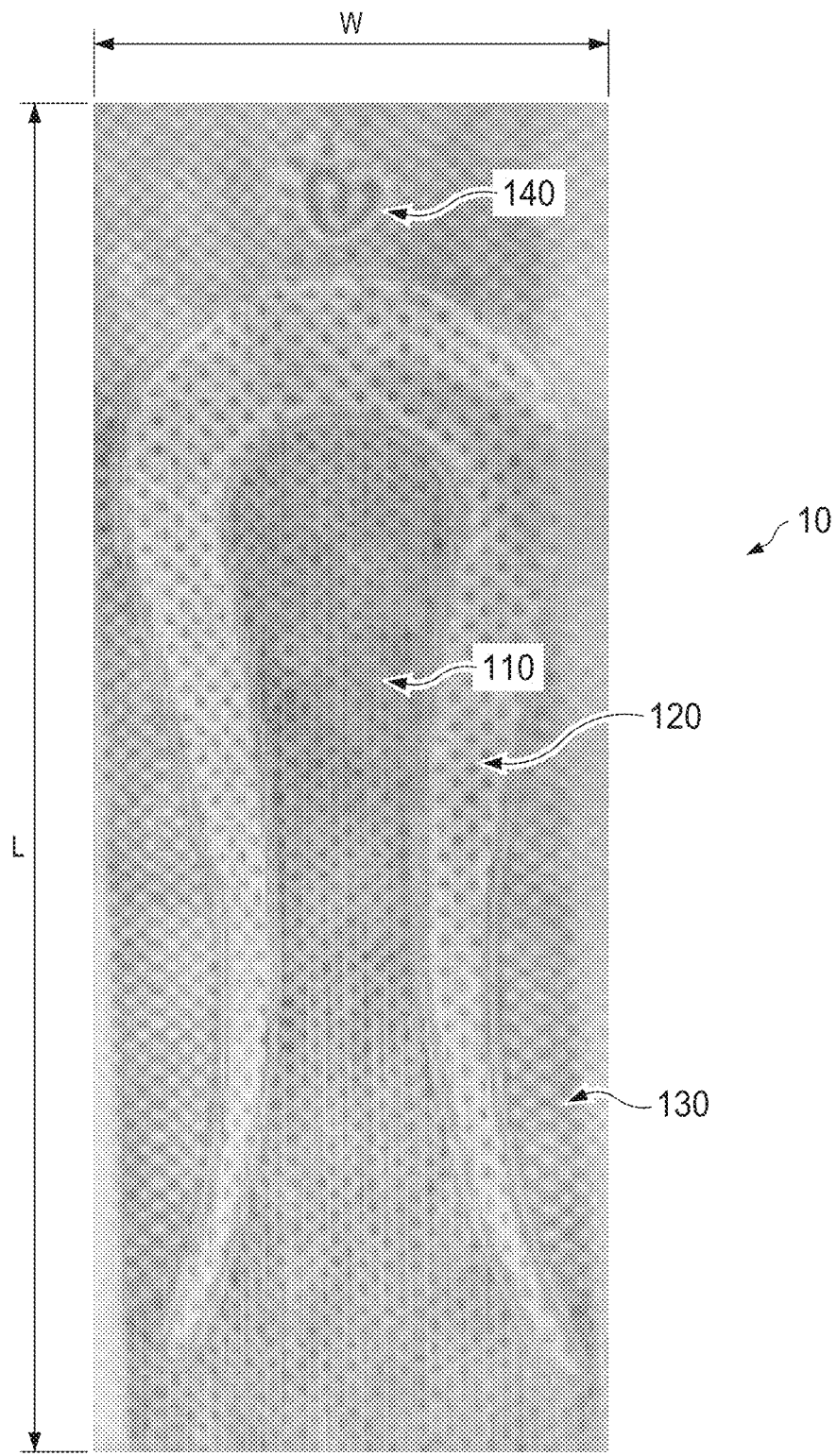
FIG. 21 is a photograph of a fabric of the present disclosure made on the forming belt shown in FIG. 19.

The nonwoven fabric 10 can also have visually discernible zones corresponding to the zones of the forming belt. As shown in FIG. 21, for example, fabric 10 can have at least two, three, or four visually discernible zones. A first zone 110, having first pattern of three-dimensional features and first average intensive properties, can have a first area generally centrally located within the overall area OA. A second zone 120, having second pattern of three-dimensional features and second average intensive properties, can have a second area distributed generally about, and in an embodiment, completely surrounding, the first zone 110 within the overall area OA. A third zone 130, having third pattern of three-dimensional features and third average intensive properties, can have a third area distributed generally about, and in an embodiment, completely surrounding, the second zone 120 within the overall area OA. A fourth zone 140, having fourth three-dimensional features and fourth average intensive properties, can have a fourth area positioned within the overall area OA in any location, such as at a front area of a topsheet, such as the heart design shown in FIG. 21. In general, there can be n zones, with n being a positive integer. Each of the n zones can have an nth pattern of three-dimensional features and an nth area and nth average intensive properties.

The visually discernible zones as shown in FIG. 21 may comprise visually discernible three-dimensional features. These distinct three-dimensional features may be bounded by relatively higher density (with respect to the interior of a three-dimensional feature) regions that may be in the form of a closed figure, such as the heart shape in FIGS. 1 and 3, and the diamond shape of FIGS. 2 and 3. In general, as discussed more fully below, including in the context of micro zones, the three-dimensional features can be defined by a first region and a second region, wherein the first region and second region are visually distinct and there is a common intensive property associated with each of the first and second regions and there is a difference in the first region's and second region's common intensive property value. In an embodiment, the three-dimensional features can be defined by a first region and a second region, with the first region being at a higher elevation (dimension measured in the Z-direction) than the second region with respect to the plane of the first surface. In another embodiment, the three-dimensional features can be defined by a first region and a second region, with the first region being at a higher basis than the second region.

As can be understood, rather than having a constant repeating pattern that is uniform across the entire forming belt, the forming belt 60 of the present disclosure allows the production of a nonwoven material that can have repeats of irregular discrete belt patterns 61, each discrete belt pattern 61 being like the discrete belt pattern shown in FIG. 19. The discrete belt patterns 61 each can be used to form one nonwoven fabric 10 having an overall area OA suitable for use in a disposable absorbent article, such as diaper or sanitary napkin, for example. The nonwoven fabrics 10 can be produced sequentially, i.e., in line, and, optionally sequentially in parallel lanes, each lane being a sequential line of nonwoven fabrics 10. The sequential line of nonwoven fabrics 10 can be produced in a machine direction along an axis parallel to the machine direction. The nonwoven material can then be slit or otherwise cut to size to produce nonwoven fabrics 10 utilized as a topsheets in disposable absorbent articles, such as diapers or sanitary napkins.

In an embodiment, the pattern within each discrete belt pattern overall area DPOA can be the same or different. That is, the sequentially spaced discrete belt patterns can be substantially identical, or they can differ in visual appearance and/or in the intensive properties produced in nonwoven substrates produced thereon. For example, as shown schematically in FIG. 22, the pattern of three-dimensional raised elements in first forming zone 112 of discrete belt pattern 61A can be different from the pattern of three-dimensional raised elements in first forming zone 112 of discrete belt pattern 61B. The forming belt 60 thus offers flexibility in producing nonwoven webs 10 suitable for use in consumer goods, including disposable absorbent articles. For example, in one package of diapers, the topsheets of at least two diapers can be different because they were produced sequentially in a spunbond process as described herein, with sequential discrete belt patterns having different patterns of zones. In an embodiment, the topsheet or backsheet nonwoven pattern for one size of diaper can be different from the topsheet or backsheet nonwoven of another size of diaper, thereby giving a caretaker a visual clue as to the size of a diaper. Likewise, sanitary napkins can utilize a fabric 10 for a topsheet, with the visual pattern of three-dimensional features denoting the absorbency of the sanitary napkin. In any event, the various patterns of fabrics 10 can be produced on a single belt by making the discrete belt patterns different as desired.

Figure 22:
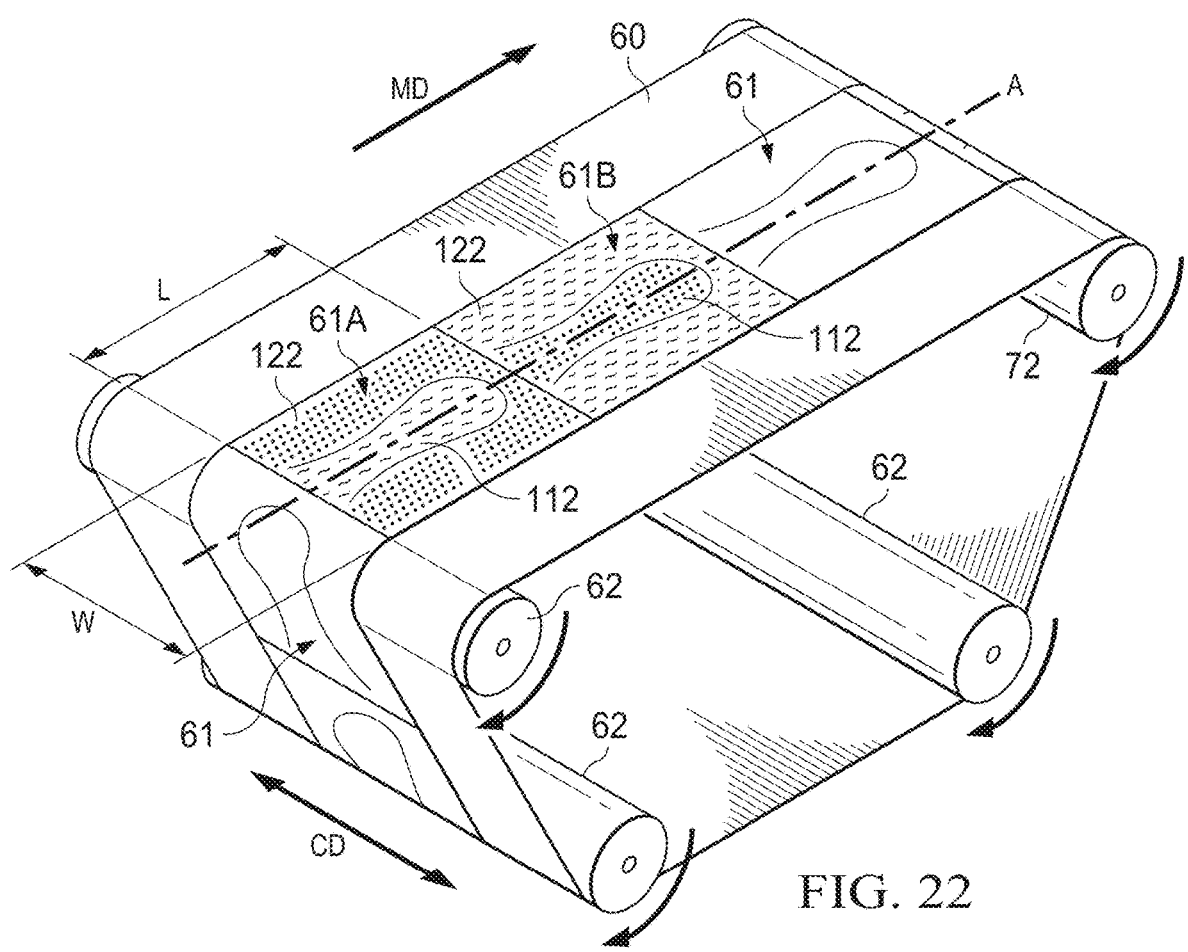
FIG. 22 is a perspective schematic view of a forming belt of the present disclosure.

With reference to FIG. 22, a forming belt has an axis A parallel to a longitudinal direction which is a machine direction. The forming belt 60 can have a plurality of discrete belt patterns 61 ordered in at least one sequential relationship with respect to the longitudinal direction. Each discrete belt pattern 61 can have a discrete belt pattern overall area DPOA defined, in a rectangular-shaped pattern, by a length L and width W, as indicated with respect to discrete belt pattern 61A. Each discrete belt pattern within its overall area DPOA can have a first forming zone 112 having a first pattern of three-dimensional raised elements extending outwardly from the plane of the of the first surface and a second forming zone 122 having second three-dimensional raised elements extending outwardly from the plane of the of the first surface. The first forming zone can have a first air permeability value and the second forming zone can have a second air permeability value, and the first air permeability value can be different from the second air permeability value. The pattern within each sequentially ordered discrete belt pattern overall area DPOA can be the same or different.

By way of example, and referring to the discrete belt pattern 61 of forming belt 60 shown in FIG. 19, and the nonwoven fabric 10 shown in FIG. 21, the following properties were determined. First zone 110 of nonwoven fabric 10 can have an average basis weight of about 5 gsm to about 30 gsm; the second zone 120 can have an average basis weight of about 50 gsm to about 70 gsm; and the third zone 130 can have an average basis weight of about 25 gsm to about 60 gsm. The difference in basis weight from one zone to another can be attributed to a difference in air permeability of the forming belt 60. In the embodiment used to make the nonwoven fabric 10 shown in FIG. 20, in which the basis weights for zones 110, 120, and 130, are 15 gsm, 53 gsm and 25 gsm, respectively, the air permeability of the respective zones 112, 122, and 132 of the forming belt 60 are 379 cfm, 805 cfm, and 625 cfm, respectively. Thus, by varying air permeability in zones in forming belt 10, the intensive properties of average basis weight and average density in zones can be facilitated across the overall area of fabric 10.

Figure 23:
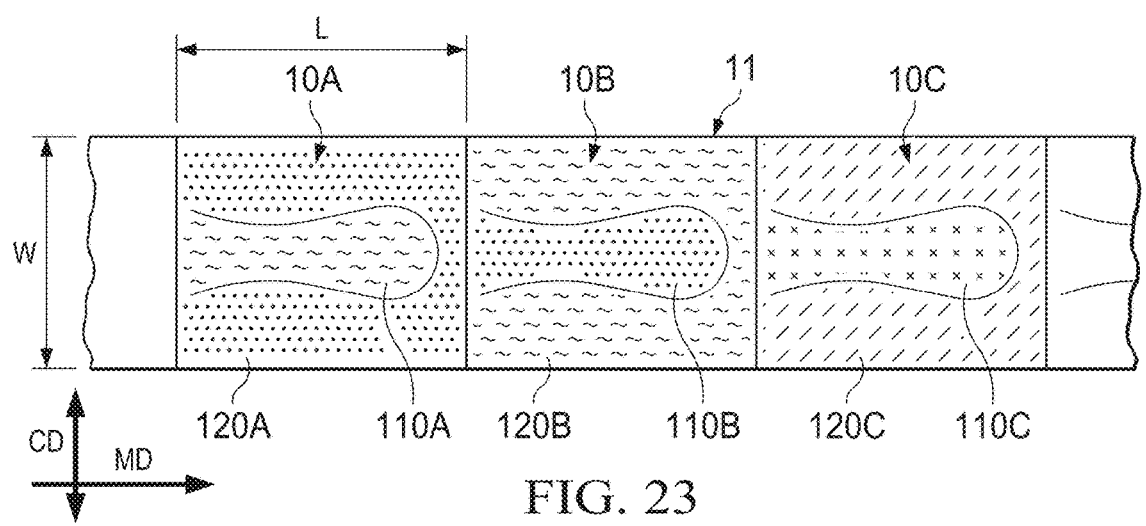
FIG. 23 is a plan view of a nonwoven substrate including nonwoven fabrics of the present disclosure.

As can be understood from the description of the forming belt 60 described in FIG. 22, and with reference to FIG. 23, in an embodiment the nonwoven substrate 11 made on belt 60 can be described as a nonwoven substrate 11 having a plurality of portions described herein as fabrics 10 ordered in at least one sequential relationship with respect to the longitudinal direction, i.e., the machine direction when made on forming belt 60. FIG. 23 is a schematic representation of a spunbond nonwoven substrate 11 showing the sequentially ordered fabrics 10, each fabric 10 having a different pattern within the various zones. Each fabric 10 can have an overall area OA defined, in a rectangular-shaped pattern, by a length L and width W. Each sequentially disposed fabric 10 can have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA can be present. As shown in the exemplary schematic representation of FIG. 23, the first pattern 110A of fabric 10A can be different from the first pattern 1101B of fabric 10B, and can be different from first pattern 110C of fabric 10C. The same can be true for second zones 120A, 120B, and 120C.

In general, the sequentially ordered nonwoven fabrics 10 of the nonwoven material 11 made on forming belt 60 can vary in their respective overall areas, intensive properties, and visual appearances. A common intensive property is an intensive property possessed by more than one zone (with respect to zonal patterns, such as that shown in FIG. 21) or region (for three-dimensional features such as the regular repeating patterns, such as that shown in FIG. 1). Such intensive properties of the nonwoven fabrics 10 can be average values, and can include, without limitation, density, volumetric density, basis weight, thickness, and opacity. For example, if a density is a common intensive property of two differential zones or regions, a value of the density in one zone or region can differ from a value of the density in the other zone or region. Zones (such as, for example, a rust zone and a second zone) can be identifiable areas distinguishable from one another visually and by distinct intensive properties averaged within the zone.

Figure 24:
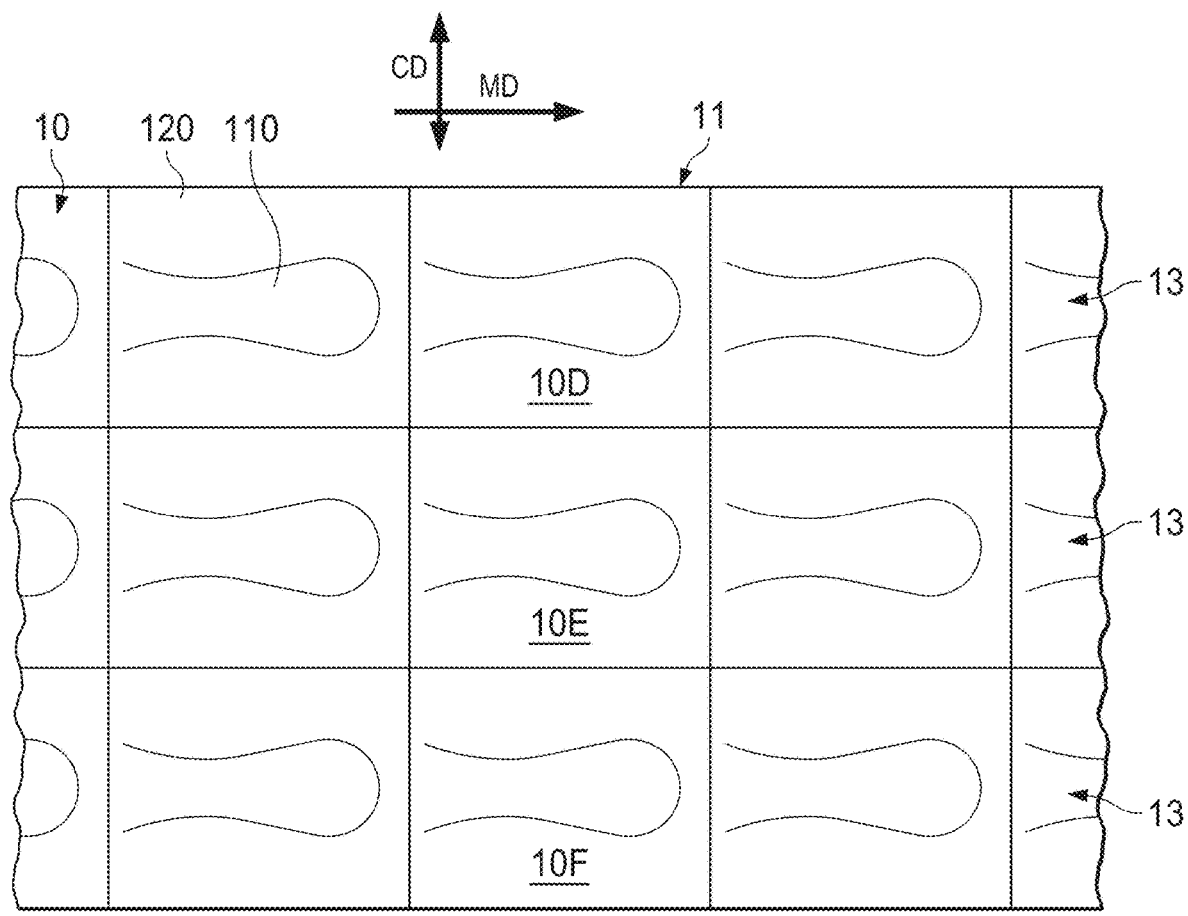
FIG. 24 is a plan view of a nonwoven substrate including nonwoven fabrics of the present disclosure.

Once produced, the individual nonwoven fabrics 10 can be cut to size and utilized for their intended purposes, such as for topsheets in disposable absorbent articles. For example, a disposable diaper 1006 in a flattened orientation is shown in FIG. 24. One fabric 10 is cut to the appropriate overall area and adhered into the diaper 1006 by means known in the art. Fabrics 10 can be cut prior to being assembled into a diaper 1006, or during the diaper making process the nonwoven substrate 11 can be brought together with other diaper components in web form, and cut to size after assembly.

As can be understood with reference to FIG. 24, in an embodiment the nonwoven substrate 11 made on belt 60 can be described as a nonwoven fabric 11 having a plurality of portions described herein as fabrics 10 ordered in at least one sequential relationship with respect to the longitudinal direction, i.e., the machine direction when made on forming belt 60, in at least one side-by-side relationship, i.e., in the cross machine direction when made on forming belt 60. FIG. 24 is a schematic representation of a spunbond nonwoven substrate 11 showing the sequentially ordered fabrics 10 in adjacent machine direction lanes 13, adjacent lanes having the side-by each fabrics 10, called out in FIG. 24 as 10D, 10E, and 10F. Each fabric 10 can have an overall area OA defined, in a rectangular-shaped pattern, by a length L and width W. Each sequentially disposed fabric 10 can have within its overall area OA at least a first zone 110, having a first pattern of three-dimensional features and first average intensive properties, and a first area located within the overall area OA; a second zone 120, having a second pattern of three-dimensional features and second average intensive properties, having a second area located within the overall area OA. Optionally, more zones, e.g., a third zone 130, having third pattern of three-dimensional features and third average intensive property and having a third area within the overall area OA can be present. Each fabric 10 in side-by-side lanes can be substantially identical, or they can be different with respect to size, visual appearance, and/or intensive properties. Once produced, the nonwoven substrate 11 can be reeled for slitting into lanes for processing into consumer products, or slit and then reeled.

By way of representative sample to compare basis weight differentials in a fabric 10 made with a regular, repeating, uniform pattern and a fabric 10 made with a non-uniform, zonal pattern, the nonwoven fabric 10 of Example 1 was compared with a fabric having a pattern similar to that shown in FIG. 21, and referred to as Example 3. Example 3 is a bicomponent spunbond nonwoven web produced on the apparatus disclosed herein by spinning 50:50 ratio of polyethylene sheath (Aspun-6850-A obtained from Dow chemical company) and polypropylene core (PH-835 obtained from LyondellBasell) in a trilobal fiber configuration. The spunbond, bicomponent, trilobal fibers were laid down on a forming belt 60 moving at a linear speed of about 25 meters per minute to an average basis weight of 30 grams per square meter on a forming belt with a zonal pattern as shown in FIG. 19. The second substrate was formed under identical conditions, but had at least one section having a regular, repeating, uniform pattern on a forming belt as shown in FIG. 16, from which basis weight was determined. Fiber spinning conditions, through-put, forming belt line speed and compaction roll bonding temperature were identical for both substrates.

Example 3

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of 30 grams per square meter. A nonwoven fabric was produced as described with respect to FIGS. 7 and 8 moving at a forming belt linear speed of about 25 meters per minute to form a fabric having zonal pattern as shown in FIG. 20. Fibers of the fabric were further bonded on first surface 12 by heated compaction rolls 70, 72 at 130° C., and the fabric was wound on to a reel at winder 75.

Example 4

A bicomponent spunbond nonwoven fabric that was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of 30 grams per square meter. A nonwoven fabric was produced as described with respect to FIGS. 7 and 8 moving at a forming belt linear speed of about 25 meters per minute to form a fabric having repeating (non-zonal) pattern as shown in FIG. 2. Fibers of the fabric were further bonded on first surface 12 by heated compaction rolls 70, 72 at 130° C., and being wound on to a reel at winder 75.

Figure 25A:
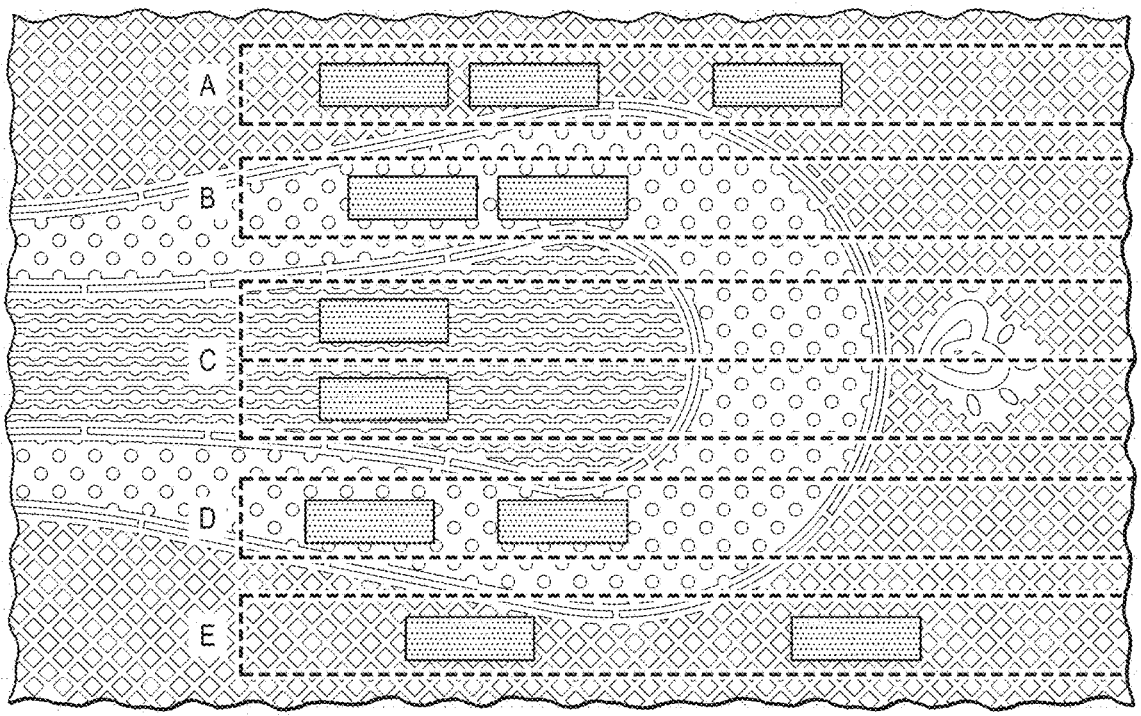
FIG. 25A is a plan view of a fabric of the present disclosure with portions removed for measurement of local basis weight.
Figure 25B:
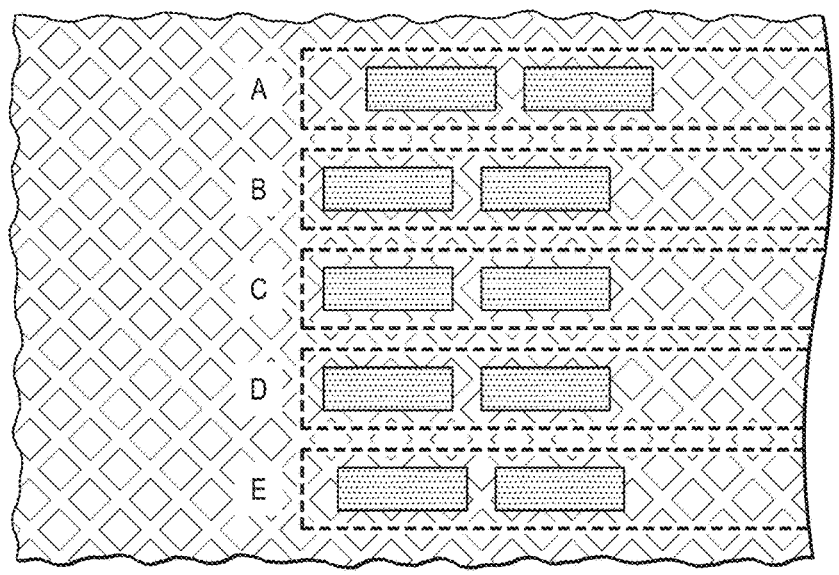
FIG. 25B is a plan view of a fabric of the present disclosure with portions removed for measurement of local basis weight.
Figure 26:
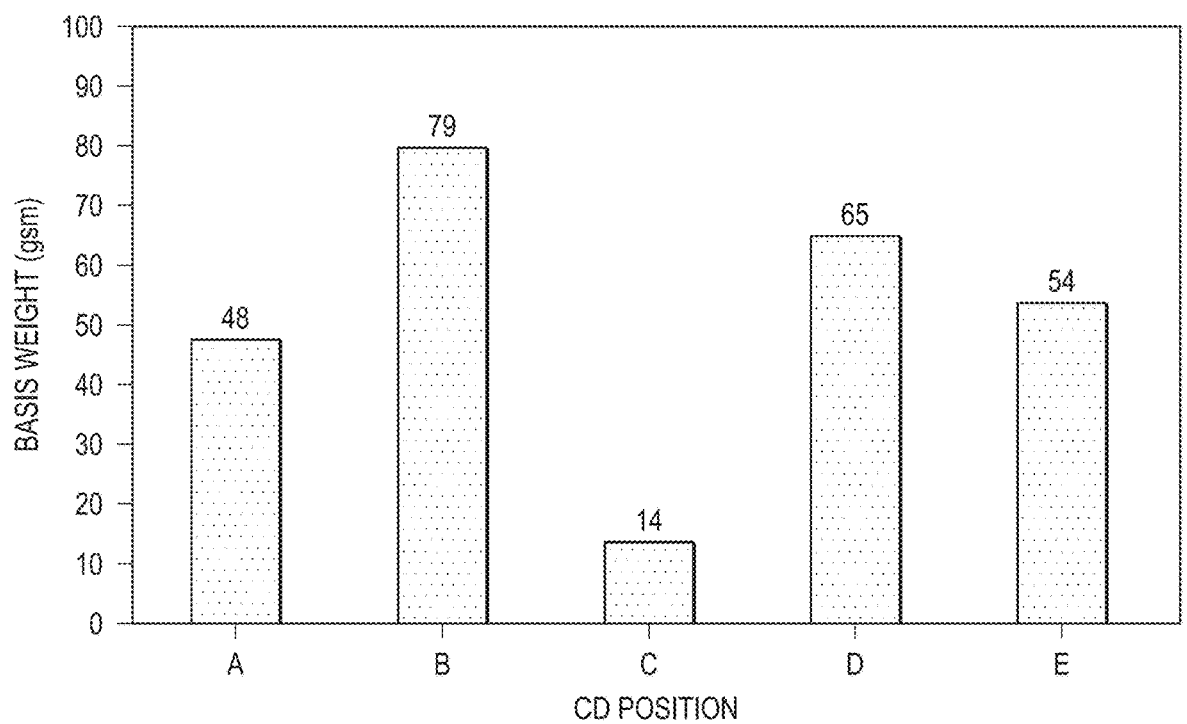
FIG. 26 is a graphical representation of cross-directional variation in basis weight in a fabric of the present disclosure.

Table 2 below shows average local basis weight, measured according to the Localized Basis Weight test method herein, and averaged over 10 samples. The samples for measurement were taken from the fabrics as shown in FIGS. 25A and 25B, in which the dark rectangles are where a 3 cm$^2$ sample was removed for measurement. As can be seen, the fabrics are labeled across the cross-direction (CD) as A-E. The measurements shown not only a significant difference in basis weight between zones of the zonal fabric, but a CD distribution which is depicted graphically in FIG. 26.

TABLE 2

Measured Average Basis Weight distribution in nonwoven fabric 10 in grams per square meter (gsm)

| Region as Depicted in FIG. 25 | Example 3: Zonal Fabric Basis Weights | Example 4: Non-zonal Fabric Basis weights |
| --- | --- | --- |
| A | 48 gsm | 43 gsm |
| B | 79 gsm | 37 gsm |
| C | 14 gsm | 32 gsm |
| D | 65 gsm | 36 gsm |
| E | 54 gsm | 36 gsm |

As can be seen in Table 2, fabrics 10 made on forming belts 60 having zones of differing air permeability demonstrate substantial variation in fiber laydown and thus basis weights within the CD of nonwoven fabric 10 suggesting the ability for fibers to travel with air into high permeability zones. The non-zonal, regular repeating pattern fabric 10 exhibits approximately the same basis weights within the CD of fabric.

In addition to differences in air permeability of the various zones of the forming belt 60, the structure of forming belt 60 can affect other intensive properties of zones in the fabric 10, such as average caliper, average softness, average compression resistance, and fluid absorption properties.

Another aspect of this invention relates to spunbond commercial lines where multiple beams are utilized for improved laydown opacity and uniformity of the fabric. In some cases, there the apparatus can include triple spunbond beams (known in the art as "SSS") and may be combined with meltblown (M), for example, in an apparatus known as an "SSMMS" spunbond line.

By calendaring the nonwoven fabric 10 to have point bonds 90, fuzzing can be reduced. Fuzzing refers to the tendency of fibers to become loose and removed from the fabric 10. Loosening and removal can be because of frictional engagement with manufacturing equipment during production of disposable absorbent articles, or another surface, such as the skin of a person interacting with the fabric 10. In some uses, such as for topsheets in disposable absorbent articles, fuzzing is a negative consumer phenomena. But bonding fibers in place can also be a consumer negative as it can produce roughness on the surface of an otherwise soft nonwoven substrate. We have found expectedly the nonwoven fabrics substrates and nonwoven fabrics of the present disclosure can endure an increase in bonding (and a consequent decrease in fuzzing) with minimal loss in softness. Bonding can be accomplished by relatively closely spaced point bonds 90, with the spacing being determined by the desired level of fuzzing reduction. Bonding can also be achieved by known methods for chemically or thermally bonding nonwoven fibers, such as thermal bonding, ultrasonic bonding, pressure bonding, latex adhesive bonding, and combinations of such methods. Fuzz reduction by bonding is illustrated with respect to Examples 5 and 6 below.

Example 5

Figure 36:
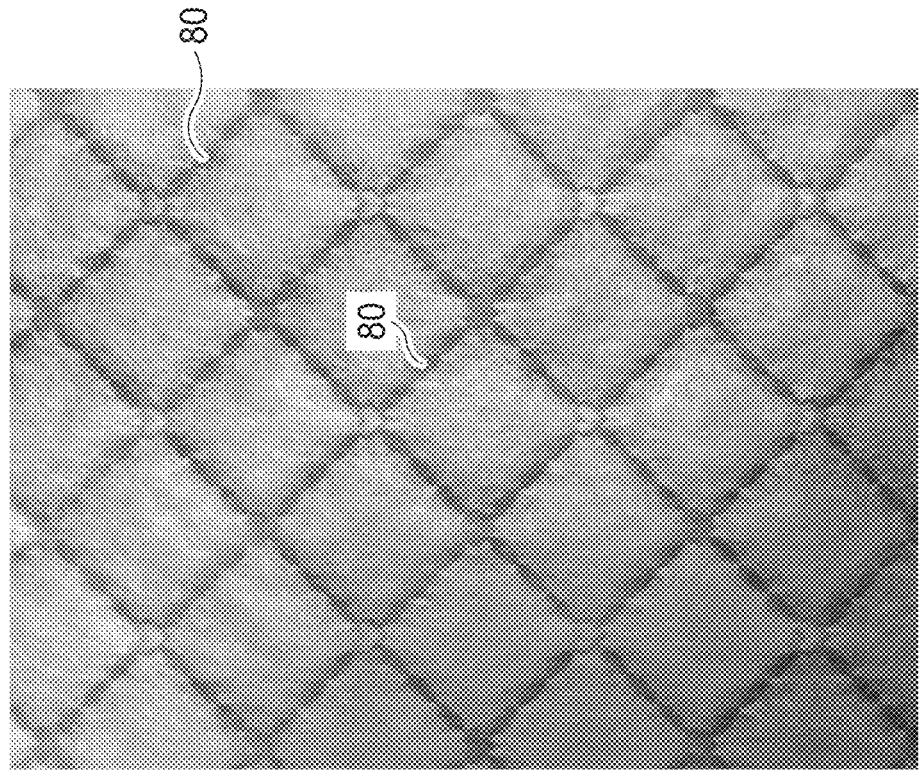
FIG. 36 is a photograph of an example of a shaped nonwoven of the present disclosure.

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of about 30 grams per square meter on a forming belt as described with respect to FIGS. 7 and 8 moving at a linear speed of about 25 meters per minute to form a fabric having the repeating pattern as shown in FIG. 36 Fibers of the fabric were further bonded on first surface 12 by compaction rolls 70, 72 with compaction roll 70 heated to 130° C. to form substantially continuous bonds 80.

Example 6

Figure 37:
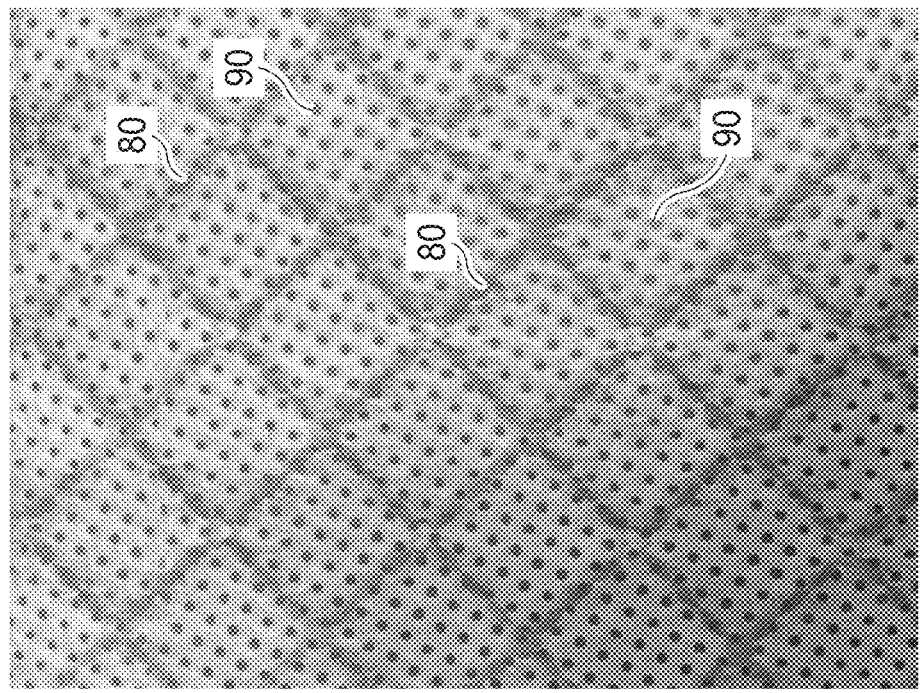
FIG. 37 is a photograph of an example of a shaped nonwoven of the present disclosure.

A bicomponent spunbond nonwoven fabric was produced by spinning a 50:50 ratio of polyethylene sheath (Aspun-6850-A obtained from Dow chemical company) and polypropylene core (PH-835 obtained from LyondellBasell) in a trilobal fiber configuration to an average basis weight of about 30 grams per square meter on a forming belt as described with respect to FIGS. 7 and 8 moving at a linear speed of about 25 meters per minute to form a fabric having the repeating pattern described with respect FIG. 37 Fibers of the fabric were further bonded on first surface 12 by compaction rolls 70, 72 with compaction roll 70 heated to 130° C. to form substantially continuous bonds 80. Fibers of the fabric were further calendar bonded at calendar rolls 71, 73, with roll 73 being an engraved roll having raised portions 88 in the form of pins with 1.25 mm pin height and 0.62 mm open gap in a 10% point bonding pattern. The roll 73 was heated to 135 C to form point bonds 90 on second side 14 of fabric 10, as shown in FIG. 11.

The fabrics 10 of Examples 5 and 6 differed only in the absence or presence of point bonds 90. The second side 14 of the fabrics 10 underwent fuzz testing according to the Fuzz Level Test to determine the effectiveness of the point bonds in securing fibers to the surface of the fabric. The results of fuzz testing of Examples 5 and 6 are shown in Table 3.

TABLE 3

MD Fuzz Results

| Sample No. | MD Fuzz Value (mg/cm$^2$) |
| --- | --- |
| Example 5 | 0.36 |
| Example 6 | 0.19 |

As shown above, the point bonds 90 result in a dramatic decrease in the MD Fuzz Value. It retained its softness, absorbency, and aesthetic benefits in spite of the bonding treatment and now also has the desired resistance to fuzz upon consumer use.

Figure 27:
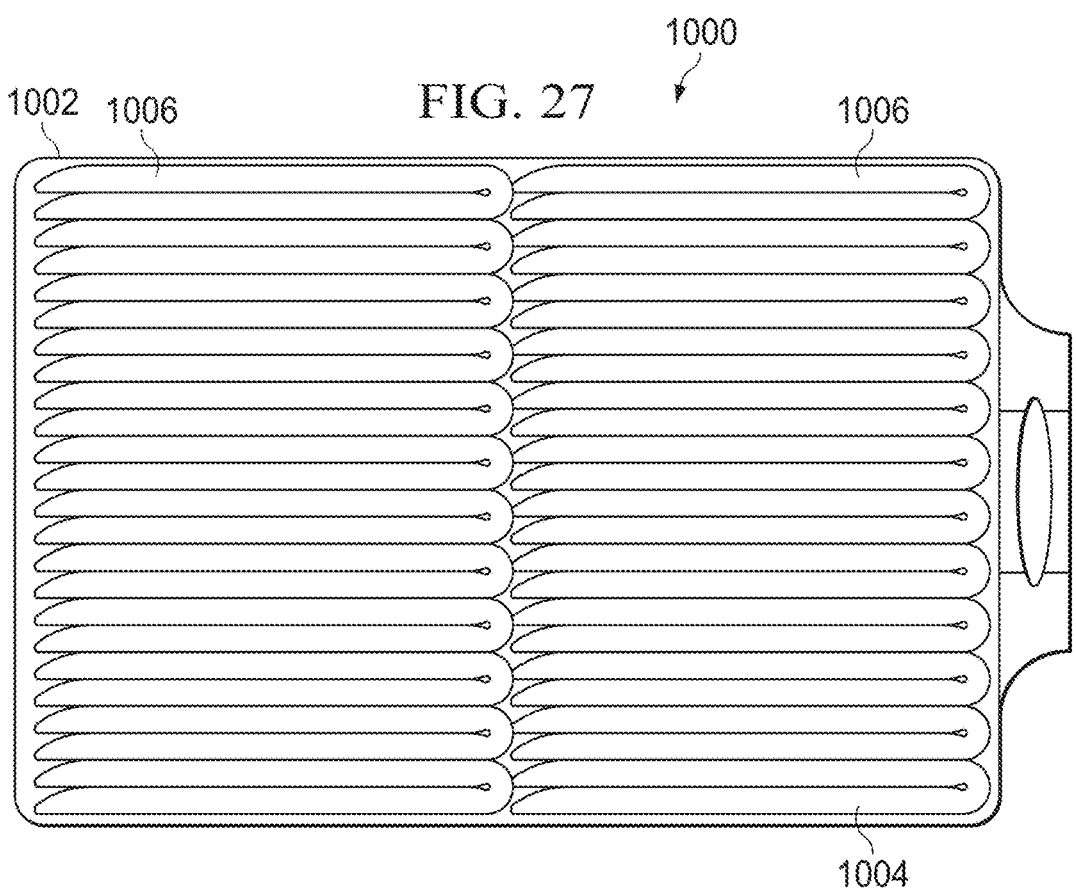
FIG. 27 is a schematic view of a package of the present disclosure.

Present disclosure absorbent articles are generally placed into packages for shipping, storing, and selling. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages. FIG. 27 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Packages of the absorbent articles of the present disclosure may have an In-Bag Stack Height of less than about 100 mm, less than about 95 mm, less than about 90 mm, less than about 85 mm, less than about 85 mm, but greater than about 75 mm, less than about 80 mm, less than about 78 mm, less than about 76 mm, or less than about 74 mm, specifically reciting all 0.1 mm increments within the specified ranges and all ranges formed therein or thereby, according to the In-Bag Stack Height Test described herein. Alternatively, packages of the absorbent articles of the present disclosure may have an in-Bag Stack Height of from about 70 mm to about 100 mm, from about 70 mm to about 95 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

General Description of an Absorbent Article

Figure 28:
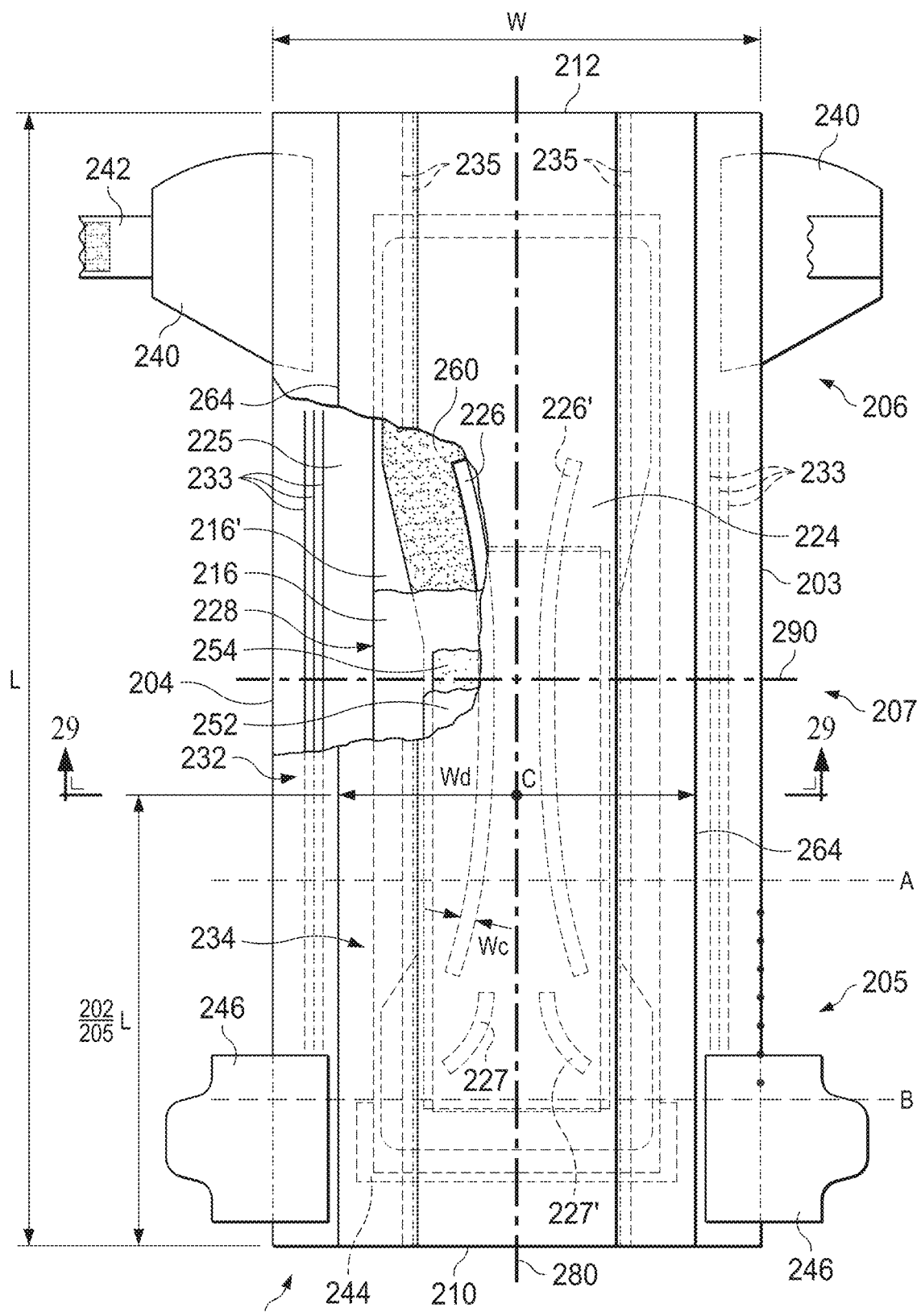
FIG. 28 is a plan view of an absorbent article of the present disclosure.
Figure 29:
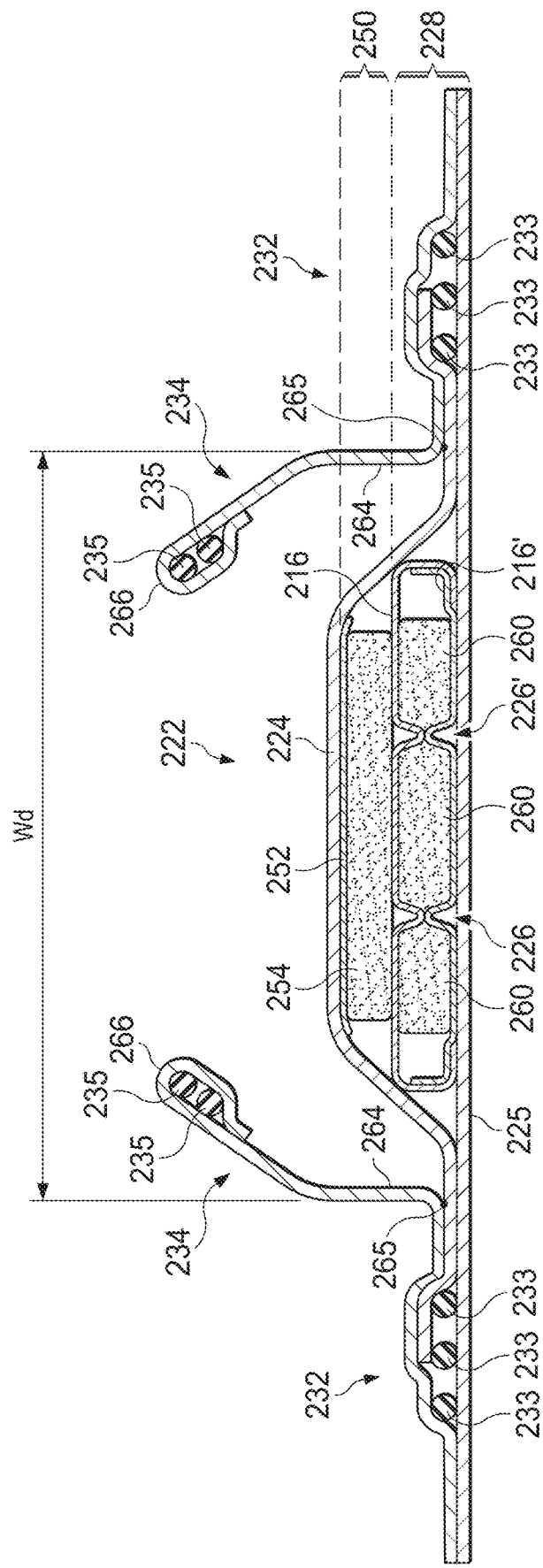
FIG. 29 is a plan view of an absorbent article of the present disclosure
Figure 30:
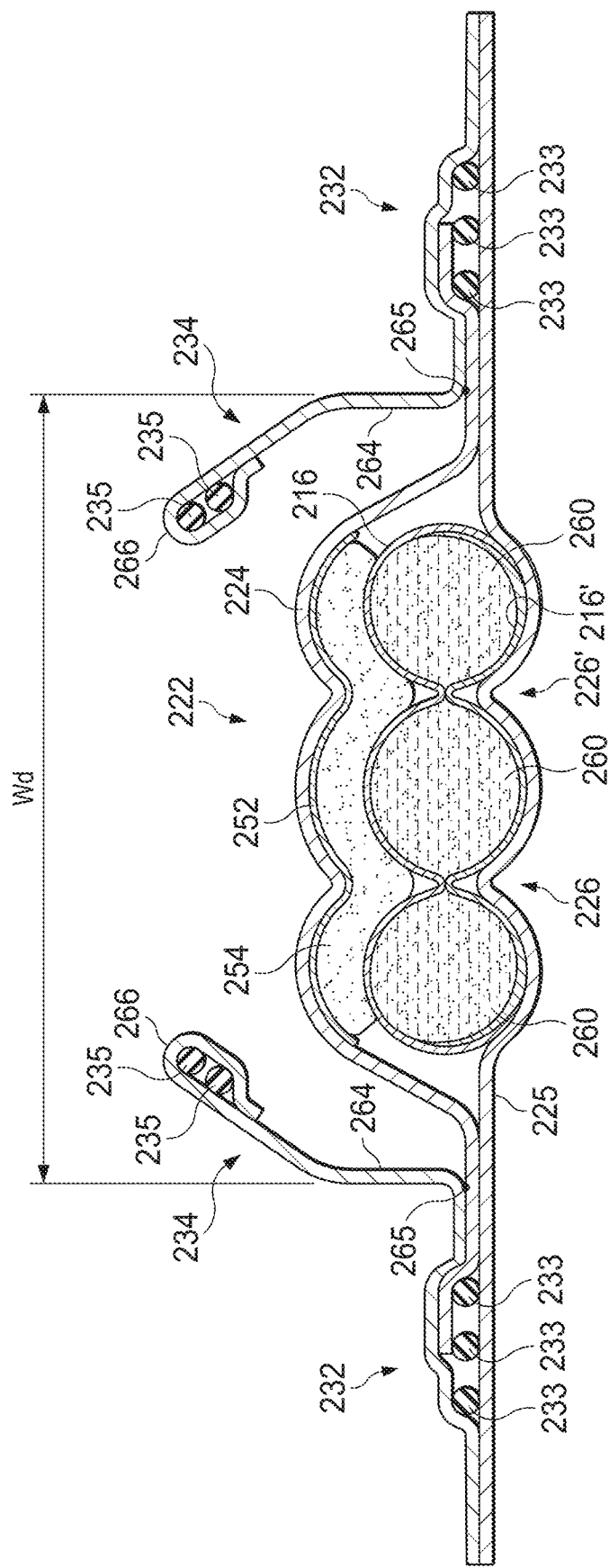
FIG. 30 is a cross sectional view of Section 29-29 of FIG. 28.

The three-dimensional nonwoven fabrics 10 of the present disclosure can be utilized as a component of absorbent articles, such as diapers, childcare items such as training pants, feminine care items such as sanitary napkins, and adult care items such as incontinence products, pads, and pants An example absorbent article in the form of a diaper 220 is represented in FIGS. 28-30. FIG. 28 is a plan view of the example diaper 220, in a flat, laid-out state, with portions of the structure being cut-away to more clearly show the construction of the diaper 220. The wearer-facing surface of the diaper 220 of FIG. 28 is facing the viewer. This diaper 220 is shown for illustration purpose only as the three-dimensional nonwoven materials of the present disclosure may be used as one or more components of an absorbent article, such as the topsheet, the acquisition layer, the topsheet and the acquisition layer, or the topsheet and the acquisition and/or the distribution system ("ADS"). In any event the three-dimensional nonwoven materials of the present disclosure may be liquid permeable.

The absorbent article 220 may comprise a liquid permeable material or topsheet 224, a liquid impermeable material or backsheet 225, an absorbent core 228 positioned at least partially intermediate the topsheet 224 and the backsheet 225, and barrier leg cuffs 234. The absorbent article may also comprise an ADS 250, which in the example represented comprises a distribution layer 254 and an acquisition layer 252, which will be further discussed below. The absorbent article 220 may also comprise elasticized gasketing cuffs 232 comprising elastics 233 joined to a chassis of the absorbent article, typically via the topsheet and/or backsheet, and substantially planar with the chassis of the diaper.

Figure 31:
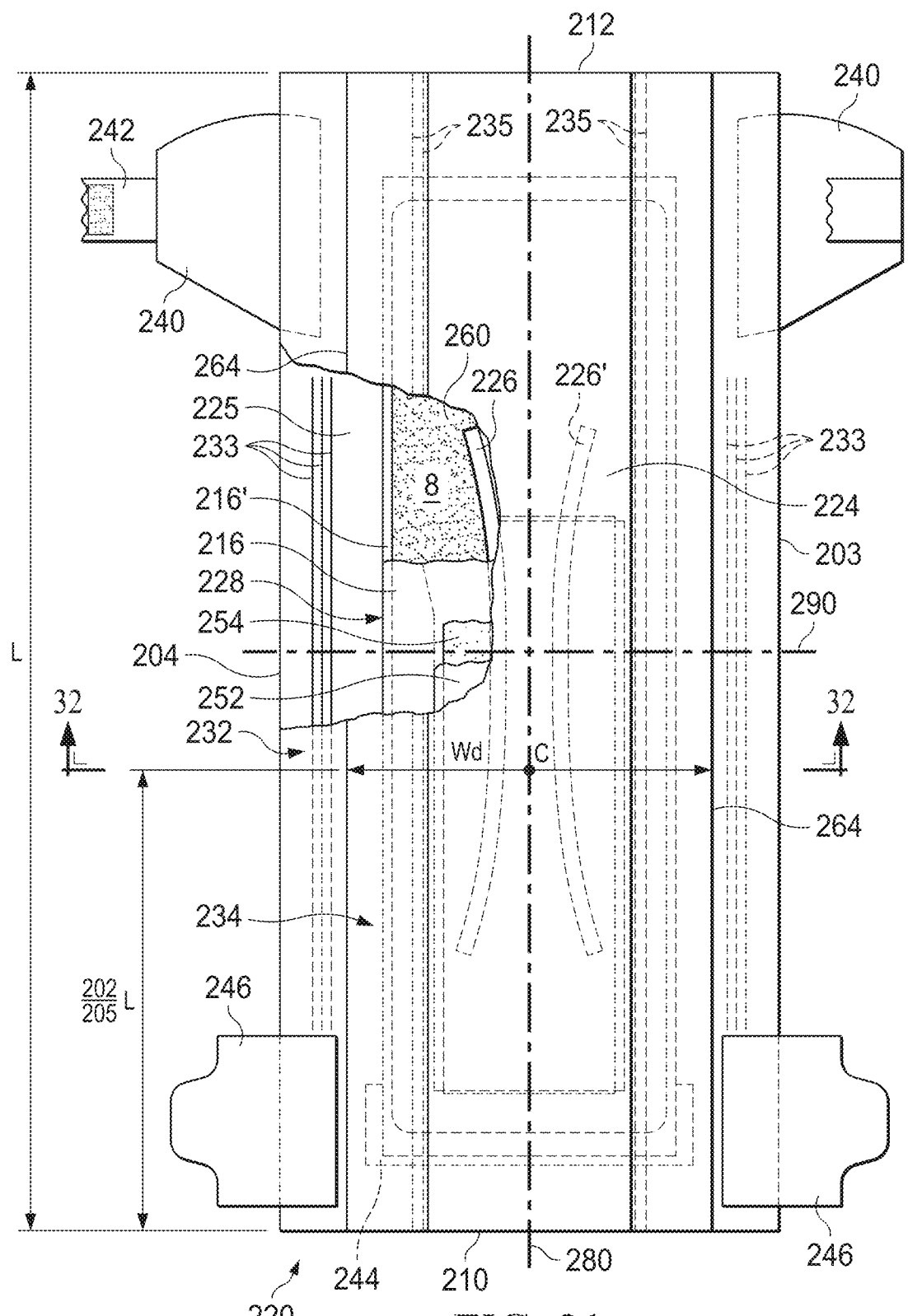
FIG. 31 is a plan view of an absorbent article of the present disclosure.

FIGS. 28 and 31 also show typical taped diaper components such as a fastening system comprising tabs 242 attached towards the rear edge of the article and cooperating with a landing zone 244 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 220 comprises a front waist edge 210, a rear waist edge 212 longitudinally opposing the front waist edge 210, a first side edge 203, and a second side edge 204 laterally opposing the first side edge 203. The front waist edge 210 is the edge of the article which is intended to be placed towards the front of the user when worn, and the rear waist edge 212 is the opposite edge. The absorbent article 220 may have a longitudinal axis 280 extending from the lateral midpoint of the front waist edge 210 to a lateral midpoint of the rear waist edge 212 of the article and dividing the article in two substantially symmetrical halves relative to the longitudinal axis 280, with the article placed flat, laid-out and viewed from above as in FIG. 28. The absorbent article 220 may also have a lateral axis 290 extending from the longitudinal midpoint of the first side edge 203 to the longitudinal midpoint of the second side edge 204. The length. L. of the article may be measured along the longitudinal axis 280 from the front waist edge 210 to the rear waist edge 212. The width, W, of the absorbent article may be measured along the lateral axis 290 from the first side edge 203 to the second side edge 204. The absorbent article may comprise a crotch point C defined herein as the point placed on the longitudinal axis at a distance of two fifth (⅖) of L starting from the front edge 210 of the article 220. The article may comprise a front waist region 205, a rear waist region 206, and a crotch region 207. The front waist region 205, the rear waist region 206, and the crotch region 207 may each define ⅓ of the longitudinal length, L, of the absorbent article.

The topsheet 224, the backsheet 225, the absorbent core 228, and the other article components may be assembled in a variety of configurations, in particular by gluing or heat embossing, for example.

The absorbent core 228 may comprise an absorbent material comprising at least 80% by weight, at least 85% by weight, at least 90% by weight, at least 95% by weight, or at least 99% by weight of superabsorbent polymers, and a core wrap enclosing the superabsorbent polymers. The core wrap may typically comprise two materials, substrates, or nonwoven materials 216 and 216' for the top side and the bottom side of the core. These types of cores are known as airfelt-free cores. The core may comprise one or more channels, represented in FIG. 28 as the four channels 226, 226' and 227, 227'. The channels 226, 226', 227, and 227' are optional features. Instead, the core may not have any channels or may have any number of channels.

These and other components of the example absorbent articles will now be discussed in more details.

Topsheet

In the present disclosure, the topsheet (the portion of the absorbent article that contacts the wearer's skin and receives the fluids) may be formed of a portion of, or all of, one or more of the three-dimensional nonwoven materials described herein and/or have one or more of the nonwoven materials positioned thereon and/or joined thereto, so that the nonwoven material(s) contact(s) the wearer's skin. Other portions of the topsheet (other than the three-dimensional nonwoven materials) may also contact the wearer's skin. The three-dimensional nonwoven materials may be positioned as a strip or a patch on top of the typical topsheet 224. Alternatively, the three-dimensional nonwoven material may only form a central CD area of the topsheet. The central CD area may extend the full MD length of the topsheet or less than the full MD length of the topsheet.

The topsheet 224 may be joined to the backsheet 225, the absorbent core 228 and/or any other layers as is known to those of skill in the art. Usually, the topsheet 224 and the backsheet 225 are joined directly to each other in some locations (e.g., on or close to the periphery of the absorbent article) and are indirectly joined together in other locations by directly joining them to one or more other elements of the article 220.

The topsheet 224 may be compliant, soft-feeling, and non-irritating to the wearer's skin. Further, a portion of, or all of, the topsheet 224 may be liquid permeable, permitting liquids to readily penetrate through its thickness. Furthermore, a portion of, or all of, the topsheet 224 may be treated with surfactants or other agents to either hydrophilize the web or make it hydrophobic. Any portion of the topsheet 224 may be coated with a lotion and/or a skin care composition as is generally disclosed in the art. The topsheet 224 may also comprise or be treated with antibacterial agents.

Backsheet

The backsheet 225 is generally that portion of the absorbent article 220 positioned adjacent the garment-facing surface of the absorbent core 228 and which prevents, or at least inhibits, the fluids and bodily exudates absorbed and contained therein from soiling articles such as bedsheets and undergarments. The backsheet 225 is typically impermeable, or at least substantially impermeable, to fluids (e.g., urine). The backsheet may, for example, be or comprise a thin plastic film such as a thermoplastic film having a thickness of about 0.012 mm to about 0.051 mm. Other suitable backsheet materials may include breathable materials which permit vapors to escape from the absorbent article 220, while still preventing, or at least inhibiting, fluids from passing through the backsheet 225.

The backsheet 225 may be joined to the topsheet 224, the absorbent core 228, and/or any other element of the absorbent article 220 by any attachment methods known to those of skill in the art.

The absorbent article may comprise a backsheet comprising an outer cover or an outer cover nonwoven. An outer cover or outer cover nonwoven of the absorbent article 220 may cover at least a portion of, or all of, the backsheet 225 to form a soft garment-facing surface of the absorbent article. The outer cover or outer cover nonwoven may be formed of the high loft, three-dimensional nonwoven materials described herein. Alternatively, the outer cover or outer cover nonwoven may comprise one or more known outer cover materials. If the outer cover comprises one of the three-dimensional nonwoven materials of the present disclosure, the three-dimensional nonwoven material of the outer cover may or may not match (e.g., same material, same pattern) a three-dimensional nonwoven material used as the topsheet or the topsheet and the acquisition layer of the absorbent article. In other instances, the outer cover may have a printed or otherwise applied pattern that matches or visually resembles the pattern of the three-dimensional nonwoven materials used as the topsheet or the topsheet and the acquisition layer laminate of the absorbent article. The outer cover may be joined to at least a portion of the backsheet 225 through mechanical bonding, ultrasonic, thermal bonding, adhesive bonding, or other suitable methods of attachment.

Absorbent Core

The absorbent core is the component of the absorbent article that has the most absorbent capacity and that comprises an absorbent material and a core wrap or core bag enclosing the absorbent material. The absorbent core does not include the acquisition and/or distribution system or any other components of the absorbent article which are not either integral part of the core wrap or core bag or placed within the core wrap or core bag. The absorbent core may comprise, consist essentially of, or consist of, a core wrap, an absorbent material (e.g., superabsorbent polymers and little or no cellulose fibers) as discussed, and glue.

The absorbent core 228 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The absorbent core may contain airfelt with or without superabsorbent polymers.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This airfelt-free core is relatively thin compared to a conventional core typically comprising between 40-60% SAP by weight and a high content of cellulose fibers. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

As referenced above, the airfelt-free cores with very little or no natural, cellulosic and/or synthetic fibers are quite thin compared to conventional cores, thereby making the overall absorbent article thinner than absorbent articles with cores comprising mixed SAP and cellulosic fibers (e.g., 40-60% cellulose fibers). This core thinness can lead to consumer perceptions of reduced absorbency and performance, although technically this is not the case. Presently, these thin cores have typically been used with substantially planer or apertured topsheets. Furthermore, absorbent articles having these thin airfelt-free cores have reduced capillary void space since there is little or no natural, cellulosic, or synthetic fibers in the cores. Thus, there may sometimes not be enough capillary void space in the absorbent article to fully accept multiple insults of bodily exudates or a single large insult.

To solve such problems, the present disclosure provides absorbent articles with these thin airfelt-free cores in combination with one of the high-loft, three-dimensional nonwoven materials described herein as a topsheet or as a topsheet and acquisition layer laminate. In such an instance, consumer perception of absorbency and performance, through the increased thickness of the absorbent article owing to the additional thickness provided by the high-loft, three-dimensional nonwoven material, is increased. Furthermore, the three-dimensional nonwoven materials, when used with these thin airfelt-free cores and as the topsheet or the topsheet and acquisition layer laminate, add capillary void space back into the absorbent articles, while still allowing for minimal stack heights, thereby passing cost savings onto consumers and manufactures. As such, the absorbent articles of the present disclosure may easily absorb multiple bodily exudate insults or single large insults owing to this increased capillary void space. Additionally, absorbent articles that comprise the nonwoven materials as the topsheet or the topsheet and acquisition layer laminate provide consumers with an aesthetically pleasing topsheet relative to a planer topsheet or an apertured topsheet with an increased thickness and thus the consumer perceptions of absorbency and performance.

Figure 32:
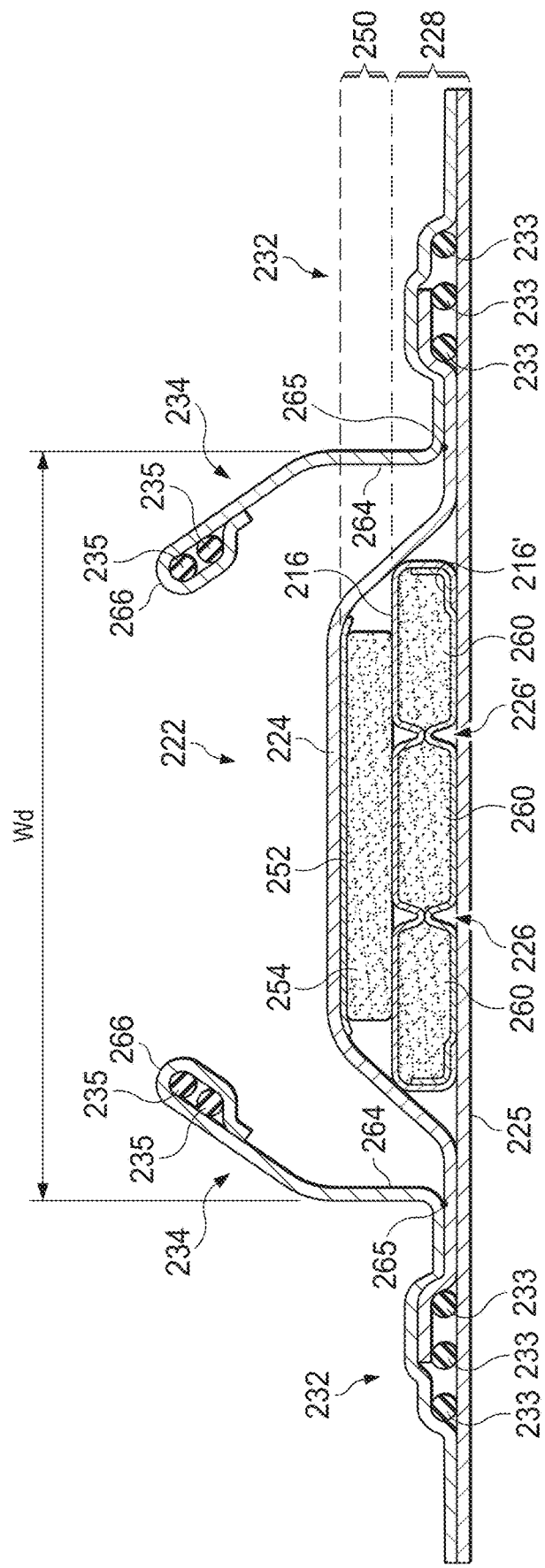
FIG. 32 is a cross sectional view of Section 32-32 of FIG. 31.
Figure 33:
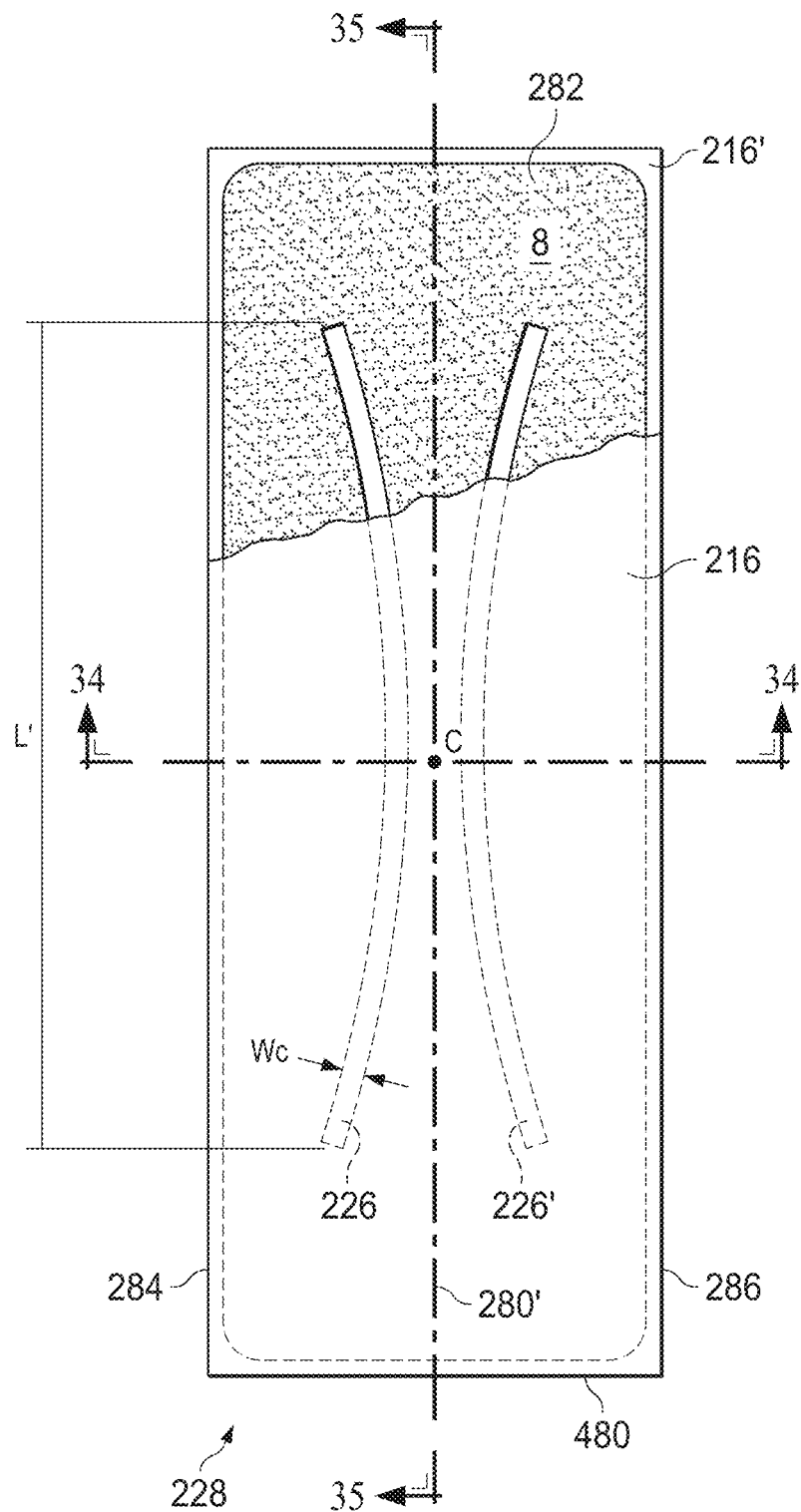
FIG. 33 is a plan view of an absorbent article of the present disclosure.
Figure 34:
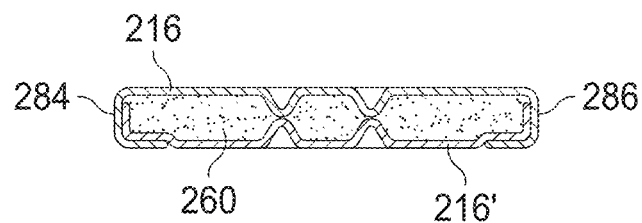
FIG. 34 is a cross sectional view of Section 34-34 of FIG. 33.
Figure 35:
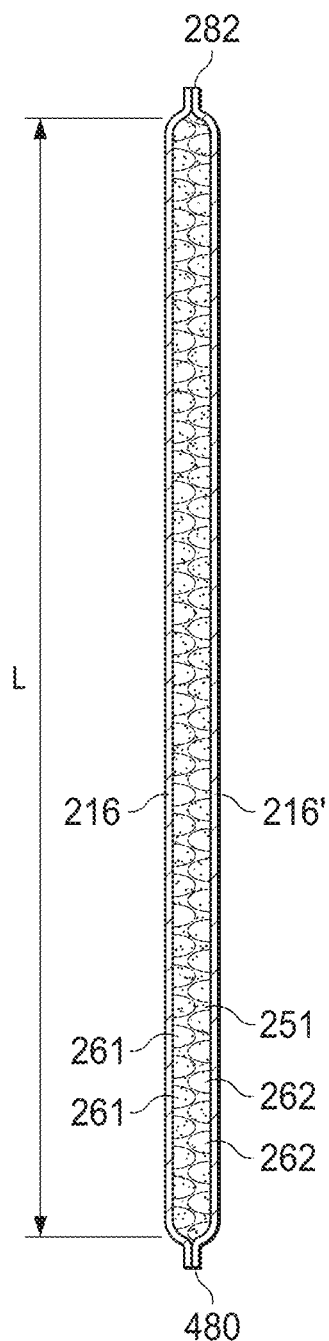
FIG. 35 is a cross sectional view of Section 35-35 of FIG. 33.

The example absorbent core 228 of the absorbent article 220 of FIGS. 31-32 is shown in isolation in FIGS. 33-35. The absorbent core 228 may comprises a front side 480, a rear side 282, and two longitudinal sides 284, 286 joining the front side 480 and the rear side 282. The absorbent core 228 may also comprise a generally planar top side and a generally planar bottom side. The front side 480 of the core is the side of the core intended to be placed towards the front waist edge 210 of the absorbent article. The core 228 may have a longitudinal axis 280' corresponding substantially to the longitudinal axis 280 of the absorbent article 220, as seen from the top in a planar view as in FIG. 28. The absorbent material may be distributed in higher amount towards the front side 480 than towards the rear side 282 as more absorbency may be required at the front in particular absorbent articles. The front and rear sides 480 and 282 of the core may be shorter than the longitudinal sides 284 and 286 of the core. The core wrap may be formed by two nonwoven materials, substrates, laminates, or other materials, 216, 216' which may be at least partially sealed along the sides 284, 286 of the absorbent core 228. The core wrap may be at least partially sealed along its front side 480, rear side 282, and two longitudinal sides 284, 286 so that substantially no absorbent material leaks out of the absorbent core wrap. The first material, substrate, or nonwoven 216 may at least partially surround the second material, substrate, or nonwoven 216' to form the core wrap, as illustrated in FIG. 34. The first material 216 may surround a portion of the second material 216' proximate to the first and second side edges 284 and 286.

The absorbent core may comprise adhesive, for example, to help immobilizing the SAP within the core wrap and/or to ensure integrity of the core wrap, in particular when the core wrap is made of two or more substrates. The adhesive may be a hot melt adhesive, supplied, by H.B. Fuller, for example. The core wrap may extend to a larger area than strictly needed for containing the absorbent material within.

The absorbent material may be a continuous layer present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 (Hundorf), for example. The absorbent core 228 may comprise a first absorbent layer and a second absorbent layer. The first absorbent layer may comprise the first material 216 and a first layer 261 of absorbent material, which may be 100% or less of SAP. The second absorbent layer may comprise the second material 216' and a second layer 262 of absorbent material, which may also be 100% or less of SAP. The absorbent core 228 may also comprise a fibrous thermoplastic adhesive material 251 at least partially bonding each layer of absorbent material 261, 262 to its respective material 216 or 216'. This is illustrated in FIGS. 34-35, as an example, where the first and second SAP layers have been applied as transversal stripes or "land areas" having the same width as the desired absorbent material deposition area on their respective substrate before being combined. The stripes may comprise different amounts of absorbent material (SAP) to provide a profiled basis weight along the longitudinal axis of the core 280. The first material 216 and the second material 216' may form the core wrap.

The fibrous thermoplastic adhesive material 251 may be at least partially in contact with the absorbent material 261, 262 in the land areas and at least partially in contact with the materials 216 and 216' in the junction areas. This imparts an essentially three-dimensional structure to the fibrous layer of thermoplastic adhesive material 251, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material, which may be 100% or less of SAP.

The thermoplastic adhesive used for the fibrous layer may have elastomeric properties, such that the web formed by the fibers on the SAP layer is able to be stretched as the SAP swell.

Superabsorbent Polymer (SAP)

The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 210 or rear waist edge 212 may therefore comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g. The average SAP basis weight within the (or "at least one", if several are present) deposition area 8 of the SAP may be at least 50, 100, 200, 300, 400, 500 or more g/m². The areas of the channels (e.g., 226, 226', 227, 227') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 29 and 34, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these.

The substrates may also be air-permeable (in addition to being liquid or fluid permeable). Films useful herein may therefore comprise micro-pores.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 216, 216', four seals may be used to enclose the absorbent material 260 within the core wrap. For example, a first substrate 216 may be placed on one side of the core (the top side as represented in FIGS. 33-35) and extend around the core's longitudinal edges to at least partially wrap the opposed bottom side of the core. The second substrate 216' may be present between the wrapped flaps of the first substrate 216 and the absorbent material 260. The flaps of the first substrate 216 may be glued to the second substrate 216' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are also within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 208 may be defined by the periphery of the layer formed by the absorbent material 260 within the core wrap, as seen from the top side of the absorbent core. The absorbent material deposition area 208 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 28. This may provide better wearing comfort. The absorbent material deposition area 8 may also be generally rectangular, for example as shown in FIGS. 31-33, but other deposition areas, such as a rectangular. "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 208 may comprise at least one channel 226, which is at least partially oriented in the longitudinal direction of the article 280 (i.e., has a longitudinal vector component) as shown in FIGS. 28 and 29. Other channels may be at least partially oriented in the lateral direction (i.e., has a lateral vector component) or in any other direction. In the following, the plural form "channels" will be used to mean "at least one channel". The channels may have a length L' projected on the longitudinal axis 280 of the article that is at least 10% of the length L of the article. The channels may be formed in various ways. For example, the channels may be formed by zones within the absorbent material deposition area 208 which may be substantially free of, or free of, absorbent material, in particular SAP. In another example, the channels may be formed by zones within the absorbent material deposition area 208 where the absorbent material of the core comprises cellulose, airfelt, SAP, or combinations thereof and the channels may be substantially free of, or free of, absorbent material, in particular the SAP, cellulose, or airfelt In addition or alternatively, the channel(s) may also be formed by continuously or discontinuously bonding the top side of the core wrap to the bottom side of the core wrap through the absorbent material deposition area 208. The channels may be continuous, but it is also envisioned that the channels may be intermittent. The acquisition-distribution system or layer 250, or another layer of the article, may also comprise channels, which may or not correspond to the channels of the absorbent core.

In some instances, the channels may be present at least at the same longitudinal level as the crotch point C or the lateral axis 260 in the absorbent article, as represented in FIG. 28 with the two longitudinally extending channels 226, 226'. The channels may also extend from the crotch region 207 or may be present in the front waist region 205 and/or in the rear waist region 206 of the article.

The absorbent core 228 may also comprise more than two channels, for example, at least 3, at least 4, at least 5, or at least 6 or more. Shorter channels may also be present, for example in the rear waist region 206 or the front waist region 205 of the core as represented by the pair of channels 227, 227' in FIG. 28 towards the front of the article. The channels may comprise one or more pairs of channels symmetrically arranged, or otherwise arranged relative to the longitudinal axis 280.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may be completely oriented longitudinally and parallel to the longitudinal axis or completely oriented transversely and parallel to the lateral axis, but also may have at least portions that are curved.

In order to reduce the risk of fluid leakages, the longitudinal main channels may not extend up to any of the edges of the absorbent material deposition area 208, and may therefore be fully encompassed within the absorbent material deposition area 208 of the core. The smallest distance between a channel and the closest edge of the absorbent material deposition area 208 may be at least 5 mm.

The channels may have a width We along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. When the channels are formed by absorbent material-free zone within the absorbent material deposition area 208, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 216 and the second substrate 216') and/or the topsheet 224 to the backsheet 225 together through the channels. Typically, an adhesive may be used to bond both sides of the core wrap or the topsheet and the backsheet through the channels, but it is possible to bond via other known processes, such as pressure bonding, ultrasonic bonding, heat bonding, or combination thereof. The core wrap or the topsheet 224 and the backsheet 225 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 34. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 224 and/or the backsheet 225 and a free terminal edge 266, which is intended to contact and form a seal with the wearer's skin. The barrier leg cuffs 234 extend at least partially between the front waist edge 210 and the rear waist edge 212 of the absorbent article on opposite sides of the longitudinal axis 280 and are at least present at the level of the crotch point (C) or crotch region. The barrier leg cuffs may be joined at the proximal edge 264 with the chassis of the article by a bond 265 which may be made by gluing, fusion bonding, or a combination of other suitable bonding processes. The bond 265 at the proximal edge 264 may be continuous or intermittent. The bond 265 closest to the raised section of the leg cuffs delimits the proximal edge 264 of the standing up section of the leg cuffs.

The barrier leg cuffs may be integral with the topsheet 224 or the backsheet 225 or may be a separate material joined to the article's chassis. Each barrier leg cuff 234 may comprise one, two or more elastic strings 235 close to the free terminal edge 266 to provide a better seal.

In addition to the barrier leg cuffs 234, the article may comprise gasketing cuffs 232, which are joined to the chassis of the absorbent article, in particular to the topsheet 224 and/or the backsheet 225 and are placed externally relative to the barrier leg cuffs. The gasketing cuffs 232 may provide a better seal around the thighs of the wearer. Each gasketing leg cuff may comprise one or more elastic strings or elastic elements 233 in the chassis of the absorbent article between the topsheet 224 and backsheet 225 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 250 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 254 and an acquisition layer 252 disposed between the absorbent core and the topsheet, but the present disclosure is not so limited.

In one example, the high loft, three-dimensional nonwoven materials of the present disclosure may comprise the topsheet and the acquisition layer as a laminate. A distribution layer may also be provided on the garment-facing side of the topsheet/acquisition layer laminate.

Carrier Layer

In an instance where the high loft, three-dimensional nonwoven materials of the present disclosure encompass a topsheet and acquisition layer laminate, the distribution layer may need to be supported by a carrier layer (not illustrated) that may comprise one or more nonwoven materials or other materials. The distribution layer may be applied to or positioned on the carrier layer. As such, the carrier layer may be positioned intermediate the acquisition layer and the distribution layer and be in a facing relationship with the acquisition layer and the distribution layer.

Distribution Layer

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents).

Acquisition Layer

If a three-dimensional nonwoven material of the present disclosure is provided as only the topsheet of an absorbent article, the ADS 250 may comprise an acquisition layer 252. The acquisition layer may be disposed between the distribution layer 254 and the topsheet 224. In such an instance, the acquisition layer 252 may be or may comprise a nonwoven material, such as a hydrophilic SMS or SMMS material, comprising a spunbonded, a melt-blown and a further spunbonded layer or alternatively a carded staple fiber chemical-bonded nonwoven. The nonwoven material may be latex bonded.

Fastening System

The absorbent article may comprise a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 244 is normally provided on the garment-facing surface of the front waist region 205 for the fastener to be releasably attached thereto.

Front and Rear Ears

The absorbent article may comprise front ears 246 and rear ears 240. The ears may be an integral part of the chassis, such as formed from the topsheet 224 and/or backsheet 226 as side panels. Alternatively, as represented on FIG. 28, the ears may be separate elements attached by gluing, heat embossing, and/or pressure bonding. The rear ears 240 may be stretchable to facilitate the attachment of the tabs 242 to the landing zone 244 and maintain the taped diapers in place around the wearer's waist. The rear ears 240 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 220 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 228 and generally forms at least a portion of the end edge of the absorbent article. Disposable diapers may be constructed so as to have two elastic waist features, one positioned in the front waist region and one positioned in the rear waist region.

Color Signals

In a form, the absorbent articles of the present disclosure may have different colors in different layers, or portions thereof (e.g., the topsheet and the acquisition layer, the topsheet and the nonwoven core cover, a first portion and a second portion of a topsheet, a first portion and second portion of the acquisition layer). The different colors may be shade of the same color (e.g., dark blue and light blue) or may be actual different colors (e.g., purple and green). The different colors may have a Delta E in the range of about 1.5 to about 10, about 2 to about 8, or about 2 to about 6, for example. Other Delta E ranges are also within the scope of the present disclosure.

In an instance, various layers of the absorbent articles may be joined using a colored adhesive. The colored adhesive may be laid down on any suitable layer or layers in a pattern. The pattern of the adhesive may or may not complement the pattern of the topsheet. Such a pattern may increase the appearance of depth in an absorbent article. In certain instances, the colored adhesive may be blue.

In other instances, any of the layers may comprise indicia, such as a printed ink to aid in the appearance, depth impression, absorbency impression, or quality impression of the absorbent articles.

In other instances, the colors may be complimentary, or registered with, the patterns of three-dimensional features of the nonwoven fabric 10 utilized as a component in an absorbent article. For example, a fabric having first and second zones of visually distinct patterns of three-dimensional features may also have printed thereon color to emphasize, highlight, contrast with, or otherwise change the visual appearance of the fabric 10. The color enhancements can be beneficial in communicating to a user of an absorbent article certain functional characteristics of the nonwoven fabric 10 when in use. Thus color can be used in combination with structural, three-dimensional features in one component, or in combinations of components to deliver a visually distinctive absorbent article. For example, a secondary topsheet or acquisition layer may have printed thereon a pattern of color or colors that compliments the pattern of three-dimensional features of a fabric 10 utilized as a topsheet in an absorbent article. Another example is an absorbent article comprising 1) an absorbent core comprising a channel, 2) a topsheet with a three dimensional pattern registered or highlighting the channel or channels in the core, and 3) a graphic, colored component, printed ink, or indicia visible from the topsheet viewing (body contacting surface) or the backsheet viewing surface (garment facing surface) to further emphasize the functional features of the core channel or channels and the overall performance of the absorbent article.

Further characterization of the novel aspects of the present disclosure can be realized by focusing on the three-dimensional features within a visually discernible zone. Each zone, such as Zones 110, 120, and 130, discussed above, can be described further with respect to microzones. A microzone is a portion of the nonwoven fabric 10 within a zone, that has at least two visually discernible regions and there is a common intensive property difference between these two regions. A microzone may comprise a portion of the nonwoven fabric 10 which crosses two or more zone boundaries that has at least two visually discernible regions and there is a common intensive property difference between these two regions The benefit of considering microzones in the present disclosure is to illustrate that in addition to differences in average intensive properties with a zone, such as zones 110, 120, and 130, as discussed above, the present disclosure also provides for fabrics having differences in actual and/or average intensive properties between regions defined by the three-dimensional features within a zone, with the three-dimensional features precisely placed according to the design of the forming belt used to produce the fabrics. The difference between intensive properties between regions of the three-dimensional features provides for additional visual as well as functional benefits. The sharp visual contrast between regions can provide for extremely fine visually distinctive designs within a zone and between zones. Likewise, the precise placement of regions afforded by the precisely manufactured forming belt can provide for excellent and tailored softness, strength, and fluid handling properties of the zones. Thus, the invention in one embodiment provides for the combination of differences in average intensive properties between zones and simultaneously differences in intensive properties of the regions making up a microzone.

Figure 38:
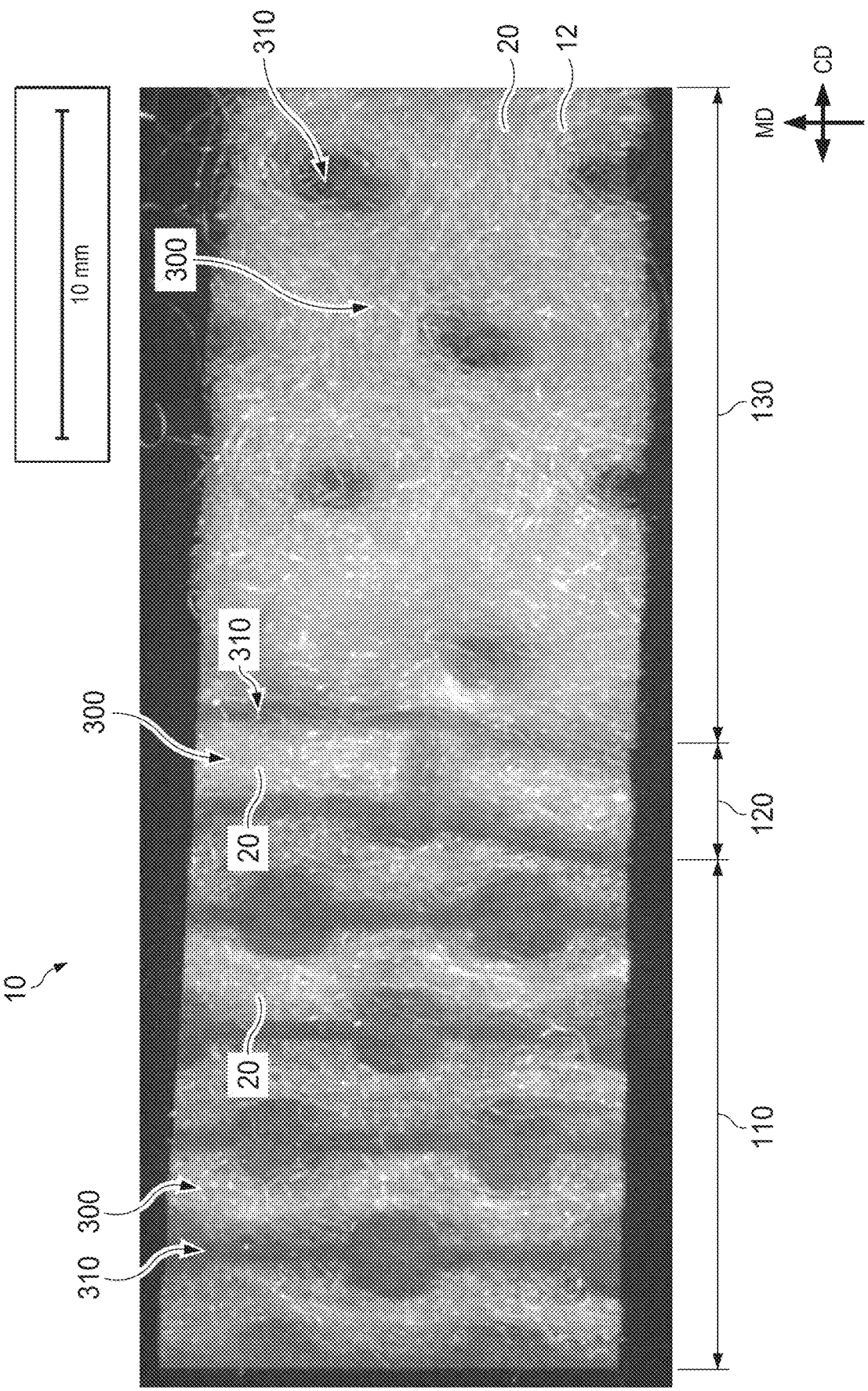
FIG. 38 is a photograph of an example of a shaped nonwoven of the present disclosure.
Figure 39:
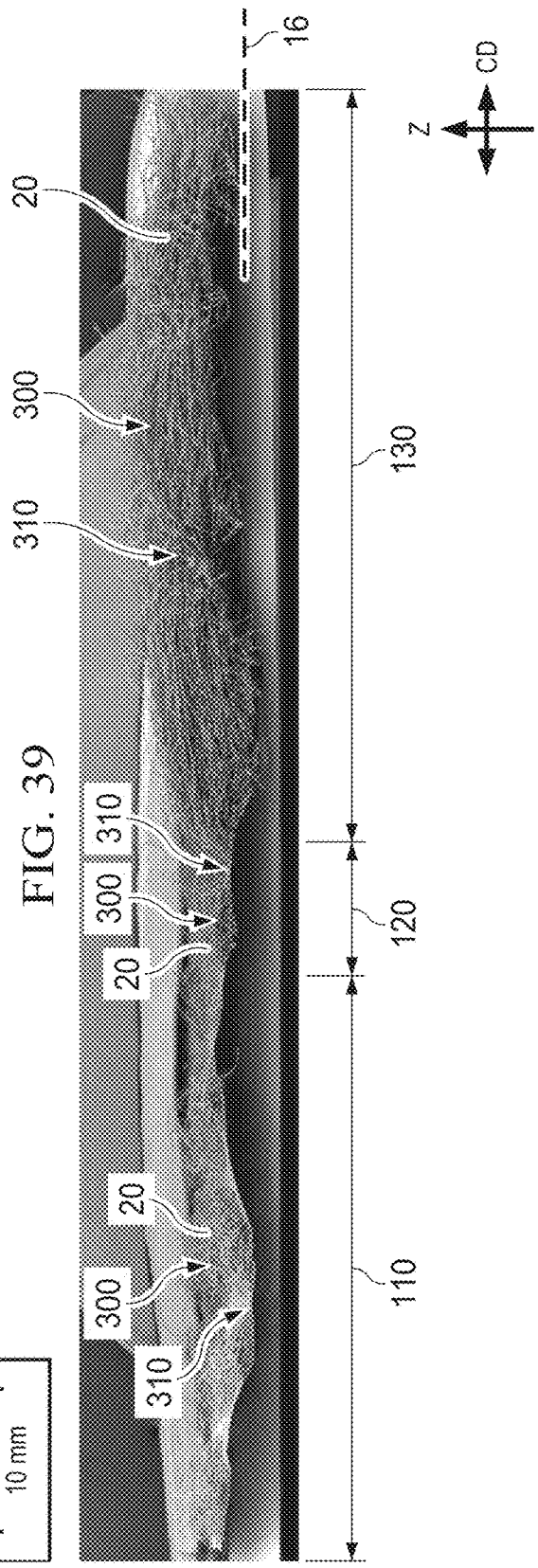
FIG. 39 is a photograph of cross section of the example shown in FIG. 38.

Regions defined by three-dimensional features can be understood with reference to FIG. 38 and FIG. 39. FIG. 38 shows a light microscope image of a portion of a fabric 10 according to the present disclosure, and FIG. 39 is a scanning electron micrograph (SEM) of a cross-section of the portion of the fabric shown in FIG. 38. Thus. FIGS. 38 and 39 show a portion of a nonwoven fabric 10 magnified for more precise description of the otherwise visually discernible features of the fabric. The portion of the nonwoven fabric 10 shown in FIG. 38 is approximately 36 mm in the CD and exhibits portions of at least three visually distinct zones as discussed below.

In FIGS. 38 and 39 which show a portion of one pattern of a nonwoven fabric 10, a first zone 110 (on the left side of FIG. 38) is characterized by generally MD-oriented rows of variable width first regions 300 separated by MD-oriented rows of variable width second regions 310. The first region is also the three-dimensional feature 20 that defines the first and second regions 300, 310. In an embodiment, a three-dimensional feature is a portion of the nonwoven fabric 10 that was formed between or around a raised element of the forming belt, which in this description is the first region 300, such that the resulting structure has a relatively greater dimension in the Z-direction. The adjacent second region 310 generally has a common intensive property with first region 300, and in an embodiment has relatively lower thickness values, i.e., lesser dimension in the Z-direction. The relative dimensions in the Z direction with respect to a plane of the first surface 16 as described above, can be seen in FIG. 39. Absolute dimensions are not critical; but the dimensional differences can be visually discernible on the nonwoven fabric 10 without magnification.

The invention of the disclosure permits beneficial characteristics best expressed with respect to the regions defined by three-dimensional features in microzones. For example, as shown in FIG. 38, in zone 110 for each three dimensional features 20 there is a visible distinction between a first region 300 and a second region 310. As stated above, the visible distinction can exist in the nonwoven fabric 10 without magnification; the magnified views used herein are for purposes of clear disclosure. Any area that extends across the boundary between enough of first region 300 and second region 310 such that a difference in their respective intensive properties can be ascertained within the area can be a microzone. Additionally, light microscopy or microCT imagery of a structure can also be used to establish the location of regions and the area of a microzone.

The portion of nonwoven fabric 10 shown in FIG. 38 further illustrates another beneficial characteristic of the fabric 10, in that the differences in intensive properties between adjacent regions can be differences across zones. Thus, a microzone that spans an area encompassing second region 310 of zone 120 and first region 300 of zone 130 can be identified. In certain embodiments, including in the nonwoven fabric 10 shown in FIGS. 38 and 39, the difference in intensive properties exhibited by regions in microzones that a zone boundary can be significantly different in magnitude than the differences between intensive properties exhibited by regions within a zone.

Regardless of which zone, or which zonal boundary a particular microzone encompasses, the three-dimensional features can be characterized by the differences between intensive properties of the regions defined by them. In general, the nonwoven of the present disclosure can be a spunbond nonwoven fabric having a first surface defining a plane of the first surface. The fabric can have a plurality of three-dimensional features, each three dimensional feature defining a first region and a second region, the regions having a common intensive property that has a different value between them. In an embodiment, the first region can be distinguished as being at a higher elevation than the second region with respect to the plane of the first surface, hence exhibiting a difference in each region's common intensive property of thickness. The two regions can also be distinguished as having different densities, basis weights, and volumetric densities. That is, the two regions can be distinguished within a micro zone of the spunbond nonwoven fabric as being different with respect to common intensive properties, including properties such as thickness, density, basis weight, and volumetric density. In an embodiment one or both regions of a microzone can be fluid permeable. In an embodiment, the higher density region of a microzone can be fluid permeable.

Within zone 110 of the portion of fabric shown in FIG. 38, for example, there can be three-dimensional features 20 defining at least two regions, a first region 300 and a second region 310. The difference in thickness, basis weight, and volumetric density between the first and second regions for zone 110 shown in FIG. 38 can be 274 microns, 1 gsm, and 0.437 g/cc, respectively.

Likewise, within zone 130 of the portion of fabric shown in FIG. 38, for example, there can be three-dimensional features 20 defining at least two regions, a first region 300 and a second region 310. The difference in thickness, basis weight, and volumetric density between the first and second regions for zone 130 shown in FIG. 38 can be 2083 microns, 116 gsm, and 0.462 g/cc, respectively.

Additionally, within zone 120 of the portion of fabric shown in FIG. 38, for example, there can be three-dimensional features 20 defining at least two regions, a first region 300 and a second region 310. The difference in thickness, basis weight, and volumetric density between the first and second regions for the portion of fabric shown in FIG. 38 can be 204 microns, 20 gsm, 0.53 g/cc, respectively. In the embodiment shown, zone 120 forms what appears in an unmagnified view of nonwoven fabric 10 to be a stitched boundary between zones 110 and 130.

Further, a zone that encompasses the boundary between zones 120 and 130 of the portion of fabric shown in FIG. 38, for example, there are at least two regions, a first region 300 in zone 130 and a second region 310 in zone 120. The difference in thickness, basis weight, and volumetric density between the first and second regions for the portion of fabric shown in FIG. 38 can be 2027 microns, 58 gsm, and 0.525 g/cc, respectively.

Figure 42:
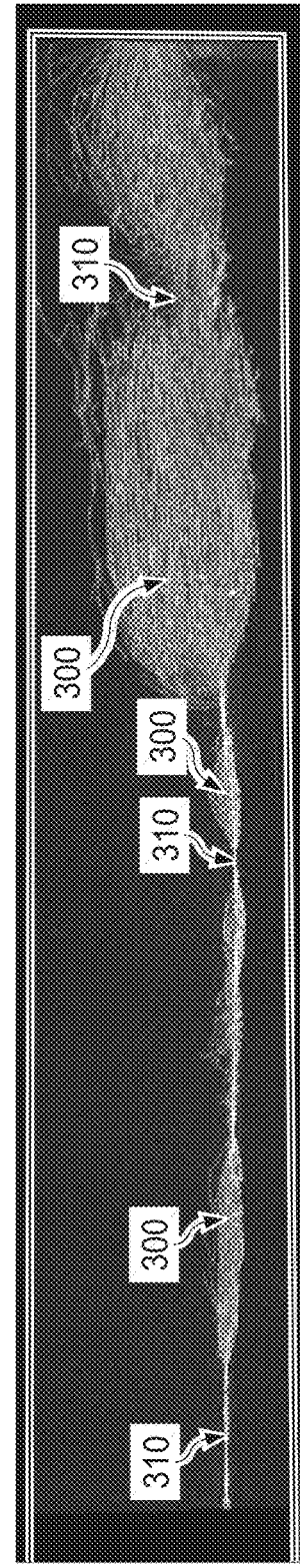
FIG. 42 is a Micro CT image of a cross section of the example shown in FIGS. 40 and 41.

Microzones are discussed in more detail with reference to FIGS. 40-42 and the data depicted in FIG. 44. FIGS. 40-42 are Micro-CT scans of a portion of a nonwoven fabric 10 similar in pattern to that of the nonwoven fabric 10 shown in FIG. 38. The Micro-CT scan permits description of the same features as shown in FIG. 38 in a slightly different manner and in a way that permits very precise measurement of intensive properties.

As shown in FIG. 40, zones 110, 120, and 130 are clearly visible, with their respective three-dimensional features 20. As depicted in FIGS. 40 and 41, the three-dimensional features are the dark-colored portions, with the dark color also representing the first region 300 of a three-dimensional feature 20, and the adjacent light-colored portions being the second region 310 for the three-dimensional feature 20.

The Micro-CT scan permits the image to be "cut" and cross-sectioned, as shown by the cut plane 450 in FIG. 41. A cut plane can be placed anywhere on the image; for the purposes of the present disclosure, the cut plane 450 cuts a cross section substantially parallel to the Z axis so as to produce the cross-sectional image in FIG. 42.

The Micro-CT technology permits intensive properties to be precisely and directly measured. Thickness measurements can be made directly from imaged cross sections based on the scale magnification, such as the cross section shown in FIG. 42. Further, the color differential between first regions and second regions is representative and proportional to differences in basis weight, volumetric density, and other intensive properties, which can likewise be directly measured. Micro-CT methodology is explained below in the Test Methods section.

Figure 43:
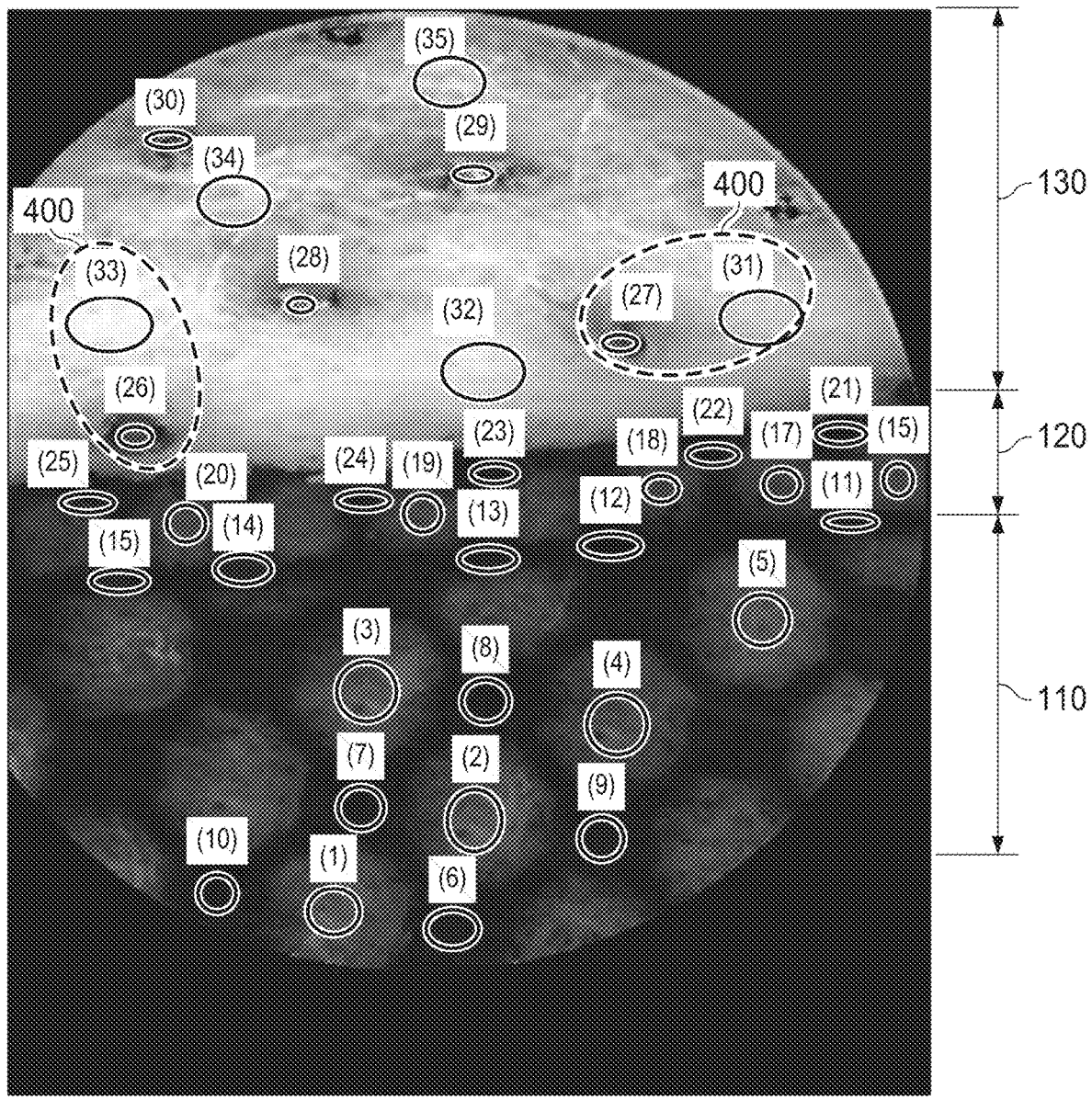
FIG. 43 is a Micro CT plan view image of the example shown in FIGS. 40 and 41.

FIG. 43 is a Micro-CT scan image of the portion of nonwoven fabric 10 shown in FIGS. 40 and 41. Utilizing, for specific first and second regions shown as numbered portions of the nonwoven fabric 10 can be analyzed. In FIG. 43, specific regions were manually selected and analyzed to measure thickness, basis weight, and volumetric density, and the data is produced in FIG. 44.

Figure 44:
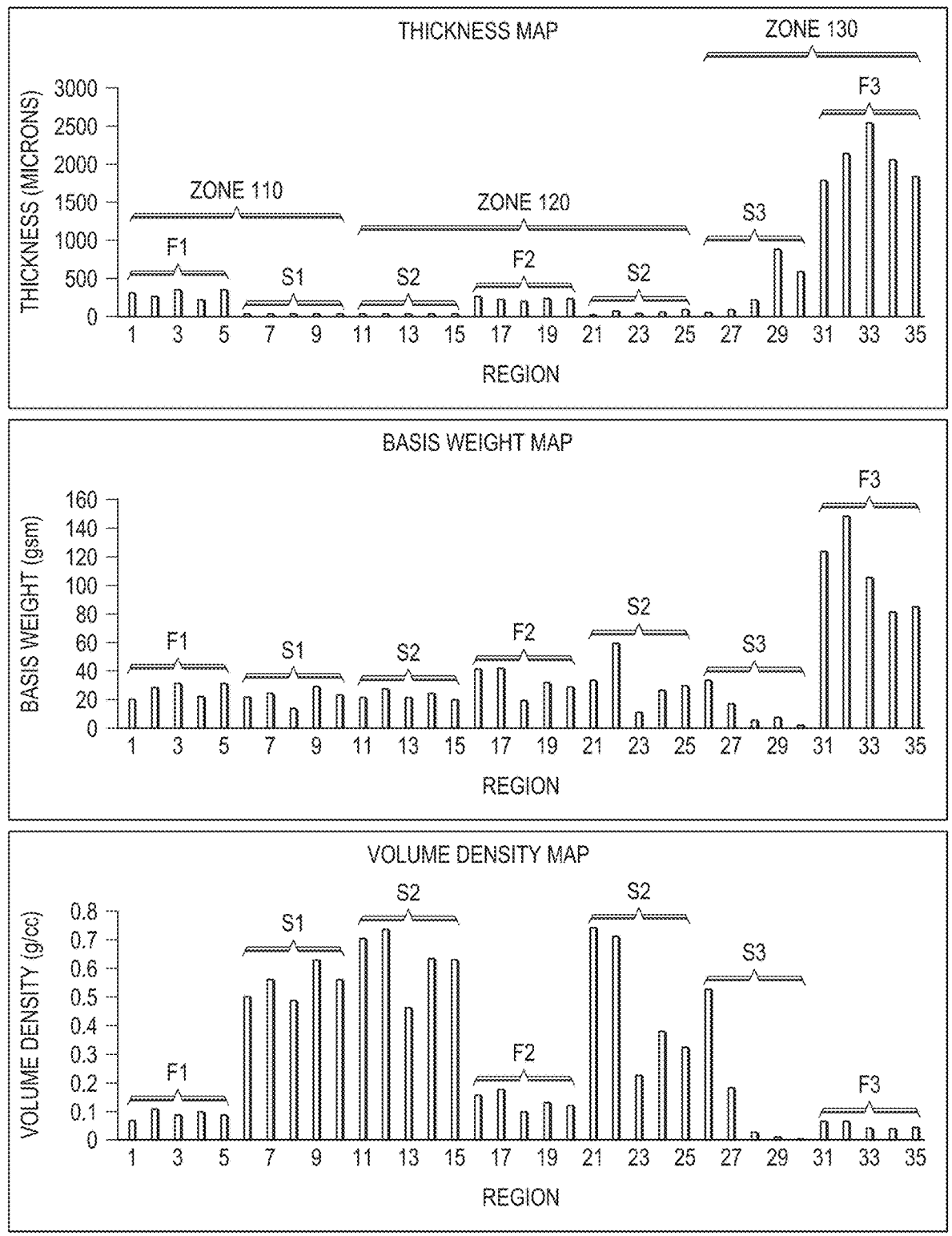
FIG. 44 is a graphical depiction of various benefits of a shaped nonwoven of the present disclosure.

FIG. 44 shows data for groupings of first and second region measurements made within the three zones depicted in FIG. 44. The x-axis is the regions, with the numbers corresponding to the numbered regions on FIG. 43. First region measurements are labeled as Fn (e.g., F1) and second regions measurements are labeled as Sn (e.g., S1). Thus, regions 1-5 are first regions F1, each being in zone 110. Regions 6-10 are second regions S1, also being in zone 110. Likewise, first regions F2 are regions 16-20 in zone 120, and regions 11-15 and 21-25 are second regions S2 in zone 120. Finally, regions 31-35 are first regions F3 in zone 130 and regions 26-30 are second regions S2 in zone 130. The numbered regions are consistently depicted across all three graphs of FIG. 44, but for simplicity, the zones 110, 120, and 130 are depicted only on the Thickness Map.

The graphs shown in FIG. 44 represent graphically the magnitude of difference in intensive properties between first regions and second regions within any one of the zones, and can be used to see graphically the difference in intensive properties for pairs of regions making up a microzone. For example, one can see that in zone 110 that basis weight between the two regions can be substantially the same, but the thickness (caliper) can vary from about 400 microns in the first regions to about 40 microns in the second regions, or about a 10× differential. The volumetric density in zone 110 can vary from about 0.1 g/cc to about 0.6 g/cc. Similar quantifiable distinctions can be understood for each of the zones shown.

Thus, with reference to FIG. 43 and FIG. 44 together, further characterization of the beneficial structure of a fabric 10 of the present disclosure can be understood. The nonwoven fabric 10 can be described as having at least two visually distinct zones, e.g., zones 110 and 120, with each of the zones having a pattern of three-dimensional features, each of the three-dimensional features defining a microzone comprising first and second regions, e.g., regions 300, 310, and wherein the difference in values for at least one of the microzones in the first zone is quantifiably different from the difference in values for at least one of the microzones in the second zone. For example, in FIG. 43, two representative microzones 400 in zone 130 are designated as the pair of regions marked as areas 31 and 27 and 33 and 26. That is, first region 31 and second region 27 form a microzone, and first region 33 and second region 26 form a microzone. Likewise, two representative microzones 400 in zone 120 are designated as the pair of regions marked as areas 19 and 24 and 17 and 22. From FIG. 44, Tables 4-7 can be populated as shown:

TABLE 4

Illustrative examples of differences in thickness in microzones

|  |  |  | Thickness (microns) | Difference in Thickness (microns) |
|---|---|---|---|---|
| Zone 130 | Microzone 1 | First Region 31 | 1802 | 1709 |
|  |  | Second Region 27 | 93 |  |

TABLE 4-continued

Illustrative examples of differences in thickness in microzones

|  |  |  | Thickness (microns) | Difference in Thickness (microns) |
|---|---|---|---|---|
|  | Microzone 2 | First Region 33 | 2548 | 2484 |
|  |  | Second Region 26 | 64 |  |
| Zone 120 | Microzone 1 | First Region 19 | 242 | 172 |
|  |  | Second Region 24 | 70 |  |
|  | Microzone 2 | First Region 17 | 235 | 183 |
|  |  | Second Region 23 | 52 |  |

TABLE 5

Illustrative examples of differences in basis weight in microzones

|  |  |  | Basis weights (gsm) | Difference in Basis weights (gsm) |
|---|---|---|---|---|
| Zone 130 | Microzone 1 | First Region 31 | 124 | 107 |
|  |  | Second Region 27 | 17 |  |
|  | Microzone 2 | First Region 33 | 106 | 72 |
|  |  | Second Region 26 | 34 |  |
| Zone 120 | Microzone 1 | First Region 19 | 32 |  |
|  | Microzone 2 | Second Region 24 | 27 | 5 |
|  |  | First Region 17 | 42 | 30 |
|  |  | Second Region 23 | 12 |  |

TABLE 6

Illustrative examples of differences in volumetric density in microzones

|  |  |  | Volumetric Density (g/cc) | Difference in Volumetric Density (g/cc) |
|---|---|---|---|---|
| Zone 130 | Microzone 1 | First Region 31 | 0.069 | 0.116 |
|  |  | Second Region 27 | 0.185 |  |
|  | Microzone 2 | First Region 33 | 0.041 | 0.49 |
|  |  | Second Region 26 | 0.531 |  |
| Zone 120 | Microzone 1 | First Region 19 | 0.133 | 0.251 |
|  |  | Second Region 24 | 0.384 |  |
|  | Microzone 2 | First Region 17 | 0.185 | 0.044 |
|  |  | Second Region 23 | 0.229 |  |

TABLE 7

Illustrative examples of differences in intensive properties within different zones:

|  | Thickness (Microns) | Thickness Differences | Basis Weights (gsm) | Basis Weights Differences | Volumetric Density (g/cc) | Volumetric Density Differences |
|---|---|---|---|---|---|---|
| Zone 130 First Region 32 | 2147 | 2118 | 149 | 135 | 0.069 | 0.423 |
| Zone 110 Second Region 8 | 29 |  | 14 |  | 0.492 |  |

The four representative microzones from two zones are shown in Tables 4-6 for illustration. But as can be understood, each pair of first and second regions in FIG. 43 could likewise be quantified to further populate additional rows in Table 4, but for purposes of conciseness are not. In general, for any fabric having two or more zones, each zone having a pattern of three-dimensional features defining microzones, the intensive properties can be measured and tabulated as illustrated herein with reference to FIGS. 43 and 44 to understand both the difference in values for intensive properties within a zone, and differences in values of intensive properties between one region in first zone to another region in a second zone.

A microzone spanning two zones, such as zones 110 and zone 130, can have an even greater difference in intensive properties relative to a microzone within a single zone. For example, viewing the data for a microzone spanning a first region of zone 130, for example at first region 32, and a second region of zone 110, for example at second region 8, the microzone exhibits dramatic differences in all of thickness, basis weight and volumetric density. The thickness of first region 32 of zone 130 is about 2100 microns, while the thickness of second region 8 of zone 110 is about 29 microns, or about a 72× differential. Likewise, the basis weight of first region 32 of zone 130 can be as high as 150 gsm, while the basis weight of second region 8 of zone 110 can be about 14 gsm, or about a 10× differential. Further, the volumetric density of first region 32 of zone 130 can be about 0.069 g/cc, while the volumetric density of second region 8 of zone 110 can be 0.492 g/cc, or about a 7× differential.

For each of the measured intensive property parameters of the various regions of a microzone, such a measurement is done using the micro CT method described herein. The resolution of the method supports establishing the intensive properties of microzone regions so differences and ratios comparisons of regions as described herein can be dimensioned.

Figure 47:
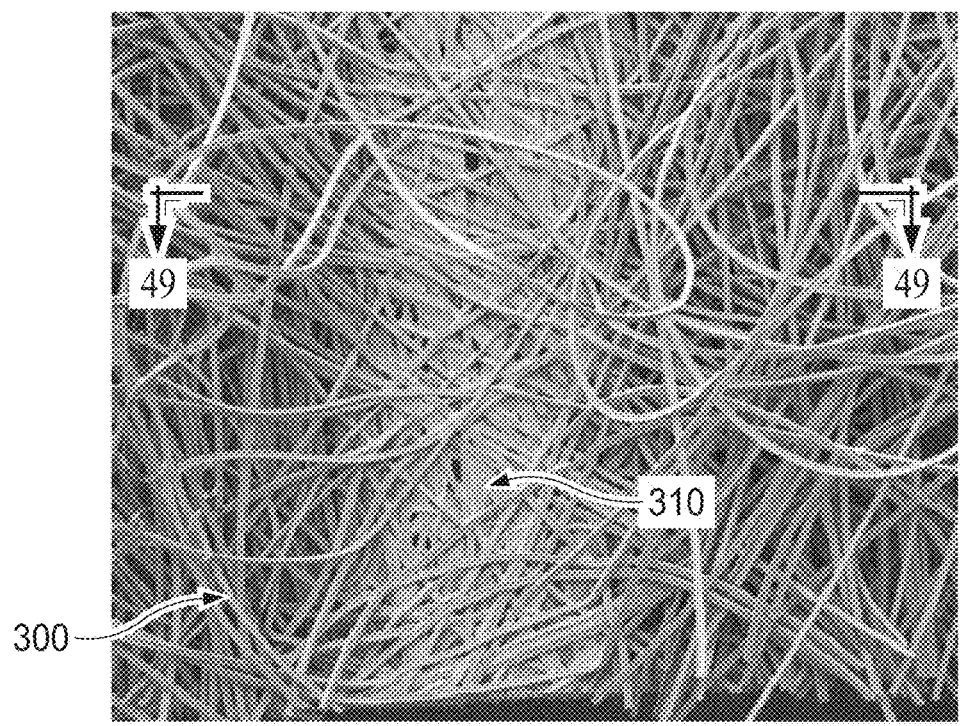
FIG. 47 is a photograph view image of a portion of an example of a shaped nonwoven of the present disclosure.

Further characterization of a fabric 10 can be made with reference to FIGS. 45-49, which are SEMs showing in greater detail certain aspects of the nonwoven fabric 10 and regions therein. FIGS. 45-49 are photographs of magnified portions of zone 110 of the fabric shown in FIG. 38. The nonwoven fabric 10 shown in FIG. 38 was made according to the process described above with reference to FIG. 7 in which the fabric was processed through a nip formed by compaction rolls 70 and 72, with roll 72 which contacts first side 12 being heated to cause partial bonding of fibers in the second regions 301. FIGS. 45 (facing the belt) and 46 (facing the heated compaction roll) are SEMs of a portion of the second surface 14 and first surface 12, respectively, magnified to 20X. FIGS. 47 (facing the belt) and 48 (facing the heated compaction roll) are photographs of a portion of the second surface 14 and first surface 12, respectively, magnified to 90X, and show in detail the beneficial structural characteristic of the partial bonding of fibers formed by compaction rolls 70 and 72.

Figure 48:
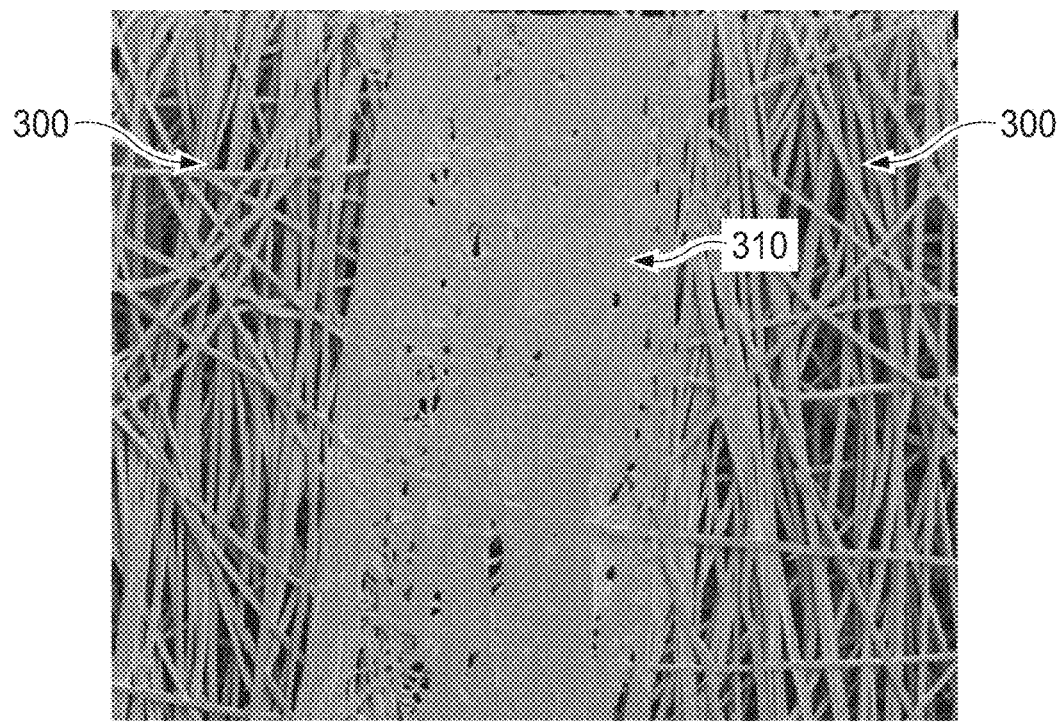
FIG. 48 is a photograph view image of a portion of an example of a shaped nonwoven of the present disclosure.
Figure 49:
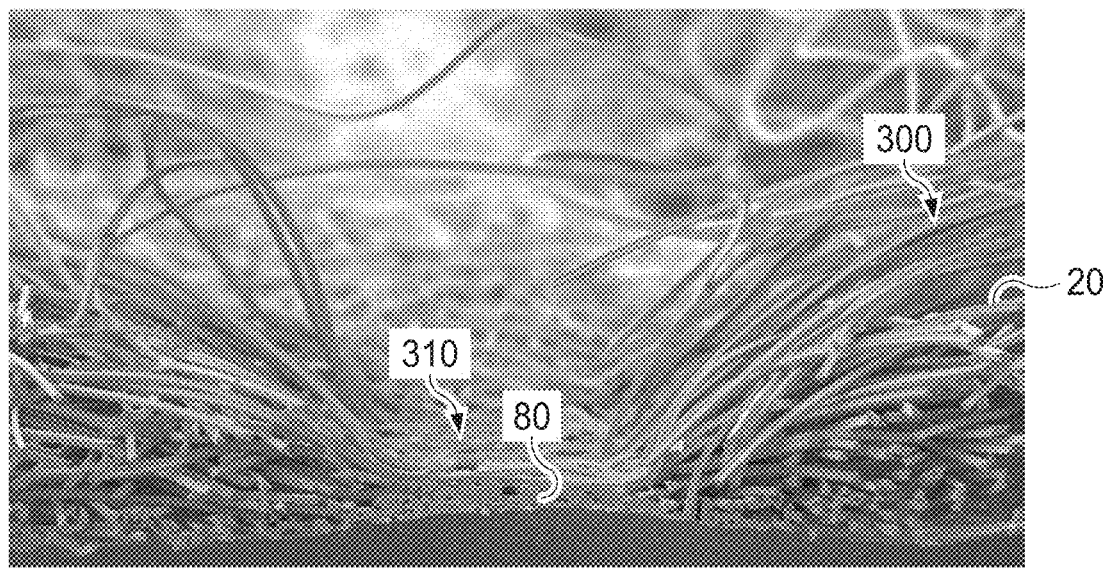
FIG. 49 is a photograph of a cross section of the example shown in FIGS. 47 and 48.
Figure 50:
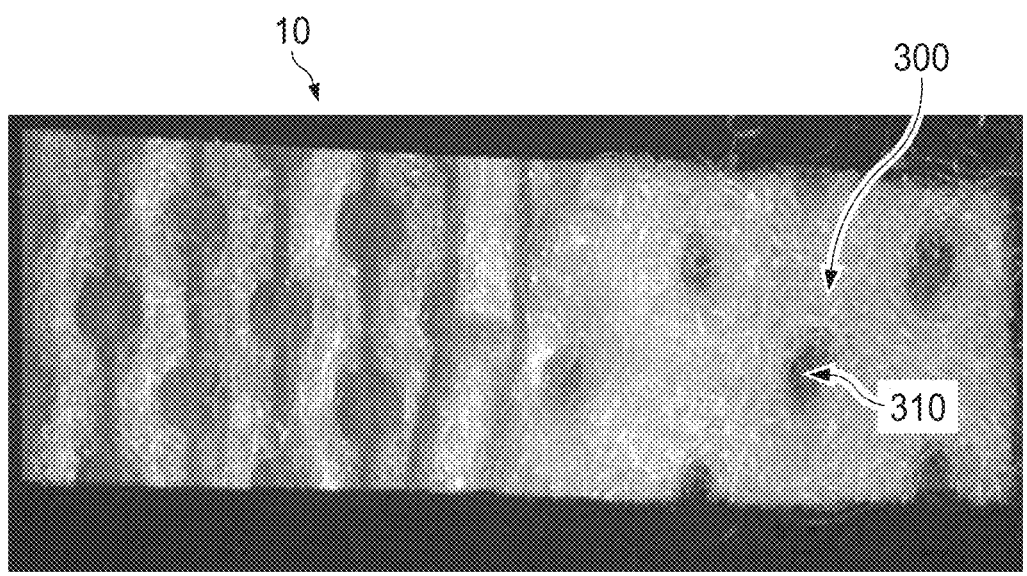
FIG. 50 is a photograph view image of a portion of an example of a shaped nonwoven of the present disclosure.

As can best be seen in FIGS. 47 and 48, as well as the cross sectional view of FIG. 49, the heated compaction rolls can cause thermal bonding of fibers to different degrees with a beneficial effect on the overall fabric 10. As shown, the fibers in contact with a heated roll, e.g., roll 70 in contact with first surface 12 of fabric 10, can be melt bonded such that the first surface 12 experiences relatively greater fiber-to-fiber bonding than does the second surface 14. In an embodiment, the bonded fibers 80 of the first surface can be substantially completely melt bonded to form, in effect, a film skin of bonded fibers, while the fibers in the second region 310 on the second side 14 can experience little to no bonding. This feature permits a nonwoven fabric 10 for use in a disposable absorbent article, e.g., as a topsheet, to maintain physical integrity during manufacture and use, as well as relative softness on one side, which can be the user-facing, skin-contacting side.

Even in the microzones with the greatest thickness differential, this "bond skinning" effect serves the purpose of maintaining web integrity, while not significantly impacting softness, or other beneficial properties such as fluid handling properties. As can be understood with reference to FIGS. 50-53, the differential in the extent of thermal bonding of fibers can be such that fibers on the first surface 12 at a second region 310 can be complete, or substantially complete, while the extent of thermal bonding of fibers on the second surface 14 at a first region 300 can be minimal, to no thermal bonding.

Figure 53:
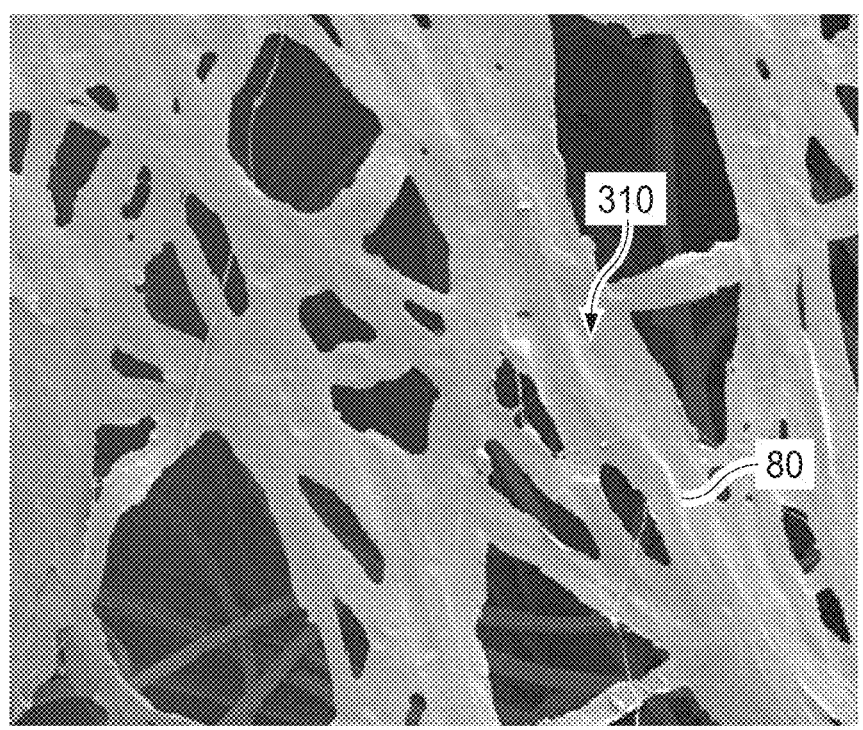
FIG. 53 is a photograph view image of a portion of an example of a shaped nonwoven of the present disclosure.

FIG. 50 shows again the portion of nonwoven fabric 10 shown in FIG. 38. FIGS. 51-53 show magnified images of one microzone, indicated in FIG. 50 as a first region 300 and second region 310, which visually appears to be a hole or an aperture. FIGS. 51 and 52 show the microzone as it appears on the second surface 14 magnified to 40× and 200×, respectively. FIG. 53 shows the second region 310 as it appears on the first side 12 under 200× magnification. Fibers in the second region 310 are completely, or substantially completely bonded, while fibers in the first region 300 are completely, or substantially completely unbonded. The benefit of the illustrated structure is that a microzone can function as a fluid pervious aperture, while the bonded regions of the second region 310 simultaneously functioning to maintain physical integrity of the fabric 10.

Microzones, therefore, play a significant role in the overall physical structure and functioning of a fabric 10 of the present invention. Producing relatively closely spaced, precisely designed three-dimensional features, enabled by the forming belt of the present disclosure, a fabric 10 can exhibit visually distinct zones, microzones, and three-dimensional features that provide for functional superiority in the areas of, at least, softness and fluid handling, as well as visually attractive aesthetic designs. The potential difference in physical properties of the first and second surfaces permits the nonwoven fabric 10 to be designed for both strength and softness, both form and function.

Figure 54:
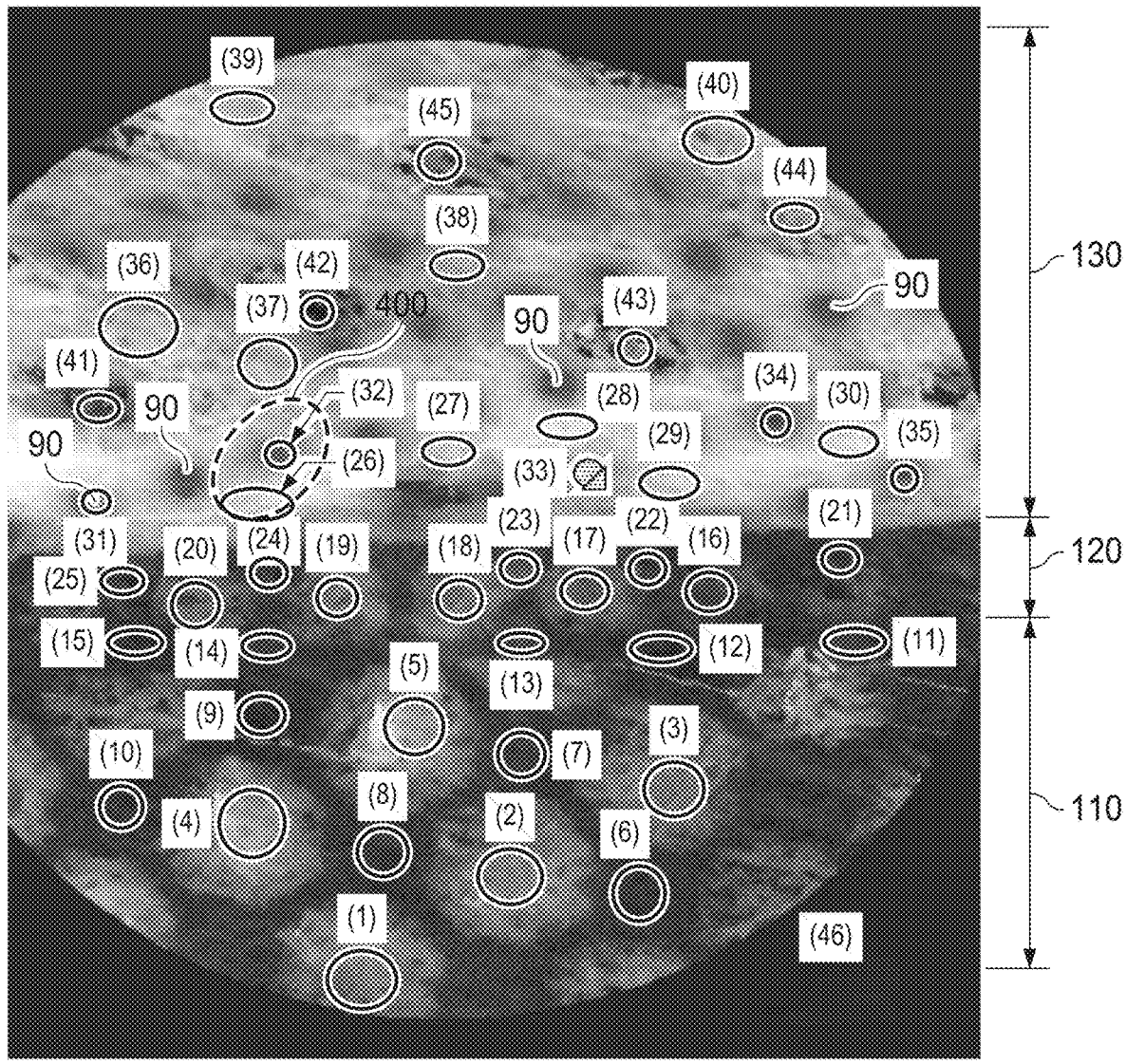
FIG. 54 is a Micro CT plan view image of the example shown in FIGS. 40 and 41 after experiencing additional processing.

FIG. 54 is a Micro-CT scan image of the portion of nonwoven fabric 10 similar to that shown in FIGS. 40 and 41, but having been subjected to the additional processing step of forming point bonds 90 in the nip of calendar rollers 71 and 73. As above, with respect to the discussion of FIGS. 43 and 44, for specific point bond microzones 400 first and second regions shown as numbered portions of the nonwoven fabric 10 can be analyzed, and include regions of point bonds, specifically in the numbered areas 31-35. For example, adjacent regions 32 and 26 form a microzone 400 in third zone 130. In FIG. 54, the specific regions were visually discerned to identify regions including the added point bond regions and analyzed to measure thickness, basis weight, and volumetric density, and the data is produced in FIG. 55, where the thickness, basis weight and volumetric density of all the regions, including the point bond regions are quantified and compared.

Figure 55:
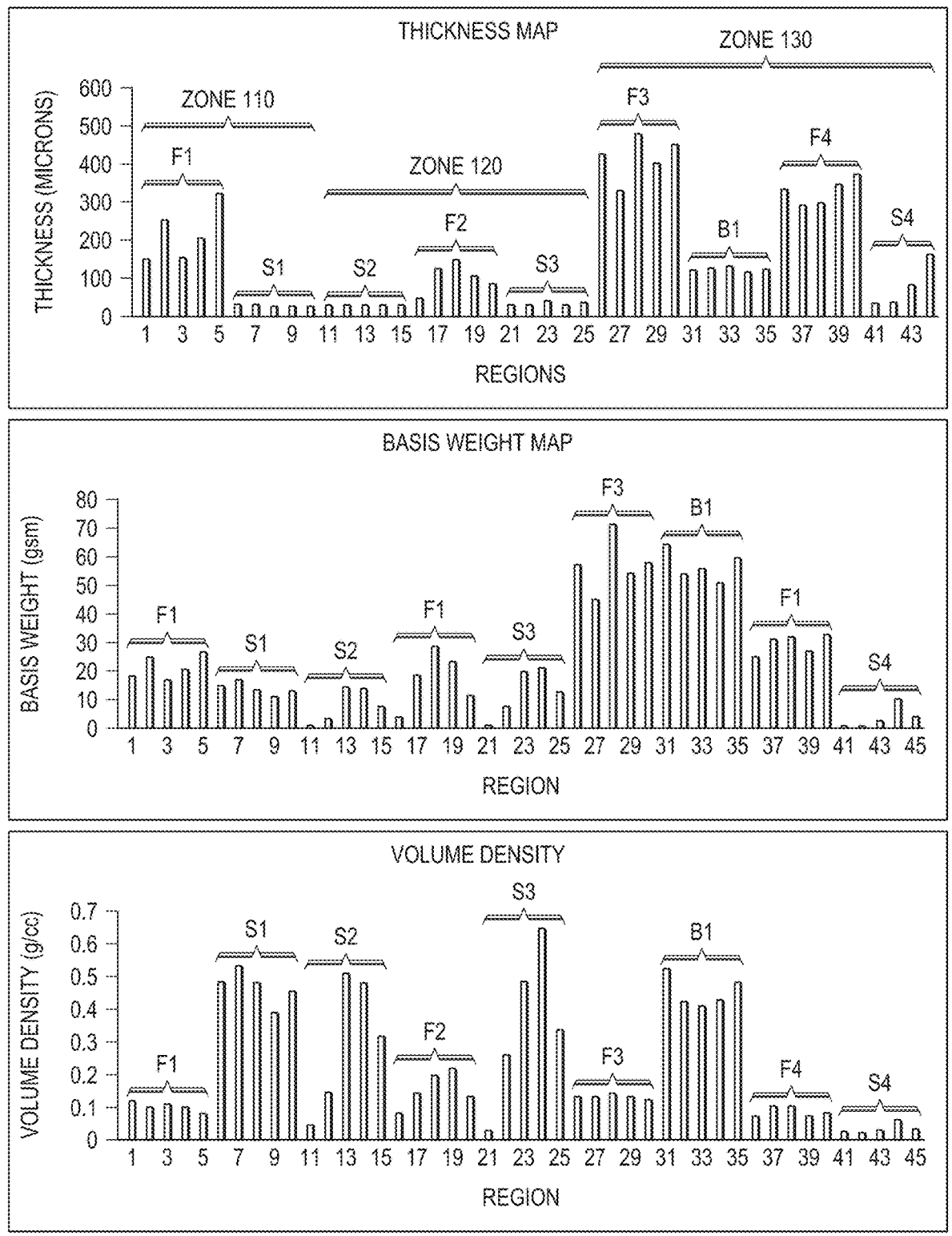
FIG. 55 is a graphical depiction of various benefits of the invention of the present disclosure shown in FIG. 54.

FIG. 55 shows data for groupings of first and second region measurements made within the three zones depicted in FIG. 54. The x-axis is the regions, with the numbers corresponding to the numbered regions on FIG. 43. First region measurements are labeled as Fn (e.g., F1) and second regions measurements are labeled as Sn (e.g., S1). Thus, regions 1-5 are first regions F1, each being in zone 110. Regions 6-10 are second regions S1, also being in zone 110. Likewise, first regions F2 are regions 16-20 in zone 120, and regions 11-15 and 21-25 are second regions S2 in zone 120. Finally, regions 31-35 are second regions but are point bonds 90 denoted on FIG. 55 as B1 to distinguish them in this disclosure as having been formed by a point bonding process. First regions F3 in zone 130 are regions 26-30 and 36-40, while regions 41-44 are second regions S2 in zone 130. The numbered regions are consistently depicted across all three graphs of FIG. 55, but for simplicity, the zones 110, 120, and 130 are depicted only on the Thickness Map.

The graphs shown in FIG. 54 represent graphically the magnitude of difference in intensive properties between first regions and second regions within any one of the zones of a fabric subjected to a calendaring point bonding step, and can be used to see graphically the difference in intensive properties for pairs of regions making up a microzone. For example, one can see that in zone 110 that basis weight between the two regions can vary within a range narrower than does thickness or volumetric density. For example, the thickness (caliper) can vary from about 325 microns in the first regions to about 29 microns in the second regions of zone 110, or about a 10× differential. The volumetric density in zone 110 can vary from about 0.08 g/cc to about 0.39 g/cc. Similar quantifiable distinctions can be understood for each of the zones shown.

In general, regions of a microzone can have broadly varying values for basis weight, thickness, and volumetric density.

Thus, with reference to FIG. 54 and FIG. 55 together, further characterization of the beneficial structure of a fabric 10 of the present disclosure can be understood specifically with respect to the thermal calendar point bonds 90. Focusing for purposes of description on zone 130, three-dimensional features defining a microzone comprising first and second regions which are point bonded regions can be identified and the values of intensive properties quantified. For example, in FIG. 54, a representative point bond microzone 400 in zone 130 can be the pair of regions marked as areas 26 and 32 or 30 and 35. That is, first region 26 and second region 32 form a point bond microzone 400, and first region 30 and second region 35 form a point bond microzone 400.

The differences in certain intensive properties for point bond microzones can be seen in FIG. 55. For example, taking the two point bond microzones 400 described above, e.g., the two point bond microzones 400 of regions 26 and 32 and 30 and 35, respectively, one can see there is a slight difference in basis weight between the first regions and second regions ranging from about 55 to about 60 gsm, but the same regions exhibit a significant difference in thickness of from about 430 microns to about 460 microns to about 125 microns, and a significant difference in volumetric density of from about 0.13-0.14 g/cc to about 0.41-0.48 g/cc. Other differences in intensive properties can be observed by reference to FIG. 55.

Bond points 90 may play a significant role in the overall physical structure and functioning of a fabric 10 of the present invention. By adding bond points 90 to the fabric 10 comprising relatively closely spaced, precisely designed three-dimensional features, enabled by the forming belt of the present disclosure, a fabric 10 can be further improved to exhibit a combination of visually distinct zones, microzones, and three-dimensional features that provide for functional superiority in the high performance combination of softness, strength, low fuzz, and fluid handling, as well as visually attractive aesthetic designs. The bond point feature provides for a nonwoven fabric 10 to be designed for the highest combined performance of strength, softness, fluid handling, and visual aesthetics, especially considering both form and function.

One benefit of the shaped nonwoven webs of the present disclosure is improved softness. Softness can be measured using the Emtec Tissue Softness Analyzer, available from Emtec Paper Testing Technology, Emtec Electronic, GmbH. Table 5 below shows softness values as TS7 measurements from the Emtec Tissue Softness Analyzer, according to the Emtec Test Method below. For all of the Examples 7-9 below, the nonwoven was made on a belt as described in FIG. 16, with the nonwoven web having an appearance similar to that shown in FIG. 2.

TABLE 5

TS7 Values for Shaped Nonwovens of the Disclosure

| Example No. | Side | TS7 Value (dB V2 rms) | Ratio FS/SS |
|---|---|---|---|
| Example 7 | First Surface | 10.30 | 1.35 |
| | Second Surface | 7.59 | |
| Example 8 | First Surface | 3.51 | 0.98 |
| | Second Surface | 3.59 | |
| Example 9 | First Surface | 9.61 | 1.48 |
| | Second Surface | 6.47 | |

Example 7

A bicomponent spunbond nonwoven fabric web was produced by spinning a 50:50 ratio of polyethylene sheath (Aspun-6850-A obtained from Dow chemical company) and polypropylene core (PH-835 obtained from LyondellBasell) in a trilobal fiber configuration, as discussed above with reference to Example 2. The nonwoven fabric was spun on a forming belt having a repeating pattern as described in FIG. 16 moving at a linear speed of about 25 meters per minute to form a fabric 10 having an average basis weight of 25 grams per square meter with a repeating pattern of diamond shapes as shown in FIG. 2. Fibers of the fabric were compacted by compaction rolls 70, 72, but rather than be calendared, further bonding was achieved by a through-air bonding unit as described below with respect to FIG. 56, at a temperature of 145 degrees C.

Example 8

Figure 56:
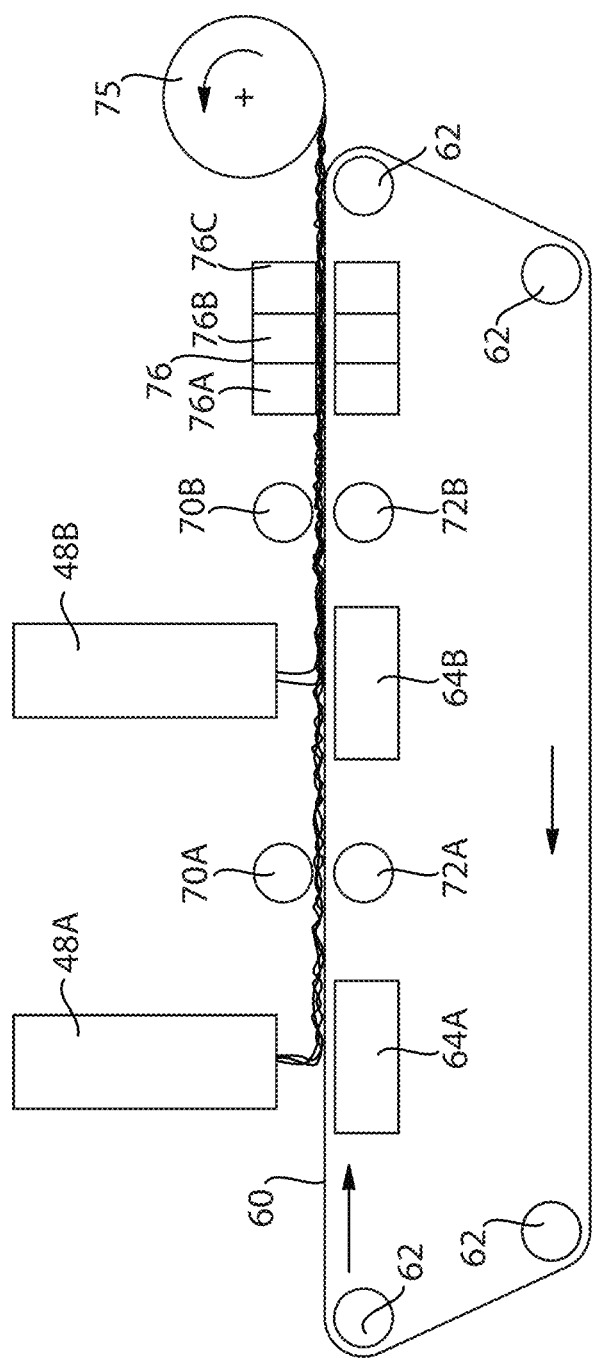
FIG. 56 is a schematic representation of an apparatus for making a fabric of the present disclosure.

A bicomponent spunbond nonwoven fabric that was produced by spinning a 30:70 ratio of polyethylene sheath (Aspun-6850-A obtained from Dow chemical company) and polypropylene core (HG475 FP obtained from Borealis) in a round fiber configuration, using a dual beam spunbond process, as described in FIG. 56. The nonwoven fabric was spun on a forming belt having a repeating pattern as described in FIG. 16 as described above with respect to FIG. 7 moving at a linear speed of about 152 meters per minute to an average basis weight of 35 grams per square meter to form a repeating pattern of diamond shapes as shown in FIG. 2. The difference between shaped nonwoven webs made according to the process of FIG. 7, and the Example 8, is that Example 8 was made on a hybrid of the process described in FIG. 7, and that described in FIG. 56 below. Specifically, the process involved two spin beams as shown in FIG. 56, but the final heating step was by calendar rolls 71, 73, rather than through-air bonding. Fibers of the fabric were bonded on first surface 12 by heated compaction rolls 70A and 72A at 110° C. after the first beam 48A and compaction rolls 70B and 72B at 110° C. after the second beam 48B, and calendar bonded at about 140 C at calendar rolls 71 and 73 before being wound on to a reel at winder 75.

Example 9

A bicomponent spunbond nonwoven fabric that was produced by spinning a 30:70 ratio of polyethylene sheath (Aspun-6850-A obtained from Dow chemical company) and polypropylene core (HG475 FP obtained from Borealis) in a round fiber configuration, using a dual beam spunbond process, as described in FIG. 56. The nonwoven fabric was spun on a forming belt having a repeating pattern as described in FIG. 16 moving at a linear speed of about 228 meters per minute to an average basis weight of 25 grams per square meter to form a repeating pattern of diamond shapes as shown in FIG. 2. Fibers of the fabric were further bonded on first surface 12 by heated compaction rolls 70A and 72A at 110° C. after the first beam 48A and compaction rolls 70B and 72B at 110° C. after the second beam 48B, and hot air through bonded at three heating zones of through-air bonder 76 (as shown on FIG. 56) of 100 C, 135 C and 135 C before being wound on to a reel at winder 75.

Examples 7-9 are representative of shaped nonwoven fabrics of the present disclosure that exhibit an improved softness, as indicated by the Emtec measurements. The Emtec measured values can be from about 1 dB $V^2$ rms to about 15 dB $V^2$ rms, or from about 3 dB $V^2$ rms to about 10 dB $V^2$ rms, or from about 5 dB $V^2$ rms to about 8 dB $V^2$ rms. In general, the Emtec measured values for either the first surface or the second surface can be any integer value up to about 15 dB $V^2$ rms, and any range of integers between 1 and 15. Further, in general, the ratio of the measured Emtec value for the first side to the second side can be between 1 and 3 and any real number between 1 and 3.

Without being bound by theory, it is believed that the improvement in softness exhibited by the shaped nonwoven fabrics of the present invention is achieved the method and apparatus of the invention which permits for differential intensive properties in relatively small zones, including the disclosed zones and microzones. The ability to design and make shaped nonwoven fabrics with the disclosed differences in basis weight, density, or thickness, for example, while simultaneously delivering a consolidated fabric useful for topsheets in absorbent articles, for example, breaks a previously held technical contradictions between surface texture and softness. That is, the shaped nonwoven fabrics of the present disclosure may deliver visibly noticeable surface texture, including in irregular patterns, as well as superior softness, as indicated by measured Emtec values. Additionally, the shaped nonwoven fabrics of the present disclosure may deliver visibly noticeable surface texture in combination physical integrity and reduced fuzzing properties, as well as superior softness, as indicated by measured Emtec values.

As discussed above, in an example, a process for making a shaped nonwoven fabric can be a modified version of the process described with respect to FIG. 7. One modification is described with respect to FIG. 56. As shown in FIG. 56, the process can include a belt 60 as described above in a melt-spinning process in which more than one spin beam is employed. As illustrated schematically showing only spin packs 48A and 48B, two beams can be used to melt spin fibers onto belt 60, with a compaction operation 70A, 72A and 70B, 72B occurring after each beam respectively. Vacuum boxes 64A and 64B can also be operatively associated with each spin beam 48A and 48B, respectively.

After spinning fibers onto belt 60, and after being compacted, including optionally thermally bonding during compaction as described above, the shaped nonwoven web can be subject to additional heating by through-air heater 76, which can have multiple chambers, such as three chambers 76A. 76B and 76C, each independently temperature controlled.

Examples 7 and 9 above were fabricated on a twin beam process line and through-air bonded in a process schematically shown in FIG. 56. Without being bound by theory, it appears that through-air bonding preserves much of the three-dimensionality of the three-dimensional features of the shaped nonwoven fabric, as indicated by the difference in TS7 values in Table 5. Alternatively, if a less sided shaped nonwoven fabric is desired, it appears that calendar bonding tends to even out the TS7 values, as shown by Example 8 in Table 5. Thus, the process parameters can be controlled as described herein to achieve predetermined softness per side, i.e., surface, of a shaped nonwoven fabric.

In addition to the benefits detailed above, another benefit of the shaped nonwoven webs of the present disclosure is the ability to provide a nonwoven web with microzones that have a hydrophobic region and a separate hydrophilic region. The hydrophilicity and/or hydrophobicity in a particular region of the microzone can be determined by a Time to Wick measurement using the Time to Wick Test Method as described herein and/or a Contact Angle measurement using the Contact Angle Test Method as described herein. As used herein, the term "hydrophilic", in reference to a particular region of the microzone, means that when tested using the Time to Wick Test Method, the Time to Wick for that particular region is less than 10 seconds. As used herein, the term "hydrophobic", in reference to a particular region of the microzone, means that when tested using the Contact Angle Test Method, the Contact Angle for that particular region is 90° or greater.

Table 6 below details Contact Angle and Time to Wick measurements for shaped nonwovens as detailed herein. For both Examples 10 and 11 below, the nonwoven was made on a belt as described in FIG. 16, with the nonwoven web having an appearance similar to that shown in FIG. 2.

TABLE 6

Contact Angle and Time to Wick Values for Shaped Nonwovens of the Disclosure

| Example No. | Region | Contact Angle (Θc) | Time to Wick (seconds) |
|---|---|---|---|
| Example 10 | First Region | 135 | 60 |
| | Second Region | 0 | 0.307 |
| Example 11 | First Region | 126 | 60 |
| | Second Region | 0 | 2.360 |

Example 10

A bicomponent spunbond nonwoven fabric web was produced by spinning a 50:50 ratio of polyethylene sheath (Aspun-6850-A obtained from Dow chemical company) and polypropylene core (PH-835 obtained from LyondellBasell) in a trilobal fiber configuration, as discussed above with reference to Example 2. The nonwoven fabric was spun on a forming belt having a repeating pattern as described in FIG. 16 moving at a linear speed of about 25 meters per minute to form a fabric 10 having an average basis weight of 25 grams per square meter with a repeating pattern of diamond shapes as shown in FIG. 2. Fibers of the fabric were compacted by compaction rolls 70, 72, but rather than be calendared, further bonding was achieved by a through-air bonding unit as described below with respect to FIG. 56, at a temperature of 145° C.

A surfactant, Stantex S 6327 (a combination of castor oil ethoxylates with PEG diesters), supplied by Pulcra Chemicals, was then disposed on the back side surface of the nonwoven fabric (i.e., the flat side surface opposite the side with the relatively pillowy three-dimensional features disposed thereon) through a kiss coating process. The coating process was performed using a Reicofil Kiss Roll and Omega drying process, both of which are commonly known in the art. The surfactant used in the kiss roll process was at a 6% surfactant concentration in water at a temperature of 40° C. The kiss roll contact angle was set at 2500 and the drying temperature was 80° C. The nonwoven fabric was then brought into contact with the kiss roll operating at a speed of 13 rpm, delivering 0.45 wt % surfactant to the nonwoven fabric (% surfactant is weight of added surfactant per 1 m$^2$ divided by weight of 1 m$^2$ nonwoven fabric).

Example 11

A bicomponent spunbond nonwoven fabric web was produced by spinning a 50:50 ratio of polyethylene sheath (Aspun-6850-A obtained from Dow chemical company) and polypropylene core (PH-835 obtained from LyondellBasell) in a trilobal fiber configuration, as discussed above with reference to Example 2. The nonwoven fabric was spun on a forming belt having a repeating pattern as described in FIG. 16 moving at a linear speed of about 25 meters per minute to form a fabric 10 having an average basis weight of 25 grams per square meter with a repeating pattern of diamond shapes as shown in FIG. 2. Fibers of the fabric were compacted by compaction rolls 70, 72, but rather than be calendared, further bonding was achieved by a through-air bonding unit as described below with respect to FIG. 56, at a temperature of 145° C.

A surfactant, Stantex S 6327 (a combination of castor oil ethoxylates with PEG diesters), supplied by Pulcra Chemicals, was then disposed on the front side surface of the nonwoven fabric (i.e., the side with the relatively pillowy three-dimensional features disposed thereon) through an inkjet printing process. The inkjet printing process was performed using a Dimatix DMP 2831 inkjet printer, fitted with a cartridge model #DMC-11610/PM 700-10702-01 (10 pL). The print head temperature was 40° C. The surfactant used in the inkjet printing process consisted of 75% w/w Stantex S 6327 and 25% w/w Ethanol. Surfactant was printed in the second regions of the microzones of the nonwoven fabric by orienting the nonwoven fabric sample such that the second regions of a first row of microzones were aligned with the print head direction and printing a first series of straight lines, with droplet spacing adjusted to 170 um. The nonwoven fabric sample was then turned by an angle such that the second regions of a second row of microzones were aligned with the print head and a second series of straight lines were printed at 170 um. The basis weight of the fibers of the second region is about 16.0 gsm. The basis weight of the surfactant that was inkjet printed onto the second region is about 0.25 gsm. Accordingly, the amount of surfactant printed locally on the second region was determined to be about 1.6 wt % surfactant (0.25 gsm/16.0 gsm). Overall, the amount of surfactant printed on the nonwoven fabric sample was determined by the ratio between printed line width and line spacing to be at about 0.2 wt % surfactant.

In addition to Stantex S 6327, the use of other surfactants to render first and/or second regions of particular microzones hydrophilic and/or hydrophobic (though any application method) is considered within the scope of this disclosure. Other potential surfactants to be used in the processes and nonwoven fabrics detailed here include non-ionic surfactants including esters, amides, carboxylic acids, alcohols, ethers-polyoxyethylene, polyoxypropylene, sorbitan, ethoxylated fatty alcohols, alyl phenol polyethoxylates, lecithin, glycerol esters and their ethoxylates, and sugar based surfactants (polysorbates, polyglycosides), and anionic surfactants including sulfonates, sulfates, phosphates, alkali metal salts of fatty acids, fatty alcohol monoesters of sulfuric acid, linear alkyl benzene sulfonates, alkyl diphenyloxide sulfonates, lignin sulfonates, olefin sulfonates, sulfosuccinates, and sulfated ethoxylates of fatty alcohols, and cationic surfactants including amines (primary, secondary, tertiary), quaternary ammoniums, pyridinium, quaternary ammonium salts—QUATS, alkylated pyridinium salts, alkyl primary, secondary, tertiary amines, and alkanolamides, and zwiterionic surfactants including amino acids and derivatives, amine oxide, betaines, and alkyl amine oxides, and polymeric surfactants including polyamines, carboxylic acid polymers and copolymers, EO/PO block copolymers, ethylene oxide polymers and copolymers, and polyvinylpyrrolidone, and silicone surfactants including dimethyl siloxane polymers with hydrophile, and perfluorocarboxylic acid salts and fluorosurfactants.

The shaped nonwoven fabrics detailed above have microzones with regions having differences in intensive properties, such as basis weight, density, or thickness, for example. Those same shaped nonwoven fabrics can also simultaneously have such regions of the microzones that are particularly and separately hydrophobic and/or hydrophilic. Any of the shaped nonwoven fabric examples detailed herein (e.g., samples that include zones and/or microzones with regions having differences in thickness, basis weight and/or volumetric density, and/or surfaces with the various TS7 values disclosed herein) can further have regions of a microzone with differences in hydrophilicity as detailed herein. Hydrophilicity can be provided through targeted application(s) of surfactant(s) onto particular regions of the microzones of the shaped nonwoven fabric. For example, the second region of a microzone may have surfactant disposed thereon, while the first region of the same microzone may have no surfactant disposed thereon. Moreover, the first region of a microzone may have surfactant disposed thereon, while the second region of the same microzone may have no surfactant disposed thereon. For instance, in one microzone, the first or second region may have from about 0.01% to about 5.0%, about 0.05% to about 4.0%, about 1.0% to about 3.0%, and any concentric range within the range of about 0.01% to about 5.0% surfactant, and the other region has no surfactant (i.e., surfactant free). As an example, in one microzone, the second region may have from about 0.01% to about 5.0%, about 0.05% to about 4.0%, about 1.0% to about 3.0%, and any concentric range within the range of about 0.01% to about 5.0% surfactant, and the first region has no surfactant (i.e., surfactant free). Accordingly, some shaped nonwoven fabrics disclosed herein have a microzone with at least one of the first and second regions having a surfactant, and the ratio of % surfactant in the first region to % surfactant in the second region is less than 1. Further, some shaped nonwoven fabrics disclosed herein have a microzone with at least the second region of the microzone having a surfactant, and the ratio of % surfactant in the first region to % surfactant in the second region is less than 1.

As another example, the second region of a microzone may have a particular amount of surfactant or % surfactant disposed thereon, while the first region of the same microzone may have a different amount of surfactant or % surfactant disposed thereon. For instance, in one microzone, the first region may have from about 0.01% to about 2.0%, about 0.05% to about 1.5%, about 0.1% to about 1.0%, and any concentric range within the range of about 0.01% to about 2.0% surfactant, and the second region may have a differing amount. Moreover, in one microzone, the second region may have from about 0.01% to about 5.0%, about 0.05% to about 4.0%, about 1.0% to about 3.0%, and any concentric range within the range of about 0.01% to about 5.0% surfactant, and the first region may have a differing amount. The % surfactant for a particular region of a microzone may be determined by taking the grams per square meter of surfactant disposed in the particular region and dividing it by the basis weight of the fibers of the shaped nonwoven fabric contained within the same region. The grams per square meter of surfactant disposed in a particular region may be determined using any currently known method in the art (e.g., gravimetric, etc.). The basis weight of the fibers of the shaped nonwoven fabric contained within a particular region of a microzone may also be determined using any currently known method in the art (e.g., gravimetric, micro-CT, etc.). For particular microzone examples, the basis weight ranges/examples of fibers contained in the first and second regions are detailed above.

A surfactant may be disposed on the shaped nonwoven fabrics by any method known in the art. Particular examples include kiss coating, inkjet printing, gravure printing, off-set gravure printing, flexo-graphic printing of the surfactant and registered printing of the surfactant. Any such method can dispose surfactant onto either the first and/or second surface of the shaped nonwoven fabrics. For the overall shaped nonwoven fabric (taking into account all of the individual zones and microzones on the fabric), the surfactant may be added to the shaped nonwoven fabric in an amount from about 0.01% to about 2.0%, about 0.05% to about 1.5%, about 0.1% to about 1.0%, and any concentric range within the range of about 0.01% to about 2.0%. To calculate % surfactant added to the overall shaped nonwoven fabric, divide the grams per square meter of surfactant in the overall shaped nonwoven fabric by the basis weight of the overall shaped nonwoven fabric. The grams per square meter of surfactant disposed in the overall shaped nonwoven fabric may be determined using any currently known method in the art (e.g., gravimetric, etc.). The basis weight of the overall shaped nonwoven fabric may also be determined using any currently known method in the art (e.g., gravimetric, micro-CT, etc.).

Referring again to FIGS. 38 and 39 which show a portion of one pattern of a nonwoven fabric 10, a first zone 110 (on the left side of FIG. 38) is characterized by generally MD-oriented rows of variable width first regions 300 separated by MD-oriented rows of variable width second regions 310 (first and second region being within a microzone). The first region is also the three-dimensional feature 20 that defines the first and second regions 300, 310. In an embodiment, a three-dimensional feature is a portion of the nonwoven fabric 10 that was formed between or around a raised element of the forming belt, which in this description is the first region 30, such that the resulting structure has a relatively greater dimension in the Z-direction, a relatively higher basis weight, and a lower volumetric density, when compared to the second region 310. Moreover, the first region 300 may be hydrophobic and the second region 310 may be hydrophilic. Targeted addition of a surfactant to the second region 310 of the microzone may cause the second region to be hydrophilic. Accordingly, the first region 300 of the microzone may have a Contact Angle of greater than about 90°, or between about 90° and about 140°, or between about 110° and about 135°, or between about 125° and about 135°, or any concentric range contained within between about 90° and about 140°, when tested by the Contact Angle Test Method detailed herein. The second region 310 of the microzone may have a Contact Angle of less than 90° when tested by the contact Angle Test Method detailed herein. The first region 300 of the microzone may have a Time to Wick value of greater than about 10 seconds, or between about 10 seconds and 60 seconds, as measured by the Time to Wick Test Method detailed herein. The second region 310 of the microzone may have a Time to Wick value of less than about 10 seconds, less than about 5 seconds, or less than about 2.5 seconds, or less than about 1 second, or less than about 0.5 seconds, as measured by the Time to Wick Test Method detailed herein. Shaped nonwoven fabrics contemplated herein include any of the above detailed parameter ranges for Contact Angle and/or Time to Wick measurements for the first region and/or the second region in combination with any of the other herein disclosed intensive properties/property differences for the same or different regions in the same or different microzone on the shaped nonwoven fabric.

Shaped nonwoven fabrics having the above detailed microzones with regions having differences in basis weight, density, or thickness, for example, while also simultaneously having such regions of a particular microzone being separately hydrophobic and/or hydrophilic can provide many useful applications such as topsheet materials for baby care, fem care and adult incontinence products, as well as use in medical pads, wipes and cleaning pads, etc.

Texture is a key component of human visual perception. A textured, patterned nonwoven may be more aesthetically pleasing to a consumer if the textured pattern exhibits a visual sharpness and uniformity. Such uniform, visually sharp textured patterns may be viewed as indicative of nonwoven's quality. A uniform, visually sharp textured pattern on a nonwoven imparts clean, well defined lines or boundaries of textural contrast to the visual perception of the nonwoven. Collectively, a uniform, visually sharp textured pattern on a nonwoven may be describe as exhibiting high visual resolution.

Accordingly, in addition to the benefits detailed above, another benefit of the shaped nonwoven webs of the present disclosure is the ability to provide a textured nonwoven web with a at least a first discernible zone that exhibits visual sharpness and uniformity. As used herein, the term "visual sharpness" is defined as the characteristic of being able to visually separate something into its constituent parts. In other words, visual sharpness is the ability to visually distinguish two objects as separate structures rather than a single fuzzy object. In another embodiment, visual sharpness entails observing clean, well defined lines or boundaries of textural contrast between zones or regions rather than faded, fuzzy, or difficult to visually identify lines of textural contrast.

The visually sharp patterns of the textured nonwovens detailed herein can be quantified in various ways. One way to measure the visual sharpness of the textured nonwoven patterns detailed herein is through a Haralick Features Extraction and Analysis ("Haralick Texture Analysis"). Haralick Texture Analysis is the general process of analyzing an image to obtain a higher-level of information (e.g., color, shape, texture). The particular Haralick Texture Analysis employed herein utilizes one or more images to measure spatial distributions of gray values. Those distributions are then used to calculate contrast values within a textured nonwoven. Such contrast values are indicative of the visual sharpness of the patterned nonwoven.

As detailed further below in the Test Methods section, the first step in a Haralick Texture Analysis is computing the Gray-Level Co-occurrence Matrix (GLCM). The GLCM is a tabulation of how often different combinations of pixel gray levels could occur in an image. In other words, GLCM shows how often each gray level occurs at a pixel located at a fixed geometric position relative to each other pixel, as a function of the gray level. In a second step, texture features are calculated from the GLCM. Textural features can be scalar numbers, discrete histograms or empirical distributions, and reflect the regular changes of gray values in images. The goal is to assign an unknown sample image to one of a set of known texture classes. Specific parameters obtained through Haralick Texture Analysis of the shaped nonwoven webs of the present disclosure include Haralick Max Mean Contrast Value, Haralick Maximum 90° Contrast Value, Haralick Maximum 0° Contrast Value. and the existence or not of a Periodic Haralick Wave Response. An additional measure of visual sharpness is the Gray Level Contrast Slope. Further details of such parameters and their measurement methods are further detailed herein.

In addition to being visually sharp, the patterns of the textured nonwovens detailed herein can be uniform in appearance. One way to measure the uniformity of the textured nonwoven patterns detailed herein is through Gray Level Variation. Gray Level Variation may be calculated within a single article, or amongst multiple articles, as further detailed herein.

Tables 7A-D below detail Haralick Analysis data for shaped nonwovens as detailed herein, as well as comparison data for flat, standard, non-patterned nonwoven fabrics.

Example 12

Figure 57:
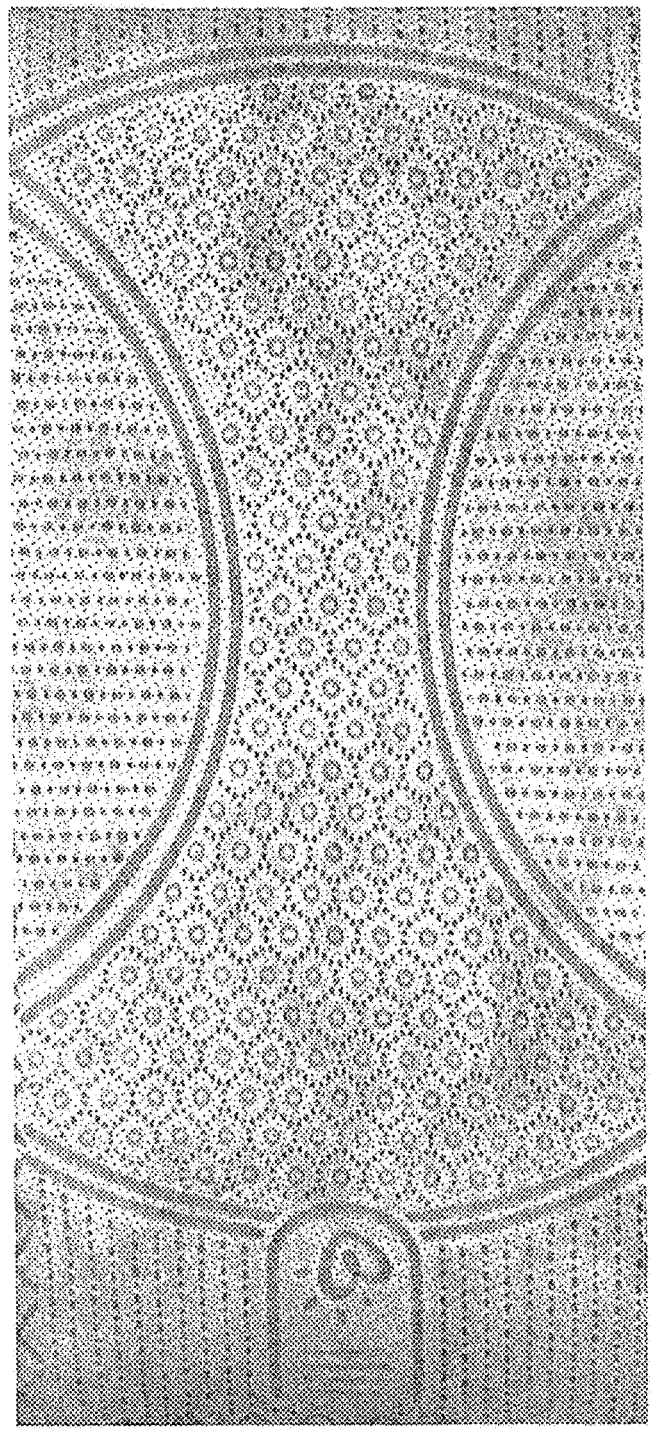
FIG. 57 is a photograph of an example of a shaped nonwoven fabric of the present disclosure.

A side by side bicomponent spunbond nonwoven fabric web was produced by spinning a 30:70 ratio of polypropylene (PP3155 obtained from ExxonMobil company) and 75/25 mixture of polypropylenes (PP3854 and PP3155 obtained from ExxonMobil company) in a round fiber configuration. The nonwoven fabric was spun on a forming belt having a repeating pattern (the same type of cured resin forming belt as shown in FIGS. 12, 16 18 and 19, and described herein—but with different visually discernable zones having patterns of three dimensional features), moving at a linear speed of about 20 meters per minute to form a fabric having an average basis weight of 35 grams per square meter. As depicted in FIG. 7, fibers of the fabric were compacted by compaction rolls 70, 72 heated to 140 degrees C. Fibers of the fabric were further calendar bonded at calendar rolls 71, 73, with roll 73 being an engraved roll having raised portions 88 in the form of pins. Roll 73 was heated to 140 degrees C. to form point bonds 90 on the second side of the fabric (similar to the description of Example 6 detailed herein). An image of the nonwoven fabric of Example 12 is shown in FIG. 57.

Example 13

A side by side bicomponent spunbond nonwoven fabric web was produced by spinning a 30:70 ratio of polypropylene (PP3155 obtained from ExxonMobil company) and 75/25 mixture of polypropylenes (PP3854 and PP3155 obtained from ExxonMobil company) in a round fiber configuration. The nonwoven fabric was spun on a flat, standard permeable laydown belt (i.e., the belt did not include cured resin to the give the belt structure), moving at a linear speed of about 20 meters per minute to form a fabric having an average basis weight of 34 grams per square meter. As depicted in FIG. 7, fibers of the fabric were compacted by compaction rolls 70, 72 heated to 90 degrees C. Fibers of the fabric were further calendar bonded at calendar rolls 71, 73, with roll 73 being an engraved roll having raised portions 88 in the form of pins. Roll 73 was heated to 140 degrees C. to form point bonds 90 on the second side of the fabric (similar to the description of Example 6 detailed herein). The nonwoven fabric of Example 13 is flat, with no visually discernable zones having a pattern of three dimensional features.

Example 12 is representative of the shaped nonwoven fabrics of the present disclosure that exhibit an improved visual sharpness. For this example, and any other shaped nonwovens described herein, the shaped nonwovens do not contain apertures. In other words, the nonwovens described herein do not comprise any sections of zero basis weight. Moreover, in the shaped nonwovens described herein, when a region is defined as having an intensive property, it must have a value above zero for that property (basis weight, caliper, volume, etc.). Example 13 is a standard, flat nonwoven fabric, without any visually discernible zones having a pattern of three dimensional features. Example 13 does not exhibit a pattern with high visual sharpness and is utilized for comparison to the visually sharp patterns displayed by the new shaped nonwovens detailed herein—evidenced by Example 12 detailed herein.

Figure 58:
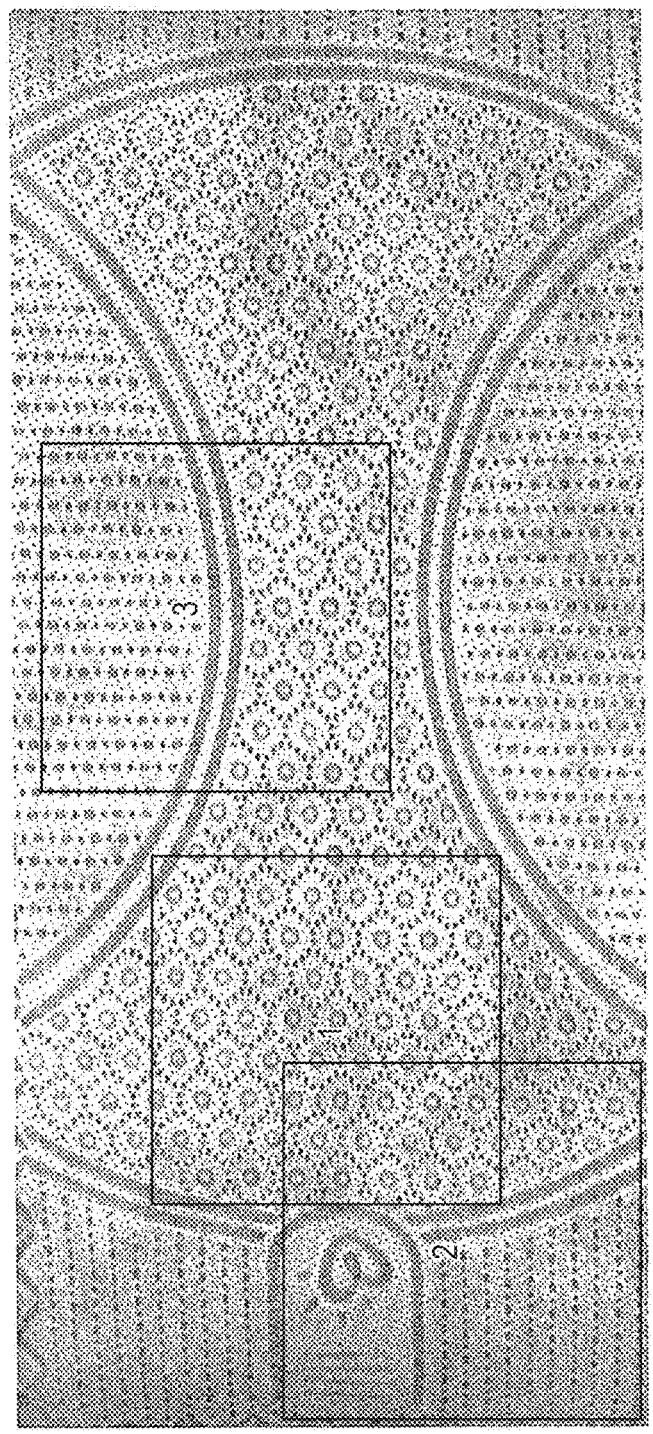
FIG. 58 is a photograph of an example of a shaped nonwoven fabric of the present disclosure with three identified locations utilized in the Intra-Article Gray Level Variation Test Method.

Tables 7A-D: Data for the Shaped Nonwovens of the Disclosure that Exhibit an Improved Visual Sharpness and/or Uniformity and Comparative Examples Example 12 was measured for Gray Level Variation values using the Intra-Article Gray Level Variation Test Method detailed below in three different 4 inch by 4 inch scans of visually discernible zones on the shaped nonwoven fabric. The location of those three scans are shown in FIG. 58 and identified as Locations 1, 2 and 3. Example 13 was also measured for Gray Level Variation values using the Intra-Article Gray Level Variation Test Method in a single 4 inch by 4 inch scan. These measurements on Example 13 were performed two times at different locations on the flat, non-patterned nonwoven.

TABLE 7A

Gray Level Variation measured by Intra-Article Gray Level Variation Test Method

| Sample No./Location | Gray Level Variation |
| --- | --- |
| Example 12, Location 1 | 3.8 |
| Example 12, Location 2 | 2.8 |
| Example 12, Location 3 | 3.5 |
| Example 13, First Location | 4.2 |
| Example 13, Second Location | 4.7 |

Example 12 was measured for Haralick Maximum 90° Contrast value, Haralick Maximum 0° Contrast value. Haralick Maximum 45° Contrast value, Haralick Maximum 135° Contrast value, and Haralick Max Mean Contrast value using the Haralick Maximum Contrast Test Method detailed below in three different 4 inch by 4 inch scans of visually discernible zones on the shaped nonwoven fabric. The location of those three scans are shown in FIG. 58 and identified as Locations 1, 2 and 3. Example 13 was also measured for Haralick Maximum 90° Contrast value. Haralick Maximum 90° Contrast value, Haralick Maximum 45° Contrast value. Haralick Maximum 135° Contrast value, and Haralick Max Mean Contrast value using the Haralick Maximum Contrast Test Method in two 4 inch by 4 inch scans. These measurements on Example 13 were performed two times at different locations on the flat, non-patterned nonwoven.

Figure 59:
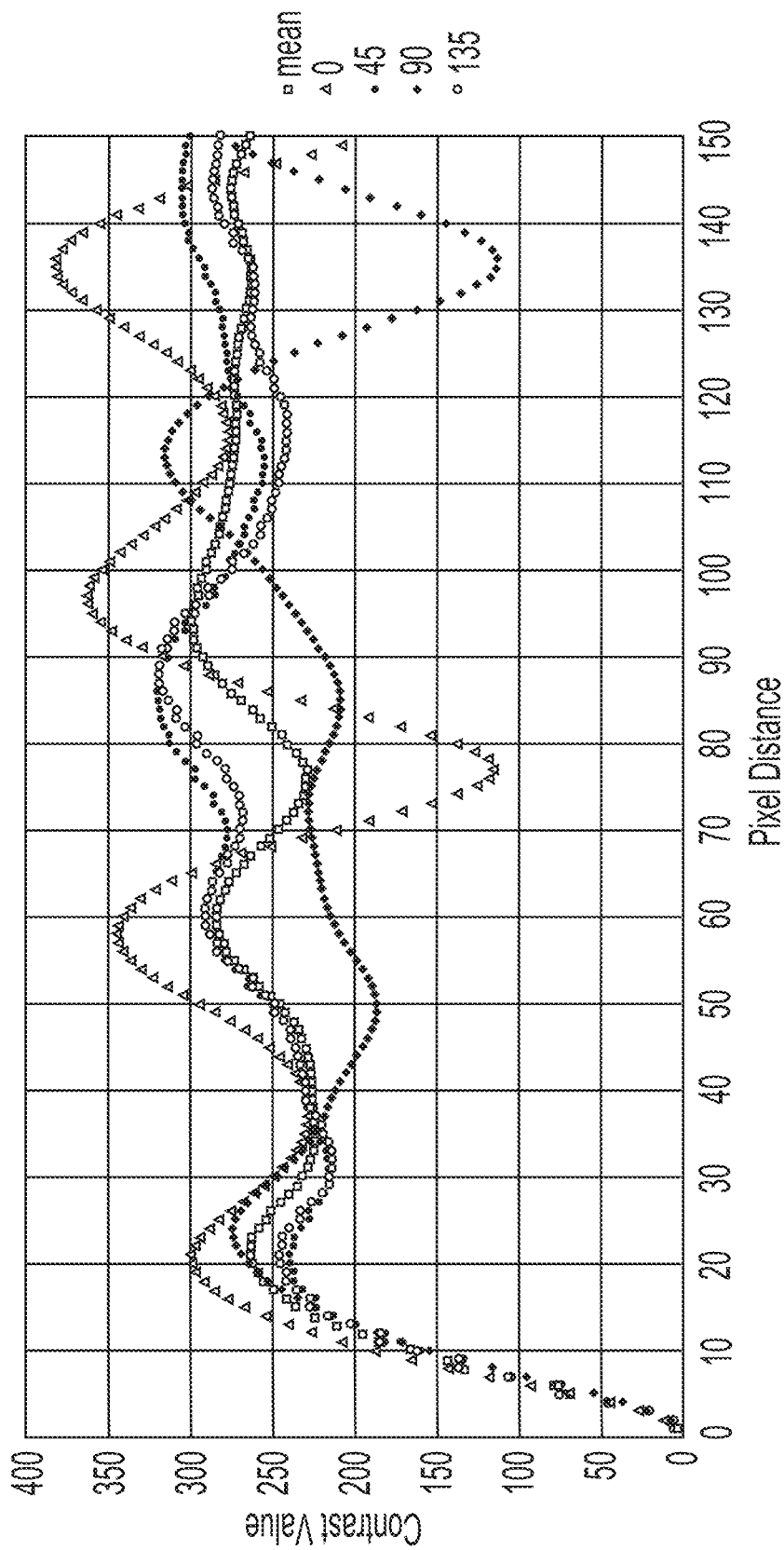
FIG. 59 is a graph charting individual data points generated from a sample of the shaped nonwoven fabric of the present disclosure using the Haralick Maximum Contrast Test Method.

For clarity, the chart of FIG. 59 provides a visual depiction of Example 12's 150 individual data points for the Haralick 0° Contrast values, 150 individual data points for the Haralick 45° Contrast values, 150 individual data points for the Haralick 90° Contrast values 150 individual data points for the Haralick 135° Contrast values, and the Haralick Mean Contrast values generated from those 600 data points, taken at Location 1 (FIG. 58). These same charts were produced for Example 12, Locations 2 and 3, as well as Example 13, first and second locations, but are not reproduced herein for brevity.

TABLE 7B

Haralick Max 90° Contrast, Max 0° Contrast, and Max Mean Contrast

| Sample No./Location | Haralick Maximum 90° Contrast | Haralick Maximum 0° Contrast | Haralick Max Mean Contrast |
| --- | --- | --- | --- |
| Example 12, Location 1 | 315 | 381 | 300 |
| Example 12, Location 2 | 366 | 432 | 436 |
| Example 12, Location 3 | 415 | 401 | 407 |
| Example 13, First Location | 77 | 60 | 67 |
| Example 13, Second Location | 77 | 71 | 77 |

Example 12 was measured for Gray Level Contrast Slope using the Gray Level Contrast Slope Test Method detailed below in ten random locations on the nonwoven. The Gray Level Contrast Slope measured for Example 12 had a high value of 23.9 and a low value of 11.0. The mean Gray Level Contrast Slope measured for Example 12 is 16.7.

TABLE 7C

Gray Level Contrast Slope

| Location | High GL | Low GL | Distance (mm) | Slope |
| --- | --- | --- | --- | --- |
| 1 | 193.7 | 142.4 | 3.0 | 17.1 |
| 2 | 181.4 | 150.6 | 2.8 | 11.0 |
| 3 | 186.2 | 156.3 | 1.6 | 18.7 |
| 4 | 195.4 | 146.4 | 3.0 | 16.3 |
| 5 | 179.0 | 144.5 | 2.0 | 17.3 |
| 6 | 174.6 | 141.2 | 1.4 | 23.9 |
| 7 | 196.1 | 155.5 | 3.2 | 12.7 |
| 8 | 184.9 | 155.1 | 2.6 | 11.5 |
| 9 | 184.6 | 161.1 | 1.4 | 16.8 |
| 10 | 184.4 | 145.9 | 1.8 | 21.4 |

Figure 60:
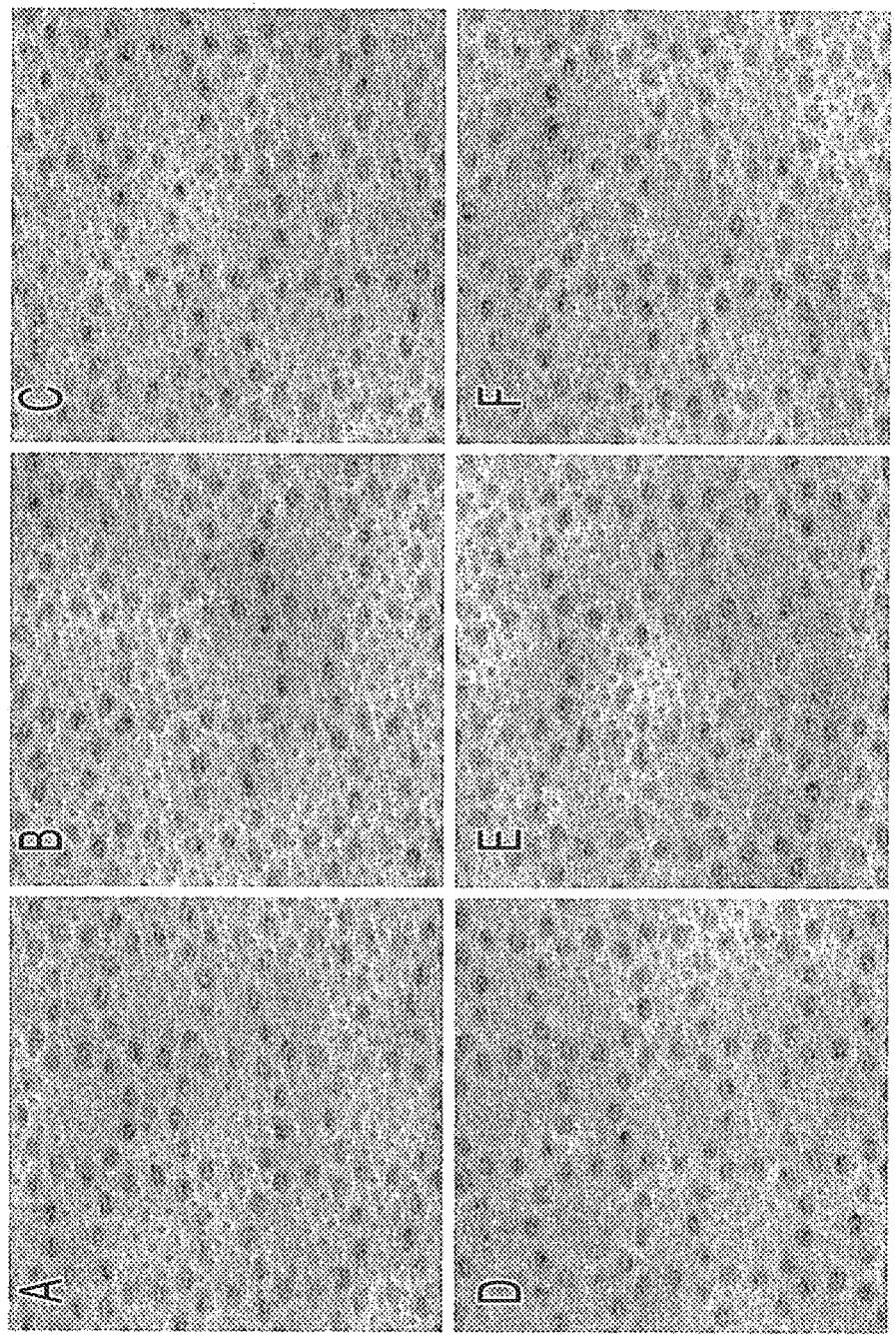
FIG. 60 includes images of six separate samples of the shaped nonwoven fabrics of the present disclosure that are being utilized for measuring Gray Level Variation using the Inter-Article Gray Level Variation Test Method.

Six nonwovens as detailed in Example 12 were measured for Gray Level Variation values using the Inter-Article Gray Level Variation Test Method detailed below in the same visually discernible zones on the shaped nonwoven fabrics. Images of the scanning areas of the six nonwovens are shown in FIG. 60, and are identified as A, B, C, D, E and F. The Mean Gray Level Value is identified below for the six nonwovens, and the standard deviation of those values is the Gray Level Variation value.

TABLE 7D

Gray Level Variation measured by Inter-Article Gray Level Variation Test Method

| Sample | Mean Gray Level Value |
| --- | --- |
| A | 136.7 |
| B | 137.6 |
| C | 133.3 |
| D | 134.5 |
| E | 134.7 |
| F | 133.4 |

The standard deviation amongst the six samples, or the Gray Level Variation value, is 1.8.

In one way to evidence the uniformity within a single article (i.e., defining the contrast in pixels separated by a distance X), the Gray Level Variation values for a visually discernable zone (e.g., a first visually discernable zone) can be between about 0.1 to about 10.0, or between about 0.1 to about 7.0, or between about 0.1 to about 5.0, or between about 0.1 to about 4.7, or between about 0.1 to about 4.2, or between about 0.1 and 4.1, or between about 0.1 and about 4.0, or between about 0.1 and 3.8, or between about 1.2 and 3.8, or less than 4.5, or less than 4.2, or less than 4.0, or less than 3.8, or less than 3.0, or less than 2.0, or less than 1.0. In general, the Gray Level Variation measured value for a visually discernable zone (in a single article) can be any number value up to about 10, and any range of numbers between 0.1 and 10. This Gray Level Variation within a single article is measured according to the Intra-Article Gray Level Variation Test Method detailed herein.

In a first way to evidence the visual sharpness within a single article, the Haralick Maximum Mean Contrast value for a visually discernable zone (e.g., a first visually discernable zone) can be between about 80 and about 750, or between about 90 and about 600, or between about 100 to about 500, or between about 200 and about 500, or between about 300 to about 450, or greater than about 80, or greater than about 90, or greater than about 100, or greater than about 150, or greater than about 200, or greater than about 250, or greater than 300. In general, the Haralick Maximum Mean Contrast value within a visually discernible zone can be any range of integers between 80 and 750.

In a second way to evidence this visual sharpness within a single article, the Haralick Maximum 90° Contrast value for a visually discernable (e.g., a first visually discernable zone) can be between about 80 and about 750, or between about 90 and about 600, or between about 100 to about 500, or between about 200 and about 500, or between about 300 to about 450, or greater than about 80, or greater than about 90, or greater than about 100, or greater than about 150, or greater than about 200, or greater than about 250, or greater than about 300, or greater than 315. In general, the Haralick Maximum 90° Contrast value within a visually discernible zone can be any range of integers between 80 and 750.

In a third way to evidence this visual sharpness within a single article, the Haralick Maximum 0° Contrast Value for a visually discernable zone (e.g., a first visually discernable zone) can be between about 80 and about 750, or between about 90 and about 600, or between about 100 to about 500, or between about 200 and about 500, or between about 300 to about 450, or greater than about 80, or greater than about 90, or greater than about 100, or greater than about 150, or greater than about 200, or greater than about 250, or greater than about 300, or greater than about 350, or greater than 381. In general, the Haralick Maximum 0° Contrast value within a visually discernible zone can be any range of integers between 80 and 750.

In a fourth way to evidence this visual sharpness within a single article, the Gray Level Contrast Slope for a first visually discernable zone (e.g., a first visually discernable zone) can be between about 5.0 and about 35.0, or between about 10.0 and about 30.0, or between about 11.0 and about 25.0, or between about 11.0 and about 23.9, or greater than about 11.0, or less than 23.9. In general, the Gray Level Contrast Slope within a single article can be any range of numbers between 10.0 and 30.0.

In a fifth way to evidence this visual sharpness within a single article, a visually discernible zone (e.g., a first visually discernable zone) may have a periodic Haralick Wave Response, as determined according to the Haralick Maximum Contrast Method defined herein. For clarity, if one observes at least one crest and at least one trough in the Haralick response, then the wave response can be defined as periodic. As further defined in the method, the periodic response is only applicable for Haralick Maximum 90° or 0° Contrast values.

In one way to evidence a consistently high uniformity amongst multiple articles, such uniformity may be evidenced by a Gray Level Variation value from between about 0.1 to about 10.0, or between about 0.1 to about 7.0, or between about 0.1 to about 5.0, or between about 0.1 to about 4.7, or between about 0.1 to about 4.2, or between about 0.1 and 4.1, or between about 0.1 and about 4.0, or between about 0.1 and about 3.8, or between about 0.1 and about 1.2, or less than 4.5, or less than 4.2, or less than 4.0, or less than 3.8, or less than 3.0, or less than 2.0, or less than 1.2, or less than 1.0. In general, the Gray Level Variation measured value for a visually discernable zone (e.g., a first visually discernable zone—amongst multiple articles) can be any number value up to about 10, and any range of numbers between 0.1 and 10. This Gray Level Variation between multiple articles is measured according to the Inter-Article Gray Level Variation Test Method detailed herein.

Any of the above detailed individual Haralick parameters to evidence visual sharpness in a shaped nonwoven may be combined with one or more additional ways (additional Haralick parameters or other parameters) to evidence visual sharpness in a shaped nonwoven. Further, the shaped nonwoven fabrics detailed above have microzones with regions having differences in intensive properties, such as basis weight, density, or thickness, for example. Those same shaped nonwoven fabrics can also simultaneously have visually sharp patterns with any and/or all of the Haralick Analysis values detailed herein. Any of the shaped nonwoven fabric examples detailed herein (e.g., samples that include zones and/or microzones with regions having differences in thickness, basis weight and/or volumetric density, hydrophilic and/or hydrophobic areas, and/or surfaces with the various TS7 values disclosed herein) can further have visually sharp patterns that can be quantified by Gray Level Variation, Haralick Max Mean Contrast Value, Haralick Maximum 90° Contrast Value. Haralick Maximum 0° Contrast Value, Gray Level Contrast Slope, and the existence or not of a Periodic Haralick Wave Response. Further, packages of any of the shaped nonwoven fabric examples detailed herein (e.g., samples that include zones and/or microzones with regions having differences in thickness, basis weight and/or volumetric density, and/or surfaces with the various TS7 values disclosed herein) can include nonwovens that further have visually sharp patterns that can be quantified by Inter-Gray Level Variation.

Shaped nonwoven fabrics having the above detailed microzones with regions having differences in basis weight, density, or thickness, for example, while also simultaneously having visually sharp patterns with any and/or all of the Haralick Analysis values detailed herein can provide many useful applications such as topsheet materials for baby care, fem care and adult incontinence products, as well as use in medical pads, wipes and cleaning pads, etc.

Further, in order to manufacture such shaped nonwoven fabrics with high visual resolution patterns, utilizing the methods as detailed herein, the inventors have unexpectedly found it is necessary for the forming belt to have a select combination of Knuckle Area Percentage (hereinafter, "% KA") and/or air permeability, and/or overburden. While not wishing to be bound by theory, the inventors have found the shaped nonwoven fabrics with high visual resolution patterns of the present invention may be realized only with forming belts have having select % KA and/or air permeability and/or overburden as these belt designs may facilitate migration of fibers deeper into the open areas of the forming belt, greater filament count in the open areas relative to the knuckle or resin areas of the belt, more cooling induced fiber setting upon deposition in the open areas of the belt, less loss of fiber consolidation at the resin wall area of the belt, retention of fiber wall steepness and structure during post making consolidation/bonding, retention fiber wall steepness and structure in an intermediate roll for feeding to a production line, fiber wall steepness and structure in articles even under compression packaging, and/or other factors, all individually or simultaneously contributing to the establishment of a steep transition slope of filaments at region boundaries of the nonwoven and the unexpected achievement of high visual resolution texture.

In the context of the entire forming belt, the % KA may be calculated by dividing the area of the forming belt that contains knuckles (i.e., the summed areas with resin forming raised portions) by the overall area of the entire forming belt. In defined sections on the forming belt, the % KA may be calculated by dividing the area of the defined section that contains knuckles (i.e., the summed areas with resin forming raised portions) by the overall area of the defined section. The method to measure air permeability of the forming belts defined herein is detailed in the Methods section below.

% KA, air permeability, and overburden may be measured in any defined section on the forming belts defined herein, including: 1) defined sections that include a portion, or the entire, repeat pattern of a forming belt (e.g., the entire section of the forming belt shown in FIG. 12, 16 or 18, or any portion of the forming belt shown in FIG. 12, 16 or 18); 2) defined sections that include a discrete belt pattern on a forming belt (e.g., discrete belt pattern 61 as shown in forming belt section of FIG. 19); 3) defined sections that include any discernable zone on a forming belt (e.g., any defined section of discrete belt pattern 61 in FIG. 19 that includes a visually discernible zone); and 4) defined sections that include any combination of discernible zones on a forming belt (e.g., any defined section of discrete belt pattern 61 in FIG. 19 that includes a combination of one or more visually discernible zones).

For the forming belts defined herein that deliver high visual resolution patterned nonwovens, the % KA may be between about 2% and about 35%, or between about 5% and about 30%, or between about 8% and about 25%, or between about 10% and about 25%. The air permeability may be between about 400 to about 1000 cfm, or between about 400 to about 800 cfm, or between about 500 cfm and about 750 cfm, or between about 650 to about 700 cfm. Overburden, OB, as defined herein, may be between about 0.015 inch and about 0.060 inch, or between about 0.020 and about 0.050 inch, or between about 0.025 inch and about 0.045 inch, or between about 0.030 inch and about 0.040 inch, or between about 0.030 inch and about 0.035 inch.

Figure 61:
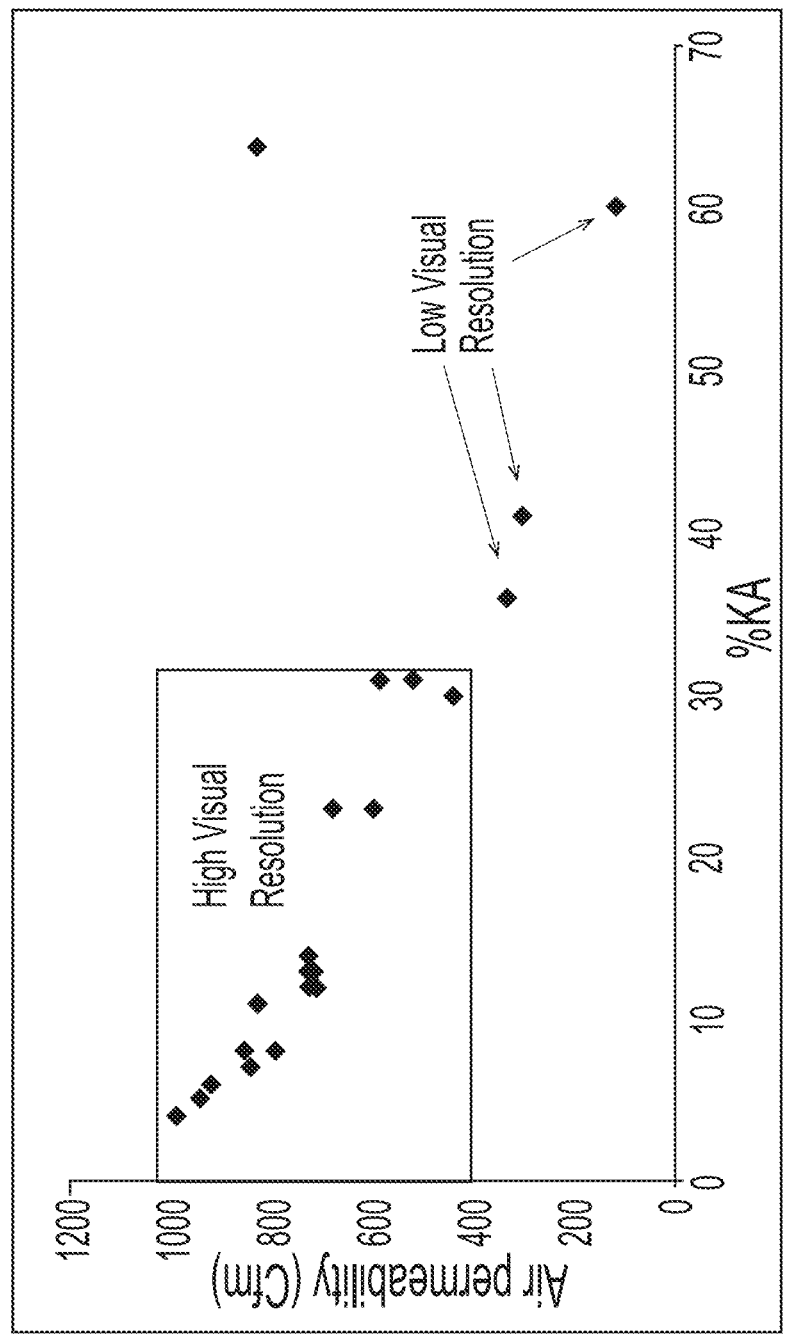
FIG. 61 is a graph charting individual data points generated from samples of structured belts used to produce structured nonwoven fabrics.

Table 8A and FIG. 61, which graphs the data from Table 8A, illustrate the desired combination ranges of % KA and air permeability for forming belts to be utilized in the manufacture of shaped nonwoven fabrics with high visual resolution patterns. When a forming belt has a % KA that is between about 2% and about 35% and an air permeability that is between about 400 cfm and about 1000 cfm, the belt may produce the shaped nonwoven fabrics with high visual resolution patterns as described herein (i.e., nonwovens that exhibit high visual sharpness as quantified by Gray Level Variation, Haralick Max Mean Contrast Value, Haralick Maximum 90° Contrast Value, Haralick Maximum 0° Contrast Value, Gray Level Contrast Slope, and the existence or not of a Periodic Haralick Wave Response). Such forming belts are identified as High Visual Resolution. In FIG. 61, a box has been drawn around the High Visual Resolution forming belts data points to indicate the ranges of % KA and air permeability parameters that are displayed by such belts. When a forming belt has a % KA that is higher than 35%, or an air permeability that is lower than about 350 cfm, or a combination of the % KA higher than 35% and an air permeability of lower than 400 cfm, the belt does not produce the shaped nonwoven fabrics with high visual resolution patterns as described herein. Such forming belts are identified as Low Visual Resolution. Data for some Low Visual Resolution belt examples is detailed in Table 8B below and also graphed on FIG. 61.

TABLE 8A

% KA and Air Permeability for High Visual Resolution Forming Belts

| % KA | Air Permeability |
| --- | --- |
| 4.0 | 988 |
| 5.0 | 943 |
| 6.0 | 921 |
| 7.0 | 844 |
| 8.0 | 855 |
| 8.0 | 857 |
| 11.0 | 829 |
| 12.0 | 712 |
| 12.0 | 721 |
| 13.0 | 729 |
| 13.0 | 719 |
| 14.0 | 730 |
| 14.0 | 738 |
| 14.0 | 725 |
| 23.0 | 680 |
| 23.0 | 599 |
| 30.0 | 442 |
| 31.0 | 522 |
| 31.0 | 584 |

TABLE 8B

% KA and Air Permeability for Low Visual Resolution Forming Belts

| % KA | Air Permeability |
| --- | --- |
| 36.0 | 336 |
| 41.0 | 305 |
| 60.0 | 117 |

In some interesting High Visual Resolution forming belts, the belt may have a % KA of between about 8% to about 25% and an air permeability of between about 500 to about 850 cfm. In other interesting High Visual Resolution forming belts, the belt may have a % KA of between about 10% to about 25% and an air permeability of between about 650 to about 700 cfm. In other interesting High Visual Resolution forming belts, the belt may have a % KA of between about 8% to about 25% and an air permeability of between about 500 to about 850 cfm and an overburden of between about 0.015 inches and about 0.060 inches. In other interesting High Visual Resolution forming belts, the belt may have a % KA of between about 10% to about 25% and an air permeability of between about 650 to about 700 cfm and an overburden of between about 0.025 inches and about 0.045 inches.

Any of the above detailed individual Haralick parameters to evidence visual sharpness in a shaped nonwoven may be combined with one or more parameters related to the structured forming belts (% KA and/or air permeability and/or overburden) utilized to manufacture the shaped nonwovens. Further, the shaped nonwoven fabrics made on the forming belts detailed above have microzones with regions having differences in intensive properties, such as basis weight, density, or thickness, for example, and can also simultaneously have visually sharp patterns with any and/or all of the Haralick Analysis values detailed herein. Any of the shaped nonwoven fabric examples detailed herein (e.g., samples that include zones and/or microzones with regions having differences in thickness, basis weight and/or volumetric density, hydrophilic and/or hydrophobic areas, and/or surfaces with the various TS7 values disclosed herein) can further simultaneously have visually sharp patterns that can be quantified by Gray Level Variation, Haralick Max Mean Contrast Value, Haralick Maximum 90° Contrast Value, Haralick Maximum 0° Contrast Value, Gray Level Contrast Slope, and the existence or not of a Periodic Haralick Wave Response. and/or be made on structured forming belts as described herein (% KA and/or air permeability and/or overburden). Further, packages of any of the shaped nonwoven fabric examples detailed herein (e.g., samples that include zones and/or microzones with regions having differences in thickness, basis weight and/or volumetric density, and/or surfaces with the various TS7 values disclosed herein) can include nonwovens that further simultaneously have visually sharp patterns that can be quantified by Inter-Gray Level Variation.

Test Methods:

Compression Aging Test Method

Initial Caliper Measurement:
    Cut five 3 inch by 3 inch samples per nonwoven fabric to be measured.
    Number each sample from 1 to 5.
    Measure caliper at 0.5 kPa with Standard 65 mm foot using Thwing-Albert caliper tester according to standard procedures.
    Report initial caliper for each of the five samples.
    Report the average caliper of the five samples.

Aged Compression Method and Aged Caliper Measurement
    Stack the five samples in an alternating mode with each separated by a paper towel, the stack starting and ending with a Sample Number 1 and 5, respectively.
    Place the alternating stacked samples in an aluminum sample holder with an appropriate weight on top of the samples (4 KPa, 14 KPa or 35 KPa).
    Place the stacked samples with the weight in oven at 40° C. for 15 hours.

Remove the weight after 15 hours, separate the samples and measure the caliper of each sample at 0.5 kPa with Standard 65 mm foot Thwing-Albert caliper tester according to standard procedures.

Report aged caliper value for each of the five samples.

Report the average aged caliper of the five samples.

Analysis Reports:

Report average initial and aged calipers by position number

Report Caliper Recovery Index:

(Average Aged Caliper/Average Initial Caliper)*100

Localized Basis Weight Test Method

Localized basis weight of the nonwoven fabric may be determined by several available techniques, but a simple representative technique involves a punch die having an area of 3.0 cm$^2$ which is used to cut a sample piece of the web from the selected region from the overall area of a nonwoven fabric. The sample piece is then weighed and divided by its area to yield the localized basis weight of the nonwoven fabric in units of grams per meter squared. Results are reported as a mean of 2 samples per selected region.

Fuzz Level Test Method

The Fuzz Level Test is used to determine the quantity of fibers removed from a nonwoven materials under an abrasive force (i.e., the fuzz level).

The Fuzz Level Test utilizes the following materials:

Sutherland Ink Rub Tester with 2 lb. weight, available from Danilee Co, San Antonio, TX Aluminum oxide cloth 320 grit shop rolls made by Plymouth Coatings, (617) 447-7731. This material can also be ordered through McMaster Carr, part number 468.7A51. (330) 995-5500.

Two sided tape, 3M #409, available from Netherland Rubber Company. (513) 733-1085.

Fiber Removal Tape, 3M #3187, available from Netherland Rubber Company, (513) 733-1085.

Analytical Balance (+/−0.0001 g)

Paper cutter 2200 g weight (metal) 170 mm×63 mm.

Thick-style release paper liner cardboard −0.0445 in (1.13 mm) caliper.

Materials Preparation

Measure and cut aluminum oxide cloth to 7.5 in (19.0 cm) in length. Measure and cut pieces of 3M #3187 tape 6.5 inches (16.5 cm) in length, two tapes for each specimen. Fold under approximately 0.25 inch (0.6 cm) on each end of the 3M #3187 tape to facilitate handling. Lay 3M #3187 tape on the thick-style release paper for use later.

Sample Preparation

Before handling or testing any of the materials, wash hands with soap and water to remove excess oils from hands. Optionally, latex gloves may be worn. Cut a sample of the nonwoven fabric to be tested to a size at least 11 cm in the MD and 4 cm in the CD. Lay out the sample of nonwoven fabric to be tested with the side to be tested facing down. Cut a piece of 3M #409 two-sided tape off roll at least 11 cm long. Remove the backing and apply the side of two-sided tape that was facing the backing to the sample nonwoven fabric lengthwise in the machine direction (MD). Replace the backing over the exposed tape. Using the paper cutter, cut test samples within the taped area 11 cm MD and 4 cm CD.

Test Procedure

1. Mount the cut piece of aluminum oxide cloth on Sutherland Ink Rub Tester using the 2 lb. weight. Lay a second cut piece of aluminum oxide cloth on top of the thick-style release paper liner cardboard (a new piece is used for each test). Lay both on top of the 2 lb. weight. The sides will fold down into clips—make sure aluminum oxide cloth and the thick-style release paper liner cardboard are flat.
2. Mount the specimen onto Sutherland Ink Rub Tester platform, centering on the metal plate. Place the 2200 g weight on top of specimen for 20 seconds.
3. Attach the metal plate and 2 lb. weight to Sutherland Ink Rub Tester.
4. Turn Rub Tester on. If the counter light is not illuminated press the reset button. Press the counter button to set the rub cycles to 20 cycles. Select Speed 1, the slow speed, (light is not illuminated) by using the Speed button. Press "Start".
5. When Rub Tester has shut off, carefully remove the aluminum oxide cloth/weight, being sure not to lose any of the loose microfibers (fuzz). In some cases, the microfibers will be attached to both the aluminum oxide cloth and the surface of Sample nonwoven. Lay the weight upside down on the bench.
6. Weigh the fiber removal tapes with release paper attached. Holding the fiber removal tape by its folded ends, remove release paper and set aside. Gently put the tape onto the aluminum oxide cloth to remove all of the fuzz. Remove the fiber removal tape and put back on release paper. Weigh and record the weight of the fiber removal tapes.
7. Hold another piece of the pre-weighed fiber removal tape by its folded ends. Gently put the fiber removal tape onto the surface of the rubbed nonwoven sample. Lay a flat metal plate on top of the fiber removal tape.
8. Lay the 2200 g weight on top of the metal plate for 20 seconds. Remove the fiber removal tape. Hold the pre-weighed fiber removal tape by its folded ends to avoid fingerprints. Put pre-weighed fiber removal tape back on release paper. Weigh and record the weight of the fiber removal tapes.
9. The fuzz weight is the sum of weight-increase of both fiber removal tapes.
10. The fuzz weight is reported as the average of 10 measurements.

Calculations

For a given sample, add the weight in grams of fuzz collected from the aluminum oxide cloth and the weight in grams of fuzz collected from the abraded Sample nonwoven. Multiply the combined weight in grams by 1000 to convert to milligrams (mg). To convert this measurement from absolute weight loss to weight loss per unit area, divide the total weight of fuzz by the area of the abraded area.

Air Permeability Test Method

The Air Permeability Test is used to determine the level of air flow in cubic feet per minute (cfm) through a forming belt. The Air Permeability Test is performed on a Textest Instruments model FX3360 Portair Air Permeability Tester, available from Textest AG, Sonnenbergstrasse 72, CH 8603 Schwerzenbach, Switzerland. The unit utilizes a 20.7 mm orifice plate for air permeability ranges between 300-1000 cfm. If air permeability is lower than 300 cfm the orifice plate needs to be reduced; if higher than 1000 cfm the orifice plate needs to be increased. Air permeability can be measured in localized zones of a forming belt to determine differences in air permeability across a forming belt.

Test Procedure

1. Power on the FX3360 instrument.
2. Select a pre-determined style having the following setup:

a. Material: Standard
b. Measurement Property: Air Permeability (AP)
c. Test Pressure: 125 Pa (pascals)
d. T-factor: 1.00
e. Test point pitch: 0.8 inch.
3. Position the 20.7 mm orifice plate on the top side of the forming belt (the side with the three-dimensional protrusions) at the position of interest.
4. Selecting "Spot Measurement" on the touch screen of the testing unit.
5. Reset the sensor prior to measurement, if necessary.
6. Once reset, select the "Start" button to begin measurement.
7. Wait until the measurement stabilizes and record the cfm reading on the screen.
8. Select the "Start" button again to stop measurement.

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 27). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Micro-CT Intensive Property Measurement Test Method

The micro-CT intensive property measurement method measures the basis weight, thickness and volumetric density values within visually discernable regions of a substrate sample. It is based on analysis of a 3D x-ray sample image obtained on a micro-CT instrument (a suitable instrument is the Scanco μCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (a suitable image analysis software is MATLAB available from The Mathworks. Inc., Natick, MA, or equivalent) to measure the basis weight, thickness and volumetric density intensive properties of regions within the sample.

Sample Preparation:

To obtain a sample for measurement, lay a single layer of the dry substrate material out flat and die cut a circular piece with a diameter of 30 mm.

If the substrate material is a layer of an absorbent article, for example a topsheet, backsheet nonwoven, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze, Control Company, Houston TX) can be used to remove a substrate layer from additional underlying layers, if necessary, to avoid any longitudinal and lateral extension of the material. Once the substrate layer has been removed from the article proceed with die cutting the sample as described above.

If the substrate material is in the form of a wet wipe, open a new package of wet wipes and remove the entire stack from the package. Remove a single wipe from the middle of the stack, lay it out flat and allow it to dry completely prior to die cutting the sample for analysis.

A sample may be cut from any location containing the visually discernible zone to be analyzed. Within a zone, regions to be analyzed are ones associated with a three-dimensional feature defining a microzone. The microzone comprises a least two visually discernible regions. A zone, three-dimensional feature, or microzone may be visually discernable due to changes in texture, elevation, or thickness. Regions within different samples taken from the same substrate material can be analyzed and compared to each other. Care should be taken to avoid folds, wrinkles or tears when selecting a location for sampling.

Image Acquisition:

Set up and calibrate the micro-CT instrument according to the manufacturer's specifications. Place the sample into the appropriate holder, between two rings of low density material, which have an inner diameter of 25 mm. This will allow the central portion of the sample to lay horizontal and be scanned without having any other materials directly adjacent to its upper and lower surfaces. Measurements should be taken in this region. The 3D image field of view is approximately 35 mm on each side in the xy-plane with a resolution of approximately 5000 by 5000 pixels, and with a sufficient number of 7 micron thick slices collected to fully include the z-direction of the sample. The reconstructed 3D image resolution contains isotropic voxels of 7 microns. Images are acquired with the source at 45 kVp and 133 ρA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 1000 ms and 3 averages. The projection images are reconstructed into the 3D image, and saved in 16-bit RAW format to preserve the full detector output signal for analysis.

Image Processing:

Load the 3D image into the image analysis software. Threshold the 3D image at a value which separates, and removes, the background signal due to air, but maintains the signal from the sample fibers within the substrate.

Three 2D intensive property images are generated from the threshold 3D image. The first is the Basis Weight Image. To generate this image, the value for each voxel in an xy-plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values a basis weight calibration curve is generated. Obtain a substrate that is of substantially similar composition as the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above process the micro-CT image, and generate a Basis Weight Image containing raw data values. The real basis weight value for this sample is the average basis weight value measured on the calibration samples. Next, stack two layers of the calibration substrate samples on top of each other, and acquire a micro-CT image of the two layers of calibration substrate. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an R2 value of at least 0.95, if not repeat the entire calibration procedure. This calibration curve is now used to convert the raw data values into real basis weights.

The second intensive property 2D image is the Thickness Image. To generate this image the upper and lower surfaces of the sample are identified, and the distance between these surfaces is calculated giving the sample thickness. The upper surface of the sample is identified by starting at the uppermost z-direction slice and evaluating each slice going through the sample to locate the z-direction voxel for all pixel positions in the xy-plane where sample signal was first detected. The same procedure is followed for identifying the lower surface of the sample, except the z-direction voxels located are all the positions in the xy-plane where sample signal was last detected. Once the upper and lower surfaces have been identified they are smoothed with a 15×15 median filter to remove signal from stray fibers. The 2D Thickness Image is then generated by counting the number of voxels that exist between the upper and lower surfaces for each of the pixel positions in the xy-plane. This raw thickness value is then converted to actual distance, in microns, by multiplying the voxel count by the 7 μm slice thickness resolution.

The third intensive property 2D image is the Volumetric Density Image. To generate this image divide each xy-plane pixel value in the Basis Weight Image, in units of gsm, by the corresponding pixel in the Thickness Image, in units of microns. The units of the Volumetric Density Image are grams per cubic centimeter (g/cc).

Micro-CT Basis Weight, Thickness and Volumetric Density Intensive Properties:

Begin by identifying the region to be analyzed. A region to be analyzed is one associated with a three-dimensional feature defining a microzone. The microzone comprises a least two visually discernible regions. A zone, three-dimensional feature, or microzone may be visually discernable due to changes in texture, elevation, or thickness. Next, identify the boundary of the region to be analyzed. The boundary of a region is identified by visual discernment of differences in intensive properties when compared to other regions within the sample. For example, a region boundary can be identified based by visually discerning a thickness difference when compared to another region in the sample. Any of the intensive properties can be used to discern region boundaries on either the physical sample itself of any of the micro-CT intensive property images. Once the boundary of the region has been identified, draw an oval or circular "region of interest" (ROI) within the interior of the region. The ROI should have an area of at least 0.1 mm2, and be selected to measure an area with intensive property values representative of the identified region. From each of the three intensive property images calculate the average basis weight, thickness and volumetric density within the ROI. Record these values as the region's basis weight to the nearest 0.01 gsm, thickness to the nearest 0.1 micron and volumetric density to the nearest 0.0001 g/cc.

Emtec Test Method

TS7 and TS750 values are measured using an EMTEC Tissue Softness Analyzer ("Emtec TSA") (Emtec Electronic GmbH, Leipzig, Germany) interfaced with a computer running Emtec TSA software (version 3.19 or equivalent). According to Emtec, the TS7 value correlates with the real material softness, while the TS750 value correlates with the felt smoothness/roughness of the material. The Emtec TSA comprises a rotor with vertical blades which rotate on the test sample at a defined and calibrated rotational speed (set by manufacturer) and contact force of 100 mN. Contact between the vertical blades and the test piece creates vibrations, which create sound that is recorded by a microphone within the instrument. The recorded sound file is then analyzed by the Emtec TSA software. The sample preparation, instrument operation and testing procedures are performed according to the instrument manufacture's specifications.

Sample Preparation

Test samples are prepared by cutting square or circular samples from a finished product. Test samples are cut to a length and width (or diameter if circular) of no less than about 90 mm, and no greater than about 120 mm, in any of these dimensions, to ensure the sample can be clamped into the TSA instrument properly. Test samples are selected to avoid perforations, creases or folds within the testing region. Prepare 8 substantially similar replicate samples for testing. Equilibrate all samples at TAPPI standard temperature and relative humidity conditions (23° C.±2° C. and 50%±2%) for at least 2 hour prior to conducting the TSA testing, which is also conducted under TAPPI conditions.

Testing Procedure

Calibrate the instrument according to the manufacturer's instructions using the 1-point calibration method with Emtec reference standards ("ref.2 samples"). If these reference samples are no longer available, use the appropriate reference samples provided by the manufacturer. Calibrate the instrument according to the manufacturer's recommendation and instruction, so that the results will be comparable to those obtained when using the 1-point calibration method with Emtec reference standards ("ref.2 samples").

Provide eight replicate samples of a fabric for testing. Mount a test sample into the instrument with a surface facing upwards, and perform the test according to the manufacturer's instructions. When complete, the software displays values for TS7 and TS750. Record each of these values to the nearest 0.01 dB $V^2$ rms. The test sample is then removed from the instrument and discarded. This testing is performed individually on the same surface of four of the replicate samples, and then on the other surface of the other four replicate samples. The first tested surface may be either of the first surface 12 or the second surface 14 of a shaped nonwoven fabric as disclosed herein.

The four test result values for TS7 and TS750 from the first tested surface are averaged (using a simple numerical average); the same is done for the four test result values for TS7 and TS750 from the second tested surface. Report the individual average values of TS7 and TS750 for both the first and second tested surfaces on a particular test sample to the nearest 0.01 dB $V^2$ rms. Additionally, the TS7 ratio of the first tested surface to the second tested surface is calculated by dividing the average TS7 of the first tested surface divided by the average TS7 of the second tested surface.

Contact Angle and Time to Wick Test Methods

Contact Angle and Time to Wick measurements are determined using a sessile drop experiment. A specified volume of Type II reagent distilled water (as defined in ASTM D1193) is applied to the surface of a test sample using an automated liquid delivery system. A high speed video camera captures time-stamped images of the drop over a 60 second time period at a rate of 900 frames per second. The contact angle between the drop and the surface of the test sample is determined for each captured image by image analysis software. The time to wick is determined as the time it takes the contact angle of a drop absorbing into the test sample to decrease to a contact angle <10°. All measurements are performed at constant temperature (23° C.±2° C.) and relative humidity (50%±2%).

An automated contact angle tester is required to perform this test. The system consists of a light source, a video camera, a horizontal specimen stage, a liquid delivery system with a pump and micro syringe and a computer equipped with software suitable for video image capture, image analysis and reporting contact angle data. A suitable instrument is the Optical Contact Angle Measuring System OCA 20 (DataPhysics Instruments, Filderstadt, Germany), or equivalent. The system must be able to deliver an 8.2 microliter drop and be capable of capturing images at a rate of 900 frames per second. The system is calibrated and operated per the manufacturer's instructions, unless explicitly stated otherwise in this testing procedure. To obtain a test sample for measurement, lay a single layer of the dry substrate material out flat and cut a rectangular test sample 15 mm in width and about 70 mm in length. The width of the sample may be reduced as necessary to ensure that the test region of interest is not obscured by surrounding features during testing. With a narrower sample strip care must be taken that the liquid drop does not reach the edge of the test sample during testing, otherwise the test must be repeated. Precondition samples at 23° C.±2° C. and 50%±2% relative humidity for 2 hours prior to testing.

Sample Preparation

A test sample may be cut from any location containing the visually discernible zone to be analyzed. Within a zone, regions to be analyzed are ones associated with a three-dimensional feature defining a microzone. The microzone comprises at least two visually discernible regions. A zone, three-dimensional feature, or microzone may be visually discernable due to changes in texture, elevation, or thickness. Regions within different test samples taken from the same substrate material can be analyzed and compared to each other. Care should be taken to avoid folds, wrinkles or tears when selecting a location for sampling.

If the substrate material is a layer of an absorbent article, for example a topsheet or backsheet nonwoven, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze, Control Company, Houston TX) can be used to remove a substrate layer from additional underlying layers, if necessary, to avoid any longitudinal and lateral extension of the material. Once the substrate layer has been removed from the article proceed with cutting the test sample. If the substrate material is in the form of a wet wipe, open a new package of wet wipes and remove the entire stack from the package. Remove a single wipe from the middle of the stack, lay it out flat and allow it to dry completely prior to cutting the sample for analysis.

Testing Procedure

The test sample is positioned onto the horizontal specimen stage with the test region in the camera's field of view beneath the liquid delivery system needle, with the test side facing up. The test sample is secured in such a way that it lies flat but unstrained, and any interaction between the liquid drop and the underlying surface is avoided to prevent undue capillary forces. A 27 gauge blunt tip stainless steel needle (ID 0.23 mm, OD 0.41 mm) is positioned above the test sample with at least 2 mm of the needle tip in the camera's field of view. Adjust the specimen stage to achieve a distance of about 3 mm between the tip of the needle and the surface of the test sample. An 8.2 microliter drop of reagent distilled water is formed at a rate of 1 microliter per second and allowed to freely fall onto the surface of the test sample. Video image capture is initiated prior to the drop contacting the surface of the test sample, and subsequently a continual series of images is collected for a duration of 60 seconds after the drop contacts the surface of the test sample. Repeat this procedure for a total of five (5) substantially similar replicate test regions. Use a fresh test sample or ensure that the previous drop's wetted area is avoided during subsequent measurements.

On each of the images captured by the video camera, the test sample surface and the contour of the drop is identified and used by the image analysis software to calculate the Contact Angle for each drop image and reported to the nearest 0.1 degree. The Contact Angle is the angle formed by the surface of the test sample and the tangent to the surface of the liquid drop in contact with the test sample. For each series of images from a test, time zero is the time at which the liquid drop makes contact with the surface of the test sample. Measure and record the Contact Angle on the drop image that corresponds to time zero plus five (5) seconds. The Contact Angle at five seconds is reported as 0° if the droplet has been completely absorbed by the test sample within 5 seconds. Repeat this procedure for the five replicate test regions. Calculate the arithmetic mean of the Contact Angle at time zero plus five seconds for the five replicate test regions, and report this value as the Contact Angle to the nearest 0.1 degrees.

Time to Wick is defined as the time it takes the contact angle of a drop absorbing into the test sample to decrease to a contact angle <10°. Time to Wick is measured by identifying the first image of a given series where the contact angle has decreased to a contact angle <10°, and then based on that image, calculating and reporting the length of time that has elapsed from time zero. Time to Wick is reported as 60 seconds if a contact angle less than 10° is not reached within 60 seconds. Repeat this procedure for the five replicate test regions. Calculate the arithmetic mean of the Time to Wick for the five replicate test regions, and report this value to the nearest 0.1 milliseconds.

Intra-Article Gray Level Variation Test Method

The Intra-Article Gray Level Variation Test Method is used to determine the uniformity of gray level values within a visually discernable zone of a nonwoven fabric image. A flatbed scanner capable of scanning a minimum of 24 bit color at 150 dpi with manual control of color management (suitable scanner is an Epson Perfection V750 Pro from Epson America Inc., Long Beach CA, or equivalent) is used to acquire images. The scanner is interfaced with a computer running color calibration software capable of calibrating the scanner against a color reflection IT8 target utilizing a corresponding reference file compliant with ANSI method IT8.7/2-1993 (suitable color calibration software is Monaco EZColor or ilStudio available from X-Rite Grand Rapids, MI, or equivalent). The color calibration software constructs an International Color Consortium (ICC) color profile for the scanner, which is used to color correct an output image using an image analysis program that supports application of ICC profiles (a suitable program is Photoshop CS4 available from Adobe Systems Inc., San Jose, CA, or equivalent). The color corrected image is then converted to grayscale for subsequent gray level image analysis (a suitable image analysis software is MATLAB available from The Mathworks, Inc., Natick, MA).

To obtain a specimen, an absorbent article is taped to a rigid flat surface in a planar configuration. Any leg elastics present may be cut to facilitate laying the article flat. The outer boundary of the region lying above the absorbent core of the article is identified and marked on the outward facing surface of the layer. The specimen is removed from the underlying layers of the article by cutting around the outer perimeter of the article with a razor blade. The layer specimen is carefully removed such that its longitudinal and lateral extension is maintained to avoid distortion of the material. A cryogenic spray (such as Cyto-Freeze, Control Company, Houston TX, or equivalent) can be used to remove the specimen from the underlying layers if necessary. The samples are conditioned at about 23° C.±2° C. and about 50%±2% relative humidity for 2 hours prior to testing.

The scanner is turned on 30 minutes prior to calibration and image acquisition. Deselect any automatic color correction or color management options that may be included in the scanner software. If the automatic color management cannot be disabled, the scanner is not appropriate for this application. The recommended procedures of the color calibration software are followed to create and export an ICC color profile for the scanner. The color calibration software compares an acquired IT8 target image to a corresponding reference file to create and export the ICC color profile for a scanner, which will be applied within the image analysis program to correct the color of subsequent output images.

The scanner lid is opened and the sample carefully laid flat on the center of the scanner glass with the outward facing surface of the specimen oriented toward the glass. The specimen is backed with a black glass tile (P/N 11-0050-30, available from HunterLab, Reston, VA, or equivalent) prior to acquiring the image. A 4 inch by 4 inch (101.6 mm by 101.6 mm) scan of a visually discernable zone is acquired and imported into the image analysis software at 24 bit color with a resolution of 150 dpi (approximately 5.9 pixels per mm) in reflectance mode. The ICC color profile is assigned to the image producing a color corrected RGB image. The RGB image is then converted to an 8 bit grayscale according to the following weighted sum of the R, G, and B components.

$$\text{Gray Level}=0.2989 \times R + 0.5870 \times G + 0.1140 \times B$$

The image is smoothed and blurred by applying a 2D Gaussian filter with a standard deviation of the Gaussian distribution (sigma) equal to 4, and the boundary padded by repeating border elements. This calibrated and blurred gray level image is saved in an uncompressed format, such as a TIFF file prior to analysis.

The calibrated and blurred gray level image is opened in the image analysis software, and divided into a 4×4 grid. The arithmetic mean gray level value is measured in each of the 16 regions and recorded. The standard deviation of the recorded means is calculated and reported as the Gray Level Variation to the nearest 0.1.

Haralick Maximum Contrast Test Method

The Haralick Maximum Contrast value is based on the Haralick texture features described in R. M. Haralick, K. Shanmugam, and I. Dinstein, "Textural features for image classification," IEEE Transactions on Systems, Man and Cybernetics, vol. 3, no. 6, pp. 610-621, 1973. The Contrast texture feature is calculated from a computed Gray Level Co-occurrence Matrix (GLCM). The GLCM is a tabulation of how often different combinations of pixel brightness values (grey levels) occur in an image. The GLCM is normalized so that the sum of its elements is equal to 1. Each element (i,j) in the normalized GLCM is the joint probability occurrence of pixel pairs with a defined spatial relationship, direction and distance, having gray level values i and j in the image. The Contrast texture feature is calculated using the following equation:

$$\text{Contrast} = \sum_i \sum_j (i-j)^2 p(i,j)$$

Where i is the row number, j is the column number, and p(i,j) is the probability value recorded for the element (i,j) in the GLCM.

The Haralick Maximum Contrast values are obtained by analyzing the calibrated and blurred gray level image acquired and saved in the Intra-Article Gray Level Variation Test Method using image analysis software (a suitable image analysis software is MATLAB available from The Mathworks, Inc., Natick, MA). A Haralick Contrast value is calculated in the 0° (horizontal), 45°, 90° (vertical), and 135° directions over each one of the integer pixel distances between the pixel of interest and its neighbor—ranging from 1 to 150 using a symmetric gray level co-occurrence matrix with 256 gray levels. For the 150 Haralick contrast values obtained in the 0° direction, the maximum contrast value is identified (rounding to the nearest whole number) and reported as the Haralick Maximum 0° Contrast value. For the 150 Haralick contrast values obtained in the 90° direction, the maximum contrast value is identified (rounding to the nearest whole number) and reported as the Haralick Maximum 90° Contrast value. For each of the 150 integer pixel distances, the arithmetic mean contrast value amongst all four directions is calculated (i.e., at each particular integer pixel distance an arithmetic mean is calculated that is the mean of 1) the 0° Haralick Contrast value at that integer pixel distance, 2) the 45° Haralick Contrast value at that integer pixel distance, 3) the 90° Haralick Contrast value at that integer pixel distance, and 4) the 135° Haralick Contrast value at that integer pixel distance). And from those 150 calculated means, the maximum value of those means is identified and reported as the Haralick Maximum Mean Contrast value (rounding to the nearest whole number).

Gray Level Contrast Slope Test Method

The Gray Level Contrast Slope values are obtained by analyzing the calibrated and blurred gray level image acquired and saved in the Intra-Article Gray Level Variation Test Method using image analysis software (a suitable image analysis software is ImageJ v. 1.52 or equivalent, National Institute of Health, USA).

The image is opened in the image analysis software and the boundary between two adjacent regions is identified. The boundary between regions is identified by visual discernment, or by differences in intensive properties when compared to other regions within the sample. For example, a region boundary can be identified based by visually discerning a difference when compared to another region in the sample. Or any of the intensive properties detailed herein can be used to discern region boundaries on either the physical sample itself or the gray level image, such as a change in basis weight. Once the boundary between two regions has been identified the largest circular region of interest that can be inscribed within each region is drawn, such that the inscribed circles are contiguous with each other at the boundary between the two regions. The smaller of the two inscribed circles is identified, and the larger circular region of interest is replaced with one of equivalent size to the smaller region, such that the two regions of interest still touch at the contiguous point. The arithmetic mean gray level value within both of these circular regions of interest is calculated. The linear distance is measured, to the nearest 0.001 mm, between the centers of the two circles. The Gray Level Contrast Slope is calculated by dividing the absolute value difference of the mean gray levels of the two regions by the distance between their centers. Record this value as the Gray Level Contrast Slope to the nearest 0.01 Gray Level/mm.

Inter-Article Gray Level Variation Test Method

The Inter-Article Gray Level Variation Test Method is used to determine the uniformity of gray level values between six separate, replicate nonwoven fabric images of the same visually discernable zone pattern. A flatbed scanner capable of scanning a minimum of 24 bit color at 150 dpi with manual control of color management (suitable scanner is an Epson Perfection V750 Pro from Epson America Inc., Long Beach CA, or equivalent) is used to acquire images. The scanner is interfaced with a computer running color calibration software capable of calibrating the scanner against a color reflection IT8 target utilizing a corresponding reference file compliant with ANSI method IT8.7/2-1993 (suitable color calibration software is Monaco EZColor or ilStudio available from X-Rite Grand Rapids, MI, or equivalent). The color calibration software constructs an International Color Consortium (ICC) color profile for the scanner, which is used to color correct an output image using an image analysis program that supports application of ICC profiles (a suitable program is Photoshop CS4 available from Adobe Systems Inc., San Jose, CA, or equivalent). The color corrected image is then converted to grayscale for subsequent gray level image analysis (a suitable image analysis software is MATLAB available from The Mathworks, Inc., Natick, MA).

To obtain each of the specimens, an absorbent article is taped to a rigid flat surface in a planar configuration. Any leg elastics present may be cut to facilitate laying the article flat. The outer boundary of the region lying above the absorbent core of the article is identified and marked on the outward facing surface of the layer. The specimen is removed from the underlying layers of the article by cutting around the outer perimeter of the article with a razor blade. The layer specimen is carefully removed such that its longitudinal and lateral extension is maintained to avoid distortion of the material. A cryogenic spray (such as Cyto-Freeze, Control Company, Houston TX, or equivalent) can be used to remove the specimen from the underlying layers if necessary. Six replicate specimens obtained from six substantially similar absorbent articles from the same package are prepared for analysis. The samples are conditioned at about 23° C.±2° C. and about 50%±2% relative humidity for 2 hours prior to testing.

The scanner is turned on 30 minutes prior to calibration and image acquisition. Deselect any automatic color correction or color management options that may be included in the scanner software. If the automatic color management cannot be disabled, the scanner is not appropriate for this application. The recommended procedures of the color calibration software are followed to create and export an ICC color profile for the scanner. The color calibration software compares an acquired IT8 target image to a corresponding reference file to create and export the ICC color profile for a scanner, which will be applied within the image analysis program to correct the color of subsequent output images.

The scanner lid is opened and the sample carefully laid flat on the center of the scanner glass with the outward facing surface of the specimen oriented toward the glass. The specimen is backed with a black glass tile (P/N 11-0050-30, available from HunterLab, Reston, VA, or equivalent) prior to acquiring the image. An image of a visually discernable zone is acquired and imported into the image analysis software at 24 bit color with a resolution of 150 dpi (approximately 5.9 pixels per mm) in reflectance mode. The ICC color profile is assigned to the image producing a color corrected RGB image. The RGB image is then converted to an 8 bit grayscale according to the following weighted sum of the R, G, and B components.

$$\text{Gray Level}=0.2989 \times R + 0.5870 \times G + 0.1140 \times B$$

The image is smoothed and blurred by applying a 2D Gaussian filter with a standard deviation of the Gaussian distribution (sigma) equal to 4, and the boundary padded by repeating border elements. This calibrated and blurred gray level image is saved in an uncompressed format, such as a TIFF file prior to analysis. This procedure is repeated on each of the six samples to obtain six replicate images of the same visually discernable zone.

Each of the six calibrated and blurred gray level images is opened in the image analysis software. The arithmetic mean gray level value of each of the six images is measured and recorded. The standard deviation of the recorded means is calculated and reported as the Gray Level Variation to the nearest 0.1.

Examples/Combinations

1. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
    wherein the first visually discernable zone has a Gray Level Variation of between about 0.1 and about 10.0, as measured according to the Intra-Article Gray Level Variation Test Method defined herein.
2. The nonwoven fabric of Paragraph 1, wherein the Gray Level Variation is between about 0.1 and about 7.0.
3. The nonwoven fabric of Paragraph 1, wherein the Gray Level Variation is between about 0.1 and about 4.1.
4. The nonwoven fabric of Paragraph 1, wherein the Gray Level Variation is less than 4.2.
5. A package comprising a plurality of disposable absorbent articles, wherein each disposable absorbent article includes a nonwoven fabric, wherein each nonwoven fabric comprises a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
    wherein the first visually discernable zones of the nonwoven fabrics of the plurality of disposable articles of the package have a Gray Level Variation of between about 0.1 and about 10.0, as measured according to the Inter-Article Gray Level Variation Test Method defined herein.
6. The package of Paragraph 5, wherein the disposable absorbent article is a diaper, feminine hygiene pad, or adult incontinence product.
7. The package of Paragraph 5, wherein the nonwoven fabric is selected from a topsheet and a backsheet nonwoven.
8. The package of Paragraph 5, wherein the nonwoven fabric is a topsheet.
9. The package of Paragraph 5, wherein the Gray Level Variation is between about 0.1 and about 5.0.
10. The package of Paragraph 5, wherein the Gray Level Variation is between about 0.1 and about 3.0.
11. The package of Paragraph 5, wherein the Gray Level Variation is less than 1.8.
12. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
    wherein the first visually discernable zone has a Haralick Maximum Mean Contrast Value of between about 80 and about 750, as measured according to the Haralick Maximum Contrast Test Method defined herein.
13. The nonwoven fabric of Paragraph 12, wherein the Haralick Maximum Mean Contrast Value is between about 100 and about 600.
14. The nonwoven fabric of Paragraph 12, wherein the Haralick Maximum Mean Contrast Value is greater than 80.
15. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
    wherein the first visually discernable zone has a Haralick Maximum 90° Contrast Value of between about 80 and about 750, as measured according to the Haralick Maximum Contrast Test Method defined herein.
16. The nonwoven fabric of Paragraph 15, wherein the Haralick Maximum 90° Contrast Value is between about 100 and about 600.
17. The nonwoven fabric of Paragraph 15, wherein the Haralick Maximum 90° Contrast Value is greater than 80.
18. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
    wherein the first visually discernable zone has a Haralick Maximum 0° Contrast Value of between about 80 and about 750, as measured according to the Haralick Maximum Contrast Test Method defined herein.
19. The nonwoven fabric of Paragraph 18, wherein the Haralick Maximum 0° Contrast Value is between about 100 and about 600.
20. The nonwoven fabric of Paragraph 18, wherein the Haralick Maximum 0° Contrast Value is greater than 80.
21. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
    wherein the first visually discernable zone has a Gray Level Variation of between about 0.1 and about 10.0, as measured according to the Intra-Article Gray Level Variation Test Method defined herein; and wherein the first visually discernable zone has a Haralick Maximum Mean Contrast Value of between about 80 and about 750, as measured according to the Haralick Maximum Contrast Test Method defined herein.
22. The nonwoven fabric of Paragraph 21, wherein the Gray Level Variation is between about 0.1 and about 7.0.
23. The nonwoven fabric of Paragraph 21, wherein the Gray Level Variation is between about 0.1 and about 4.1.
24. The nonwoven fabric of Paragraph 21, wherein the Gray Level Variation is less than 4.2.
25. The nonwoven fabric of Paragraph 21, wherein the Haralick Maximum Mean Contrast Value is between about 100 and about 600.
26. The nonwoven fabric of Paragraph 21, wherein the Haralick Maximum Mean Contrast Value is greater than 80.
27. A package comprising a plurality of disposable absorbent articles, wherein each disposable absorbent article includes a nonwoven fabric, wherein each nonwoven fabric comprises a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property;
wherein the first visually discernable zones of the nonwoven fabrics of the plurality of disposable articles of the package have a Gray Level Variation of between about 0.1 and about 10.0, as measured according to the Inter-Article Gray Level Variation Test Method defined herein;
wherein the first visually discernable zone on the nonwoven fabric of at least one of the disposable absorbent articles of the package has a Haralick Maximum Mean Contrast Value of between about 80 and about 750, as measured according to the Haralick Maximum Contrast Test Method defined herein.
28. The package of Paragraph 27, wherein the disposable absorbent article is a diaper, feminine hygiene pad, or adult incontinence product.
29. The package of Paragraph 27, wherein the nonwoven fabric is a topsheet.
30. The package of Paragraph 27, wherein the nonwoven fabric is a backsheet.
31. The package of Paragraph 27, wherein the Gray Level Variation is between about 0.1 and about 5.0.
32. The package of Paragraph 27, wherein the Gray Level Variation is between about 0.1 and about 3.0.
33. The package of Paragraph 27, wherein the Gray Level Variation is less than 1.8.
34. The package of Paragraph 27, wherein the Haralick Maximum Mean Contrast Value of the first disposable article is between about 100 and about 600.
35. The package of Paragraph 27, wherein the Haralick Maximum Mean Contrast Value of the first disposable article is greater than 80.
36. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein at least one of the microzones has a Gray Level Contrast Slope of between about 5.0 to about 35.0, as measured according to Gray Level Contrast Slope Test Method defined herein.
37. The nonwoven fabric of Paragraph 36, wherein the Gray Level Contrast Slope is between about 11.0 and about 25.0.
38. The nonwoven fabric of Paragraph 36, wherein the Gray Level Contrast Slope is greater than 11.0.
39. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the first visually discernible zone has a periodic Haralick Wave Response, as determined according to the Haralick Maximum Contrast Test Method defined herein.
40. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
a. thickness,
b. basis weight, and
c. volumetric density;
wherein the first visually discernable zone has a Gray Level Variation of between about 0.1 and about 10.0, as measured according to the Intra-Article Gray Level Variation Test Method defined herein.
41. The nonwoven fabric of Paragraph 40, wherein the Gray Level Variation is between about 0.1 and about 7.0.
42. The nonwoven fabric of Paragraph 40, wherein the Gray Level Variation is between about 0.1 and about 4.1.
43. The nonwoven fabric of Paragraph 40, wherein the Gray Level Variation is less than 4.2.
44. A package comprising a plurality of disposable absorbent articles, wherein each disposable absorbent article includes a nonwoven fabric, wherein each nonwoven fabric comprises a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
d. thickness,
e. basis weight, and
f. volumetric density;
wherein the first visually discernable zones of the nonwoven fabrics of the plurality of disposable articles of the package have a Gray Level Variation of between about 0.1 and about 10.0, as measured according to the Inter-Article Gray Level Variation Test Method defined herein.

45. The package of Paragraph 44, wherein the disposable absorbent article is a diaper, feminine hygiene pad, or adult incontinence product.

46. The package of Paragraph 44, wherein the nonwoven fabric is a topsheet.

47. The package of Paragraph 44, wherein the nonwoven fabric is a backsheet.

48. The package of Paragraph 44, wherein the Gray Level Variation is between about 0.1 and about 5.0.

49. The package of Paragraph 44, wherein the Gray Level Variation is between about 0.1 and about 3.0.

50. The package of Paragraph 44, wherein the Gray Level Variation is less than 1.8.

51. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
g. thickness,
h. basis weight, and
i. volumetric density;
wherein the first visually discernable zone has a Haralick Maximum Mean Contrast Value of between about 80 and about 750, as measured according to the Haralick Maximum Contrast Test Method defined herein.

52. The nonwoven fabric of Paragraph 51, wherein the Haralick Maximum Mean Contrast Value is between about 100 and about 600.

53. The nonwoven fabric of Paragraph 51, wherein the Haralick Maximum Mean Contrast Value is greater than 80.

54. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
j. thickness,
k. basis weight, and
l. volumetric density;
wherein the first visually discernable zone has a Haralick Maximum 90° Contrast Value of between about 80 and about 750, as measured according to the Haralick Maximum Contrast Test Method defined herein.

55. The nonwoven fabric of Paragraph 54, wherein the Haralick Maximum 90° Contrast Value is between about 100 and about 600.

56. The nonwoven fabric of Paragraph 54, wherein the Haralick Maximum 90° Contrast Value is greater than 80.

57. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
m. thickness,
n. basis weight, and
o. volumetric density;
wherein the first visually discernable zone has a Haralick Maximum 0° Contrast Value of between about 80 and about 750, as measured according to the Haralick Maximum Contrast Test Method defined herein.

58. The nonwoven fabric of Paragraph 57, wherein the Haralick Maximum 0° Contrast Value is between about 100 and about 600.

59. The nonwoven fabric of Paragraph 57, wherein the Haralick Maximum 0° Contrast Value is greater than 80.

60. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
p. thickness,
q. basis weight, and
r. volumetric density;
wherein the first visually discernable zone has a Gray Level Variation of between about 0.1 and about 10.0, as measured according to the Intra-Article Gray Level Variation Test Method defined herein; and
wherein the first visually discernable zone has a Haralick Maximum Mean Contrast Value of between about 80 and about 750, as measured according to the Haralick Maximum Contrast Test Method defined herein.

61. The nonwoven fabric of Paragraph 60, wherein the Gray Level Variation is between about 0.1 and 7.0.

62. The nonwoven fabric of Paragraph 60, wherein the Gray Level Variation is between about 0.1 and about 4.1.

63. The nonwoven fabric of Paragraph 60, wherein the Gray Level Variation is less than 4.2.

64. The nonwoven fabric of Paragraph 60, wherein the Haralick Maximum Mean Contrast Value is between about 100 and about 600.

65. The nonwoven fabric of Paragraph 60, wherein the Haralick Maximum Mean Contrast Value is greater than 80.

66. A package comprising a plurality of disposable absorbent articles, wherein each disposable absorbent article includes a nonwoven fabric, wherein each nonwoven fabric comprises a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
a. thickness,
b. basis weight, and
c. volumetric density;
  wherein the first visually discernable zones of the nonwoven fabrics of the plurality of disposable articles of the package have a Gray Level Variation of between about 0.1 and about 10.0, as measured according to the Inter-Article Gray Level Variation Test Method defined herein;
  wherein the first visually discernable zone on the nonwoven fabric of at least one of the disposable absorbent articles of the package has a Haralick Maximum Mean Contrast Value of between about 80 and about 750, as measured according to the Haralick Maximum Contrast Test Method defined herein.

67. The package of Paragraph 67, wherein the disposable absorbent article is a diaper, feminine hygiene pad, or adult incontinence product.
68. The package of Paragraph 67, wherein the nonwoven fabric is a topsheet.
69. The package of Paragraph 67, wherein the nonwoven fabric is a backsheet.
70. The package of Paragraph 67, wherein the Gray Level Variation is between about 0.1 and 5.0.
71. The package of Paragraph 67, wherein the Gray Level Variation is between about 0.1 and about 3.0.
72. The package of Paragraph 67, wherein the Gray Level Variation is less than 1.8.
73. The package of Paragraph 67, wherein the Haralick Maximum Mean Contrast Value of the first disposable article is between about 100 and about 600.
74. The package of Paragraph 67, wherein the Haralick Maximum Mean Contrast Value of the first disposable article is greater than 80.
75. A nonwoven fabric comprising a first surface and a second surface, and at least a first visually discernable zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
s. thickness,
t. basis weight, and
u. volumetric density;
  wherein at least one of the microzones has a Gray Level Contrast Slope of between about 10.0 to about 30.0, as measured according to Gray Level Contrast Slope Test Method defined herein.
76. The nonwoven fabric of Paragraph 75, wherein the Gray Level Contrast Slope is between about 11.0 and about 25.0.
77. The nonwoven fabric of Paragraph 75, wherein the Gray Level Contrast Slope is greater than 11.0.
78. A nonwoven fabric comprising a first surface and a second surface, and at least a first visually discernable zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
v. thickness,
w. basis weight, and
x. volumetric density;
  wherein the first visually discernible zone has a periodic Haralick Wave Response, as measured according to the Haralick Maximum Contrast Test Method defined herein.
79. A nonwoven fabric comprising a first surface and a second surface, and at least a first visually discernible zone and a second visually discernible zone on at least one of the first surface and the second surface, the first and second visually discernable zones having a pattern of three-dimensional features, each of the three-dimensional features defining a microzone comprising a first region and a second region, the first and second regions having a difference in values for an intensive property;
  wherein at least one of the first and second visually discernable zones have a Gray Level Variation of between about 0.1 and about 10.0, as measured according to the Intra-Article Gray Level Variation Test Method defined herein.
80. The nonwoven fabric of Paragraph 79, wherein the Gray Level Variation is between about 0.1 and 7.0.
81. The nonwoven fabric of Paragraph 79, wherein the Gray Level Variation is between about 0.1 and about 4.1.
82. The nonwoven fabric of Paragraph 79, wherein the Gray Level Variation is less than 4.2.
83. A package comprising a plurality of disposable absorbent articles, wherein each disposable absorbent article includes a nonwoven fabric, wherein each nonwoven fabric comprises a first surface and a second surface, and at least a first visually discernible zone and a second visually discernible zone on at least one of the first surface and the second surface, the first and second visually discernable zones having a pattern of three-dimensional features, each of the three-dimensional features defining a microzone comprising a first region and a second region, the first and second regions having a difference in values for an intensive property;
  wherein the first visually discernable zones of the nonwoven fabrics of the plurality of disposable articles of the package have a Gray Level Variation of between about 0.1 and about 10.0, as measured according to the Inter-Article Gray Level Variation Test Method defined herein; and
  wherein the second visually discernable zones of the nonwoven fabrics of the plurality of disposable articles of the package have a Gray Level Variation of between about 0.1 and about 10.0, as measured according to the Inter-Article Gray Level Variation Test Method defined herein.
84. The package of Paragraph 83, wherein the disposable absorbent article is a diaper, feminine hygiene pad, or adult incontinence product.
85. The package of Paragraph 83, wherein the nonwoven fabric is selected from a topsheet and a backsheet.
86. The package of Paragraph 83, wherein the nonwoven fabric is a topsheet.
87. The package of Paragraph 83, wherein the Gray Level Variation is between about 0.1 and 5.0.
88. The package of Paragraph 83, wherein the Gray Level Variation is between about 0.1 and about 4.1.

89. The package of Paragraph 83, wherein the Gray Level Variation is less than 4.2.
90. A nonwoven fabric comprising a first surface and a second surface, and at least a first visually discernible zone and a second visually discernible zone on at least one of the first surface and the second surface, the first and second visually discernable zones having a pattern of three-dimensional features, each of the three-dimensional features defining a microzone comprising a first region and a second region, the first and second regions having a difference in values for an intensive property; wherein the first and second visually discernable zones have a Haralick Maximum Mean Contrast Value of between about 80 and about 750, as measured according to the Haralick Maximum Contrast Test Method defined herein.
91. The nonwoven fabric of Paragraph 90, wherein the Haralick Maximum Mean Contrast Value is between about 100 and about 600.
92. The nonwoven fabric of Paragraph 90, wherein the Haralick Maximum Mean Contrast Value is greater than 80.
93. A nonwoven fabric comprising a first surface and a second surface, and at least a first visually discernible zone and a second visually discernible zone on at least one of the first surface and the second surface, the first and second visually discernable zones having a pattern of three-dimensional features, each of the three-dimensional features defining a microzone comprising a first region and a second region, the first and second regions having a difference in values for an intensive property; wherein the first and second visually discernable zones have a Haralick Maximum 90° Contrast Value of between about 80 and about 750, as measured according to the Haralick Maximum Contrast Test Method defined herein.
94. The nonwoven fabric of Paragraph 93, wherein the Haralick Maximum 90° Contrast Value is between about 100 and about 600.
95. The nonwoven fabric of Paragraph 93, wherein the Haralick Maximum 90° Contrast Value is greater than 80.
96. A nonwoven fabric comprising a first surface and a second surface, and at least a first visually discernible zone and a second visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property; wherein the first and second visually discernable zones have a Haralick Maximum 0° Contrast Value of between about 80 and about 750, as measured according to the Haralick Maximum Contrast Test Method defined herein.
97. The nonwoven fabric of Paragraph 96, wherein the Haralick Maximum 0° Contrast Value is between about 100 and about 600.
98. The nonwoven fabric of Paragraph 96, wherein the Haralick Maximum 0° Contrast Value is greater than 80.
99. A nonwoven fabric comprising a first surface and a second surface, and at least a first visually discernible zone and a second visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property; wherein the first and second visually discernable zones have a Gray Level Variation of between about 0.1 and about 10.0, as measured according to the Intra-Article Gray Level Variation Test Method defined herein; and wherein the first and second visually discernable zones have a Haralick Maximum Mean Contrast Value of between about 80 and about 750, as measured according to the Haralick Maximum Contrast Test Method defined herein.
100. The nonwoven fabric of Paragraph 99, wherein the Gray Level Variation is between about 0.1 and 7.0.
101. The nonwoven fabric of Paragraph 99, wherein the Gray Level Variation is between about 0.1 and about 4.1.
102. The nonwoven fabric of Paragraph 99, wherein the Gray Level Variation is less than 4.2.
103. The nonwoven fabric of Paragraph 99, wherein the Haralick Maximum Mean Contrast Value is between about 100 and about 600.
104. The nonwoven fabric of Paragraph 99, wherein the Haralick Maximum Mean Contrast Value is greater than 80.
105. A package comprising a plurality of disposable absorbent articles, wherein each disposable absorbent article includes a nonwoven fabric, wherein each nonwoven fabric comprises a first surface and a second surface, and at least a first visually discernible zone and a second visually discernible zone on at least one of the first surface and the second surface, the first and second visually discernable zones having a pattern of three-dimensional features, each of the three-dimensional features defining a microzone comprising a first region and a second region, the first and second regions having a difference in values for an intensive property; wherein the first visually discernable zones of the nonwoven fabrics of the plurality of disposable articles of the package have a Gray Level Variation of between about 0.1 and about 10.0, as measured according to the Inter-Article Gray Level Variation Test Method defined herein; wherein the second visually discernable zones of the nonwoven fabrics of the plurality of disposable articles of the package have a Gray Level Variation of between about 0.1 and about 10.0, as measured according to the Inter-Article Gray Level Variation Test Method defined herein; wherein the first visually discernable zone on the nonwoven fabric of at least one of the disposable absorbent articles of the package has a Haralick Maximum Mean Contrast Value of between about 80 and about 750, as measured according to the Haralick Maximum Contrast Test Method defined herein.
106. The package of Paragraph 105, wherein the disposable absorbent article is a diaper, feminine hygiene pad, or adult incontinence product.
107. The package of Paragraph 105, wherein the nonwoven fabric is a topsheet.
108. The package of Paragraph 105, wherein the nonwoven fabric is a backsheet.
109. The package of Paragraph 105, wherein the Gray Level Variation is between about 0.1 and 7.0.

110. The package of Paragraph 105, wherein the Gray Level Variation is between about 0.1 about 4.1.

111. The package of Paragraph 105, wherein the Gray Level Variation is less than 4.2.

112. The package of Paragraph 105, wherein the Haralick Maximum Mean Contrast Value of the first disposable article is between about 100 and about 600.

113. The package of Paragraph 105, wherein the Haralick Maximum Mean Contrast Value of the first disposable article is greater than 80.

114. A nonwoven fabric comprising a first surface and a second surface, and at least a first visually discernible zone and a second visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
y. thickness,
z. basis weight, and
aa. volumetric density;
wherein the nonwoven fabric has one or more of the following:
  1. the first visually discernable zone has a Gray Level Variation of between about 0.1 and about 10.0, as measured according to the Intra-Article Gray Level Variation Test Method defined herein;
  2. the first visually discernable zone has a Haralick Maximum Mean Contrast Value of between about 80 and about 750, as measured according to the Haralick Maximum Contrast Test Method defined herein;
  3. the first visually discernable zone has a Haralick Maximum 90° Contrast Value of between about 80 and about 750, as measured according to the Haralick Maximum Contrast Test Method defined herein;
  4. the first visually discernable zone has a Haralick Maximum 0° Contrast Value of between about 80 and about 750, as measured according to the Haralick Maximum Contrast Test Method defined herein; and
  5. at least one of the microzones has a Gray Level Contrast Slope of between about 5.0 to about 35.0, as measured according to Gray Level Contrast Slope Test Method defined herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is thickness, basis weight, or volumetric density;
wherein the first visually discernable zone has a Haralick Maximum Mean Contrast Value of between about 80 and about 750, according to a Haralick Maximum Contrast Test Method, wherein the Haralick Maximum Mean Contrast Value of the first visually discernable zone is a maximum mean value of arithmetic mean contrast values calculated for contrast values measured at each of a plurality of integer pixel distances in each of a 0 degree, 45 degree, 90 degree, and 135 degree direction using a symmetric gray level co-occurrence matrix with 256 gray levels;
wherein the first visually discernable zone has a Haralick Maximum 90° contrast Value of between about 90 and about 600, as measured according to a Haralick Maximum Contrast Test Method, wherein the Haralick Maximum 90° contrast Value of the first visually discernable zone is a maximum contrast value of contrast values calculated for a plurality of integer pixel distances measured in a 90° direction using a symmetric gray level co-occurrence matrix with 256 gray levels.

2. The nonwoven fabric of claim 1, wherein the intensive property is basis weight.

3. The nonwoven fabric of claim 1, wherein the intensive property is volumetric density.

4. An absorbent article comprising the nonwoven fabric of claim 1.

5. The absorbent article of claim 4, wherein the nonwoven fabric is a topsheet.

6. The absorbent article of claim 4, wherein the nonwoven fabric is an outer cover.

7. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
a. thickness,
b. basis weight, and
c. volumetric density;
wherein the first visually discernable zone has a Haralick Maximum 0° contrast Value of between about 80 and about 750, as measured according to a Haralick Maximum Contrast Test Method, wherein the Haralick Maximum 0° contrast Value of the first visually discernable zone is a maximum contrast value of contrast values calculated for a plurality of integer pixel distances measured in a 0° direction using a symmetric gray level co-occurrence matrix with 256 gray levels; and wherein the first visually discernable zone has a Gray Level Variation of between 0.1 and about 7.0, according to the Intra-Article Grey Level Variation Test Method, wherein a standard deviation of an arithmetic mean gray level value measured in each of 16 regions of a 4×4 grid of a calibrated and blurred gray level image of the first visually discernible zone is the Gray Level Variation.

8. The nonwoven fabric of claim 7, wherein the Haralick Maximum 0° contrast Value is between about 100 and about 600.

9. The nonwoven fabric of claim 7, wherein the Haralick Maximum 0° contrast Value is greater than 80.

10. The nonwoven fabric of claim 7, wherein the intensive property is basis weight.

11. The nonwoven fabric of claim 7, wherein the intensive property is volumetric density.

12. An absorbent article comprising the nonwoven fabric of claim 7.

13. A nonwoven fabric comprising a first surface and a second surface, and at least a first visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is one or more of:
  a. thickness,
  b. basis weight, and
  c. volumetric density;
  wherein at least one of the microzones has a Gray Level Contrast Slope of between 11.0 to about 23.9, as measured according to the Gray Level Contrast Test Method; wherein the Gray Level Contrast Slope is calculated by dividing (i) an absolute value difference between arithmetic mean gray level values of first and second circular and contiguous regions of interest of equal size within respective first and second regions of a calibrated and blurred grey level image of the first visually discernible zone by (ii) a linear distance between centers of the first and second circular and contiguous regions of interest;
  wherein the first visually discernable zone has a Haralick Maximum 90° contrast Value of between about 90 and about 600, as measured according to a Haralick Maximum Contrast Test Method, wherein the Haralick Maximum 90° contrast Value of the first visually discernable zone is a maximum contrast value of contrast values calculated for a plurality of integer pixel distances measured in a 90° direction using a symmetric gray level co-occurrence matrix with 256 gray levels.

14. The nonwoven fabric of claim 13, wherein the intensive property is basis weight.

15. The nonwoven fabric of claim 13, wherein the intensive property is volumetric density or thickness.

16. An absorbent article comprising the nonwoven fabric of claim 13.

17. The absorbent article of claim 16, wherein the nonwoven fabric is a topsheet.

18. The absorbent article of claim 16, wherein the nonwoven fabric is an outer cover.

19. A nonwoven fabric comprising a first surface and a second surface, and at least a first visually discernible zone and a second visually discernible zone on at least one of the first surface and the second surface, the first visually discernable zone having a pattern of three-dimensional features, each of the three-dimensional features defining a microzone comprising a first region and a second region, the first and second regions having a difference in values for an intensive property, wherein the intensive property is thickness, basis weight, or volumetric density;
  wherein the first and second visually discernable zones have a Haralick Maximum 0° contrast Value of between about 80 and about 750, as measured according to a Haralick Maximum Contrast Test Method, wherein the Haralick Maximum 0° contrast Value of the first visually discernable zone is a maximum contrast value of contrast values calculated for a plurality of integer pixel distances measured in a 0° direction using a symmetric gray level co-occurrence matrix with 256 gray levels; and
  wherein at least one of the microzones has a Gray Level Contrast Slope of between 11.0 to about 23.9, as measured according to the Gray Level Contrast Test Method; wherein the Gray Level Contrast Slope is calculated by dividing (i) an absolute value difference between arithmetic mean gray level values of first and second circular and contiguous regions of interest of equal size within respective first and second regions of a calibrated and blurred grey level image of the first visually discernible zone by (ii) a linear distance between centers of the first and second circular and contiguous regions of interest.

20. The nonwoven fabric of claim 19, wherein the Haralick Maximum 0° contrast Value is between about 100 and about 600.

* * * * *